(12) United States Patent
Kang et al.

(10) Patent No.: US 10,844,121 B2
(45) Date of Patent: Nov. 24, 2020

(54) ANTIBODIES BINDING LAG-3 AND USES THEREOF

(71) Applicant: Nanjing Leads Biolabs Co., Ltd., Nanjing (CN)

(72) Inventors: Xiaoqiang Kang, Plainsboro, NJ (US); Shoupeng Lai, Germantown, MD (US); Xiao Huang, Nanjing (CN); Lijun Zhou, Beijing (CN)

(73) Assignee: NANJING LEADS BIOLABS CO., LTD, Nanjing (CN)

(*) Notice: Subject to any disclaimer, the term of this patent is extended or adjusted under 35 U.S.C. 154(b) by 111 days.

(21) Appl. No.: 16/033,465

(22) Filed: Jul. 12, 2018

(65) Prior Publication Data

US 2019/0016800 A1 Jan. 17, 2019

Related U.S. Application Data

(60) Provisional application No. 62/531,892, filed on Jul. 13, 2017.

(51) Int. Cl.
| | |
|---|---|
| *A61P 35/00* | (2006.01) |
| *C07K 16/28* | (2006.01) |
| *A61K 38/20* | (2006.01) |
| *A61K 39/395* | (2006.01) |
| *A61K 39/00* | (2006.01) |

(52) U.S. Cl.
CPC .......... *C07K 16/2803* (2013.01); *A61K 38/20* (2013.01); *A61K 38/2013* (2013.01); *A61K 39/3955* (2013.01); *A61P 35/00* (2018.01); *C07K 16/2818* (2013.01); *C07K 16/2827* (2013.01); *C07K 16/2878* (2013.01); *A61K 2039/505* (2013.01); *C07K 2317/21* (2013.01); *C07K 2317/24* (2013.01); *C07K 2317/33* (2013.01); *C07K 2317/622* (2013.01); *C07K 2317/75* (2013.01); *C07K 2317/76* (2013.01); *C07K 2317/77* (2013.01); *C07K 2317/92* (2013.01)

(58) Field of Classification Search
CPC ............................ C07K 16/2803; A61P 35/00
USPC ...................................... 424/133.1
See application file for complete search history.

*Primary Examiner* — Yan Xiao
(74) *Attorney, Agent, or Firm* — Duane Morris LLP; Thomas J. Kowalski; Deborah L. Lu

(57) ABSTRACT

The present invention provides an isolated monoclonal antibody that specifically binds LAG-3. A nucleic acid molecule encoding the antibody, an expression vector, a host cell and a method for expressing the antibody are also provided. The present invention further provides an immunoconjugate, a bispecific molecule and a pharmaceutical composition comprising the antibody, as well as a diagnostic and treatment method using an anti-LAG-3 antibody of the invention.

19 Claims, 7 Drawing Sheets

Specification includes a Sequence Listing.

SEQUENCE LISTING

```
<160> NUMBER OF SEQ ID NOS: 50

<210> SEQ ID NO 1
<211> LENGTH: 15
<212> TYPE: DNA
<213> ORGANISM: Homo sapiens

<400> SEQUENCE: 1
gattacggca tgtct                                                      15

<210> SEQ ID NO 2
<211> LENGTH: 5
<212> TYPE: PRT
<213> ORGANISM: Homo sapiens

<400> SEQUENCE: 2

Asp Tyr Gly Met Ser
1               5

<210> SEQ ID NO 3
<211> LENGTH: 51
<212> TYPE: DNA
<213> ORGANISM: Homo sapiens

<400> SEQUENCE: 3
ggcatcaact ggtctggcgg ctccacatac tatgctgaca gcgtgaaggg c              51
```

<210> SEQ ID NO 4
<211> LENGTH: 17
<212> TYPE: PRT
<213> ORGANISM: Homo sapiens

<400> SEQUENCE: 4

Gly Ile Asn Trp Ser Gly Gly Ser Thr Tyr Tyr Ala Asp Ser Val Lys
1               5                   10                  15

Gly

<210> SEQ ID NO 5
<211> LENGTH: 9
<212> TYPE: DNA
<213> ORGANISM: Homo sapiens

<400> SEQUENCE: 5 ggaggatat                                                                9

<210> SEQ ID NO 6
<211> LENGTH: 3
<212> TYPE: PRT
<213> ORGANISM: Homo sapiens

<400> SEQUENCE: 6

Gly Gly Tyr
1

<210> SEQ ID NO 7
<211> LENGTH: 33
<212> TYPE: DNA
<213> ORGANISM: Homo sapiens

<400> SEQUENCE: 7
cgggcaagtc agagcattag cagctattta aat                                    33

<210> SEQ ID NO 8
<211> LENGTH: 11
<212> TYPE: PRT
<213> ORGANISM: Homo sapiens

<400> SEQUENCE: 8

Arg Ala Ser Gln Ser Ile Ser Ser Tyr Leu Asn
1               5                   10

<210> SEQ ID NO 9
<211> LENGTH: 21
<212> TYPE: DNA
<213> ORGANISM: Homo sapiens

<400> SEQUENCE: 9
gctgcatcca gtttgcaagg t                                                 21

<210> SEQ ID NO 10
<211> LENGTH: 7
<212> TYPE: PRT
<213> ORGANISM: Homo sapiens

<400> SEQUENCE: 10

Ala Ala Ser Ser Leu Gln Gly
1               5

<210> SEQ ID NO 11
<211> LENGTH: 27

```
<212> TYPE: DNA
<213> ORGANISM: Homo sapiens

<400> SEQUENCE: 11
caacagagtt acagtacccc gtacact                                           27

<210> SEQ ID NO 12
<211> LENGTH: 9
<212> TYPE: PRT
<213> ORGANISM: Homo sapiens

<400> SEQUENCE: 12

Gln Gln Ser Tyr Ser Thr Pro Tyr Thr
1               5

<210> SEQ ID NO 13
<211> LENGTH: 90
<212> TYPE: DNA
<213> ORGANISM: Homo sapiens

<400> SEQUENCE: 13
caggtgcagc tgcaggagtc tggaggagga gtggtgagac caggaggatc cctgcgcctg       60
agctgcgccg cttctggctt cacctttgac                                       90

<210> SEQ ID NO 14
<211> LENGTH: 30
<212> TYPE: PRT
<213> ORGANISM: Homo sapiens

<400> SEQUENCE: 14

Gln Val Gln Leu Gln Glu Ser Gly Gly Gly Val Val Arg Pro Gly Gly
1               5                   10                  15
Ser Leu Arg Leu Ser Cys Ala Ala Ser Gly Phe Thr Phe Asp
            20                  25                  30

<210> SEQ ID NO 15
<211> LENGTH: 42
<212> TYPE: DNA
<213> ORGANISM: Homo sapiens

<400> SEQUENCE: 15
tgggtgaggc aggctcctgg caagggactg gagtgggtgt cc                         42

<210> SEQ ID NO 16
<211> LENGTH: 14
<212> TYPE: PRT
<213> ORGANISM: Homo sapiens

<400> SEQUENCE: 16

Trp Val Arg Gln Ala Pro Gly Lys Gly Leu Glu Trp Val Ser
1               5                   10

<210> SEQ ID NO 17
<211> LENGTH: 96
<212> TYPE: DNA
<213> ORGANISM: Homo sapiens

<400> SEQUENCE: 17
aggagcacca tctctcggga taactccaag aatacactgt acctgcagat gaatagcctg       60
agagccgagg acaccgccgt gtactattgt gctaca                                96

<210> SEQ ID NO 18
```

```
<211> LENGTH: 32
<212> TYPE: PRT
<213> ORGANISM: Homo sapiens

<400> SEQUENCE: 18

Arg Ser Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Thr
            20                  25                  30

<210> SEQ ID NO 19
<211> LENGTH: 33
<212> TYPE: DNA
<213> ORGANISM: Homo sapiens

<400> SEQUENCE: 19
tggggacagg gcaccctggt gacagtgtcc agc                                33

<210> SEQ ID NO 20
<211> LENGTH: 11
<212> TYPE: PRT
<213> ORGANISM: Homo sapiens

<400> SEQUENCE: 20

Trp Gly Gln Gly Thr Leu Val Thr Val Ser Ser
1               5                   10

<210> SEQ ID NO 21
<211> LENGTH: 69
<212> TYPE: DNA
<213> ORGANISM: Homo sapiens

<400> SEQUENCE: 21
gacatccggt tgacccagtc cccatcctcc ctgtctgcat ctgtaggaga cagagtcacc    60
attacttgc                                                           69

<210> SEQ ID NO 22
<211> LENGTH: 23
<212> TYPE: PRT
<213> ORGANISM: Homo sapiens

<400> SEQUENCE: 22

Asp Ile Arg Leu Thr Gln Ser Pro Ser Ser Leu Ser Ala Ser Val Gly
1               5                   10                  15

Asp Arg Val Thr Ile Thr Cys
            20

<210> SEQ ID NO 23
<211> LENGTH: 45
<212> TYPE: DNA
<213> ORGANISM: Homo sapiens

<400> SEQUENCE: 23
tggtatcagc agaaaccagg gaaagcccct aagctcctga tctat                   45

<210> SEQ ID NO 24
<211> LENGTH: 15
<212> TYPE: PRT
<213> ORGANISM: Homo sapiens

<400> SEQUENCE: 24

Trp Tyr Gln Gln Lys Pro Gly Lys Ala Pro Lys Leu Leu Ile Tyr
1               5                   10                  15
```

<210> SEQ ID NO 25
<211> LENGTH: 96
<212> TYPE: DNA
<213> ORGANISM: Homo sapiens

<400> SEQUENCE: 25

```
ggggtcccat caaggttcag tggcagtgga tctgggacag atttcactct caccatcagc    60
agtctgcaac ctgaagattc tgcaacttac tactgt                              96
```

<210> SEQ ID NO 26
<211> LENGTH: 32
<212> TYPE: PRT
<213> ORGANISM: Homo sapiens

<400> SEQUENCE: 26

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Ser Ala Thr Tyr Tyr Cys
            20                  25                  30

<210> SEQ ID NO 27
<211> LENGTH: 33
<212> TYPE: DNA
<213> ORGANISM: Homo sapiens

<400> SEQUENCE: 27

```
tttggccagg ggaccaagct caccgtccta ggt                                 33
```

<210> SEQ ID NO 28
<211> LENGTH: 11
<212> TYPE: PRT
<213> ORGANISM: Homo sapiens

<400> SEQUENCE: 28

Phe Gly Gln Gly Thr Lys Leu Thr Val Leu Gly
1               5                   10

<210> SEQ ID NO 29
<211> LENGTH: 1965
<212> TYPE: DNA
<213> ORGANISM: Homo sapiens

<400> SEQUENCE: 29

```
caggtgcagc tgcaggagtc tgaggaggga gtggtgagac caggaggatc cctgcgcctg    60
agctgcgccg cttctggctt cacctttgac gattacggca tgtcttgggt gaggcaggct   120
cctggcaagg gactggagtg ggtgtccggc atcaactggt ctgcggctc cacatactat    180 gctgacagcg tgaagggcag gagcaccatc tctcgggata actccaagaa tacactgtac   240
ctgcagatga atagcctgag agccgaggac accgccgtgt actattgtgc acaggagga    300 tattggggac agggcaccct ggtgacagtg tccagcgcta gcacaaaggg accttccgtg   360
ttcccactgg cccctgctc cagaagcaca tctgagtcca ccgccgctct gggctgtctg    420
gtgaaggact acttccctga gccagtgacc gtgtcctgga cagcggcgc cctgacatcc   480 ggagtgcaca cctttcccgc cgtgctccag tccagcggac tgtacagcct gtcttccgtg   540
gtgacagtgc ccagctcttc cctgggcacc aagacatata cctgcaacgt ggaccataag   600
cctagcaata ccaaggtgga taagagggtg gagtctaagt acggaccacc ttgcccacca   660
tgtccagctc ctgagtttct gggaggacca tccgtgttcc tgtttcctcc aaagcctaag   720
```

```
gacaccctga tgatctctcg gacacctgag gtgacctgcg tggtggtgga cgtgtcccag    780
gaggacccccg aggtgcagtt caactggtac gtggatggcg tggaggtgca caatgctaag    840
accaagccaa gagaggagca gtttaatagc acataccgcg tggtgtctgt gctgaccgtg    900
ctgcatcagg attggctgaa cggcaaggag tataagtgca aggtgagcaa taagggcctg    960
cccagctcta tcgagaagac aatctctaag gctaagggac agcctcgcga gccacaggtg   1020
tacaccctgc ccccttccca ggaggagatg acaaagaacc aggtgagcct gacctgtctg   1080
gtgaagggct tctatccatc tgacatcgct gtggagtggg agtccaacgg ccagcccgag   1140
aacaattaca agaccacacc acccgtgctg gactctgatg gctccttctt tctgtattcc   1200
aggctgacag tggataagag ccggtggcag gagggcaacg tgtttagctg ctctgtgatg   1260
cacgaggctc tgcacaatca ttataccccag aagtccctga gcctgtctct gggcaaggac   1320
atccggttga cccagtcccc atcctccctg tctgcatctg taggagacag agtcaccatt   1380
acttgccggg caagtcagag cattagcagc tatttaaatt ggtatcagca gaaaccaggg   1440
aaagccccta agctcctgat ctatgctgca tccagtttgc aaggtggggt cccatcaagg   1500
ttcagtggca gtggatctgg gacagatttc actctcacca tcagcagtct gcaacctgaa   1560
gattctgcaa cttactactg tcaacagagt tacagtaccc cgtacacttt tggccagggg   1620
accaagctca ccgtcctagg tcgtacggtg gctgcaccat ctgtcttcat cttcccgcca   1680
tctgatgagc agttgaaatc tggaactgcc tctgttgtgt gcctgctgaa taacttctac   1740
cccagagaag ccaaagtgca gtggaaggtg gacaacgccc tgcagagcgg aaacagccag   1800
gaaagcgtga cagagcagga ttccaaggat tccacataca gcctgagcag cacactgaca   1860
ctgtccaagg ccgactacga gaagcacaag gtgtacgcct gcgaagtgac acaccaggga   1920
ctgtcctccc ctgtgacaaa gagcttcaac agaggagaat gctga                   1965
```

<210> SEQ ID NO 30
<211> LENGTH: 654
<212> TYPE: PRT
<213> ORGANISM: Homo sapiens

<400> SEQUENCE: 30

```
Gln Val Gln Leu Gln Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
                20                  25                  30

Gly Met Ser Trp Val Arg Gln Ala Pro Gly Lys Gly Leu Glu Trp Val
            35                  40                  45

Ser Gly Ile Asn Trp Ser Gly Gly Ser Thr Tyr Tyr Ala Asp Ser Val
        50                  55                  60

Lys Gly Arg Ser Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Gly Gly Tyr Trp Gly Gln Gly Thr Leu Val Thr Val Ser Ser
            100                 105                 110

Ala Ser Thr Lys Gly Pro Ser Val Phe Pro Leu Ala Pro Cys Ser Arg
        115                 120                 125

Ser Thr Ser Glu Ser Thr Ala Ala Leu Gly Cys Leu Val Lys Asp Tyr
    130                 135                 140

Phe Pro Glu Pro Val Thr Val Ser Trp Asn Ser Gly Ala Leu Thr Ser
```

-continued

```
               145                 150                 155                 160
Gly Val His Thr Phe Pro Ala Val Leu Gln Ser Ser Gly Leu Tyr Ser
                    165                 170                 175
Leu Ser Ser Val Val Thr Val Pro Ser Ser Leu Gly Thr Lys Thr
                    180                 185                 190
Tyr Thr Cys Asn Val Asp His Lys Pro Ser Asn Thr Lys Val Asp Lys
                    195                 200                 205
Arg Val Glu Ser Lys Tyr Gly Pro Pro Cys Pro Pro Cys Pro Ala Pro
    210                 215                 220
Glu Phe Leu Gly Gly Pro Ser Val Phe Leu Phe Pro Pro Lys Pro Lys
225                 230                 235                 240
Asp Thr Leu Met Ile Ser Arg Thr Pro Glu Val Thr Cys Val Val Val
                    245                 250                 255
Asp Val Ser Gln Glu Asp Pro Glu Val Gln Phe Asn Trp Tyr Val Asp
                    260                 265                 270
Gly Val Glu Val His Asn Ala Lys Thr Lys Pro Arg Glu Glu Gln Phe
                    275                 280                 285
Asn Ser Thr Tyr Arg Val Val Ser Val Leu Thr Val Leu His Gln Asp
    290                 295                 300
Trp Leu Asn Gly Lys Glu Tyr Lys Cys Lys Val Ser Asn Lys Gly Leu
305                 310                 315                 320
Pro Ser Ser Ile Glu Lys Thr Ile Ser Lys Ala Lys Gly Gln Pro Arg
                    325                 330                 335
Glu Pro Gln Val Tyr Thr Leu Pro Pro Ser Gln Glu Glu Met Thr Lys
                    340                 345                 350
Asn Gln Val Ser Leu Thr Cys Leu Val Lys Gly Phe Tyr Pro Ser Asp
                    355                 360                 365
Ile Ala Val Glu Trp Glu Ser Asn Gly Gln Pro Glu Asn Asn Tyr Lys
    370                 375                 380
Thr Thr Pro Pro Val Leu Asp Ser Asp Gly Ser Phe Phe Leu Tyr Ser
385                 390                 395                 400
Arg Leu Thr Val Asp Lys Ser Arg Trp Gln Glu Gly Asn Val Phe Ser
                    405                 410                 415
Cys Ser Val Met His Glu Ala Leu His Asn His Tyr Thr Gln Lys Ser
                    420                 425                 430
Leu Ser Leu Ser Leu Gly Lys Asp Ile Arg Leu Thr Gln Ser Pro Ser
                    435                 440                 445
Ser Leu Ser Ala Ser Val Gly Asp Arg Val Thr Ile Thr Cys Arg Ala
    450                 455                 460
Ser Gln Ser Ile Ser Ser Tyr Leu Asn Trp Tyr Gln Gln Lys Pro Gly
465                 470                 475                 480
Lys Ala Pro Lys Leu Leu Ile Tyr Ala Ala Ser Ser Leu Gln Gly Gly
                    485                 490                 495
Val Pro Ser Arg Phe Ser Gly Ser Gly Ser Gly Thr Asp Phe Thr Leu
                    500                 505                 510
Thr Ile Ser Ser Leu Gln Pro Glu Asp Ser Ala Thr Tyr Tyr Cys Gln
                    515                 520                 525
Gln Ser Tyr Ser Thr Pro Tyr Thr Phe Gly Gln Gly Thr Lys Leu Thr
                    530                 535                 540
Val Leu Gly Arg Thr Val Ala Ala Pro Ser Val Phe Ile Phe Pro Pro
545                 550                 555                 560
Ser Asp Glu Gln Leu Lys Ser Gly Thr Ala Ser Val Val Cys Leu Leu
                    565                 570                 575
```

Asn Asn Phe Tyr Pro Arg Glu Ala Lys Val Gln Trp Lys Val Asp Asn
              580                 585                 590

Ala Leu Gln Ser Gly Asn Ser Gln Glu Ser Val Thr Glu Gln Asp Ser
          595                 600                 605

Lys Asp Ser Thr Tyr Ser Leu Ser Ser Thr Leu Thr Leu Ser Lys Ala
      610                 615                 620

Asp Tyr Glu Lys His Lys Val Tyr Ala Cys Glu Val Thr His Gln Gly
625                 630                 635                 640

Leu Ser Ser Pro Val Thr Lys Ser Phe Asn Arg Gly Glu Cys
                  645                 650

<210> SEQ ID NO 31
<211> LENGTH: 336
<212> TYPE: DNA
<213> ORGANISM: Homo sapiens

<400> SEQUENCE: 31
caggtgcagc tgcaggagtc tgaggaggga gtggtgagac caggaggatc cctgcgcctg      60
agctgcgccg cttctggctt cacctttgac gattacggca tgtcttgggt gaggcaggct     120
cctggcaagg gactggagtg ggtgtccggc atcaactggt ctggcggctc acatactat      180 gctgacagcg tgaagggcag gagccaccat ctctcgggata actccaagaa tacactgtac     240
ctgcagatga atagcctgag agccgaggac accgccgtgt actattgtgc tacaggagga     300
tattggggac agggcaccct ggtgacagtg tccagc                                336

<210> SEQ ID NO 32
<211> LENGTH: 112
<212> TYPE: PRT
<213> ORGANISM: Homo sapiens

<400> SEQUENCE: 32

Gln Val Gln Leu Gln Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Gly Ile Asn Trp Ser Gly Gly Ser Thr Tyr Tyr Ala Asp Ser Val
    50                  55                  60

Lys Gly Arg Ser Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Gly Gly Tyr Trp Gly Gln Gly Thr Leu Val Thr Val Ser Ser
            100                 105                 110

<210> SEQ ID NO 33
<211> LENGTH: 324
<212> TYPE: DNA
<213> ORGANISM: Homo sapiens

<400> SEQUENCE: 33
gacatccggt tgacccagtc cccatcctcc ctgtctgcat ctgtaggaga cagagtcacc      60
attacttgcc gggcaagtca gagcattagc agctatttaa attggtatca gcagaaacca     120
gggaaagccc ctaagctcct gatctatgct gcatccagtt tgcaaggtgg ggtcccatca     180

```
aggttcagtg gcagtggatc tgggacagat ttcactctca ccatcagcag tctgcaacct      240
gaagattctg caacttacta ctgtcaacag agttacagta ccccgtacac ttttggccag      300
gggaccaagc tcaccgtcct aggt                                             324
```

<210> SEQ ID NO 34
<211> LENGTH: 108
<212> TYPE: PRT
<213> ORGANISM: Homo sapiens

<400> SEQUENCE: 34

```
Asp Ile Arg Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Gly Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ser Ala Thr Tyr Tyr Cys Gln Gln Ser Tyr Ser Thr Pro Tyr
                85                  90                  95

Thr Phe Gly Gln Gly Thr Lys Leu Thr Val Leu Gly
            100                 105
```

<210> SEQ ID NO 35
<211> LENGTH: 1320
<212> TYPE: DNA
<213> ORGANISM: Homo sapiens

<400> SEQUENCE: 35

```
caggtgcagc tgcaggagtc tggaggagga gtggtgagac caggaggatc cctgcgcctg       60
agctgcgccg cttctggctt cacctttgac gattacggca tgtcttgggt gaggcaggct      120
cctggcaagg gactggagtg ggtgtccggc atcaactggt ctggcggctc cacatactat      180
gctgacagcg tgaagggcag gagcaccatc tctcgggata actccaagaa tacactgtac      240
ctgcagatga atagcctgag agccgaggac accgccgtgt actattgtgc tacaggagga      300
tattggggac agggcaccct ggtgacagtg tccagcgcta gcacaaaggg accttccgtg      360
ttcccactgg cccccctgct cagaagcaca tctgagtcca ccgccgctct gggctgtctg      420
gtgaaggact acttccctga gccagtgacc gtgtcctgga cagcggcgc cctgacatcc      480 ggagtgcaca cctttcccgc cgtgctccag tccagcggac tgtacagcct gtcttccgtg      540
gtgacagtgc ccagctcttc cctgggcacc aagacatata cctgcaacgt ggaccataag      600
cctagcaata ccaaggtgga taagagggtg gagtctaagt acggaccacc ttgcccacca      660
tgtccagctc ctgagtttct ggaggaccca tccgtgttcc tgtttcctcc aaagcctaag      720
gacaccctga tgatctctcg gacacctgag gtgacctgcg tggtggtgga cgtgtcccag      780
gaggaccccg aggtgcagtt caactggtac gtggatggcg tggaggtgca caatgctaag      840
accaagccaa gagaggagca gtttaatagc acataccgcg tggtgtctgt gctgaccgtg      900
ctgcatcagg attggctgaa cggcaaggag tataagtgca aggtgagcaa taagggcctg      960
cccagctcta tcgagaagac aatctctaag gctaagggac agcctcgcga gccacaggtg     1020
tacaccctgc cccctcccca ggaggagatg acaaagaacc aggtgagcct gacctgtctg     1080
```

```
gtgaagggct tctatccatc tgacatcgct gtggagtggg agtccaacgg ccagcccgag    1140
aacaattaca agaccacacc acccgtgctg gactctgatg gctccttctt tctgtattcc    1200
aggctgacag tggataagag ccggtggcag gagggcaacg tgtttagctg ctctgtgatg    1260
cacgaggctc tgcacaatca ttatacccag aagtccctga gcctgtctct gggcaagtga    1320
```

<210> SEQ ID NO 36
<211> LENGTH: 439
<212> TYPE: PRT
<213> ORGANISM: Homo sapiens

<400> SEQUENCE: 36

```
Gln Val Gln Leu Gln Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Gly Ile Asn Trp Ser Gly Ser Thr Tyr Tyr Ala Asp Ser Val
    50                  55                  60

Lys Gly Arg Ser Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Gly Gly Tyr Trp Gly Gln Gly Thr Leu Val Thr Val Ser Ser
            100                 105                 110

Ala Ser Thr Lys Gly Pro Ser Val Phe Pro Leu Ala Pro Cys Ser Arg
        115                 120                 125

Ser Thr Ser Glu Ser Thr Ala Ala Leu Gly Cys Leu Val Lys Asp Tyr
    130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Lys Thr
            180                 185                 190

Tyr Thr Cys Asn Val Asp His Lys Pro Ser Asn Thr Lys Val Asp Lys
        195                 200                 205

Arg Val Glu Ser Lys Tyr Gly Pro Pro Cys Pro Pro Cys Pro Ala Pro
    210                 215                 220

Glu Phe Leu Gly Gly Pro Ser Val Phe Leu Phe Pro Pro Lys Pro Lys
225                 230                 235                 240

Asp Thr Leu Met Ile Ser Arg Thr Pro Glu Val Thr Cys Val Val Val
                245                 250                 255

Asp Val Ser Gln Glu Asp Pro Glu Val Gln Phe Asn Trp Tyr Val Asp
            260                 265                 270

Gly Val Glu Val His Asn Ala Lys Thr Lys Pro Arg Glu Glu Gln Phe
        275                 280                 285

Asn Ser Thr Tyr Arg Val Val Ser Val Leu Thr Val Leu His Gln Asp
    290                 295                 300

Trp Leu Asn Gly Lys Glu Tyr Lys Cys Lys Val Ser Asn Lys Gly Leu
305                 310                 315                 320

Pro Ser Ser Ile Glu Lys Thr Ile Ser Lys Ala Lys Gly Gln Pro Arg
                325                 330                 335
```

```
Glu Pro Gln Val Tyr Thr Leu Pro Pro Ser Gln Glu Met Thr Lys
                340                 345                 350

Asn Gln Val Ser Leu Thr Cys Leu Val Lys Gly Phe Tyr Pro Ser Asp
            355                 360                 365

Ile Ala Val Glu Trp Glu Ser Asn Gly Gln Pro Glu Asn Asn Tyr Lys
        370                 375                 380

Thr Thr Pro Pro Val Leu Asp Ser Asp Gly Ser Phe Phe Leu Tyr Ser
385                 390                 395                 400

Arg Leu Thr Val Asp Lys Ser Arg Trp Gln Gly Asn Val Phe Ser
                405                 410                 415

Cys Ser Val Met His Glu Ala Leu His Asn His Tyr Thr Gln Lys Ser
                420                 425                 430

Leu Ser Leu Ser Leu Gly Lys
            435
```

<210> SEQ ID NO 37
<211> LENGTH: 648
<212> TYPE: DNA
<213> ORGANISM: Homo sapiens

<400> SEQUENCE: 37

```
gacatccggt tgacccagtc cccatcctcc ctgtctgcat ctgtaggaga cagagtcacc      60
attacttgcc gggcaagtca gagcattagc agctatttaa attggtatca gcagaaacca    120
gggaaagccc ctaagctcct gatctatgct gcatccagtt tgcaaggtgg ggtcccatca    180
aggttcagtg gcagtggatc tgggacagat ttcactctca ccatcagcag tctgcaacct    240
gaagattctg caacttacta ctgtcaacag agttacagta ccccgtacac ttttggccag    300
gggaccaagc tcaccgtcct aggtcgtacg gtggctgcac catctgtctt catcttcccg    360
ccatctgatg agcagttgaa atctggaact gcctctgttg tgtgcctgct gaataacttc    420
taccccagag aagccaaagt gcagtggaag gtggacaacg ccctgcagag cggaaacagc    480
caggaaagcg tgacagagca ggattccaag gattccacat acagcctgag cagcacactg    540
acactgtcca aggccgacta cgagaagcac aaggtgtacg cctgcgaagt gacacaccag    600
ggactgtcct cccctgtgac aaagagcttc aacagaggag aatgctga                 648
```

<210> SEQ ID NO 38
<211> LENGTH: 215
<212> TYPE: PRT
<213> ORGANISM: Homo sapiens

<400> SEQUENCE: 38

```
Asp Ile Arg Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Gly Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ser Ala Thr Tyr Tyr Cys Gln Gln Ser Tyr Ser Thr Pro Tyr
                85                  90                  95

Thr Phe Gly Gln Gly Thr Lys Leu Thr Val Leu Gly Arg Thr Val Ala
            100                 105                 110
```

```
Ala Pro Ser Val Phe Ile Phe Pro Ser Asp Glu Gln Leu Lys Ser
            115                 120                 125

Gly Thr Ala Ser Val Val Cys Leu Leu Asn Asn Phe Tyr Pro Arg Glu
        130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 39
<211> LENGTH: 525
<212> TYPE: PRT
<213> ORGANISM: Homo sapiens

<400> SEQUENCE: 39

Met Trp Glu Ala Gln Phe Leu Gly Leu Leu Phe Leu Gln Pro Leu Trp
1               5                   10                  15

Val Ala Pro Val Lys Pro Leu Gln Pro Gly Ala Glu Val Pro Val Val
                20                  25                  30

Trp Ala Gln Glu Gly Ala Pro Ala Gln Leu Pro Cys Ser Pro Thr Ile
            35                  40                  45

Pro Leu Gln Asp Leu Ser Leu Leu Arg Arg Ala Gly Val Thr Trp Gln
        50                  55                  60

His Gln Pro Asp Ser Gly Pro Pro Ala Ala Ala Pro Gly His Pro Leu
65                  70                  75                  80

Ala Pro Gly Pro His Pro Ala Ala Pro Ser Ser Trp Gly Pro Arg Pro
                85                  90                  95

Arg Arg Tyr Thr Val Leu Ser Val Gly Pro Gly Gly Leu Arg Ser Gly
                100                 105                 110

Arg Leu Pro Leu Gln Pro Arg Val Gln Leu Asp Glu Arg Gly Arg Gln
            115                 120                 125

Arg Gly Asp Phe Ser Leu Trp Leu Arg Pro Ala Arg Arg Ala Asp Ala
        130                 135                 140

Gly Glu Tyr Arg Ala Ala Val His Leu Arg Asp Arg Ala Leu Ser Cys
145                 150                 155                 160

Arg Leu Arg Leu Arg Leu Gly Gln Ala Ser Met Thr Ala Ser Pro Pro
                165                 170                 175

Gly Ser Leu Arg Ala Ser Asp Trp Val Ile Leu Asn Cys Ser Phe Ser
            180                 185                 190

Arg Pro Asp Arg Pro Ala Ser Val His Trp Phe Arg Asn Arg Gly Gln
        195                 200                 205

Gly Arg Val Pro Val Arg Glu Ser Pro His His His Leu Ala Glu Ser
    210                 215                 220

Phe Leu Phe Leu Pro Gln Val Ser Pro Met Asp Ser Gly Pro Trp Gly
225                 230                 235                 240

Cys Ile Leu Thr Tyr Arg Asp Gly Phe Asn Val Ser Ile Met Tyr Asn
                245                 250                 255

Leu Thr Val Leu Gly Leu Glu Pro Pro Thr Pro Leu Thr Val Tyr Ala
```

```
                260                 265                 270
Gly Ala Gly Ser Arg Val Gly Leu Pro Cys Arg Leu Pro Ala Gly Val
            275                 280                 285

Gly Thr Arg Ser Phe Leu Thr Ala Lys Trp Thr Pro Gly Gly Gly
        290                 295                 300

Pro Asp Leu Leu Val Thr Gly Asp Asn Gly Asp Phe Thr Leu Arg Leu
305                 310                 315                 320

Glu Asp Val Ser Gln Ala Gln Ala Gly Thr Tyr Thr Cys His Ile His
                325                 330                 335

Leu Gln Glu Gln Gln Leu Asn Ala Thr Val Thr Leu Ala Ile Ile Thr
            340                 345                 350

Val Thr Pro Lys Ser Phe Gly Ser Pro Gly Ser Leu Gly Lys Leu Leu
        355                 360                 365

Cys Glu Val Thr Pro Val Ser Gly Gln Glu Arg Phe Val Trp Ser Ser
    370                 375                 380

Leu Asp Thr Pro Ser Gln Arg Ser Phe Ser Gly Pro Trp Leu Glu Ala
385                 390                 395                 400

Gln Glu Ala Gln Leu Leu Ser Gln Pro Trp Gln Cys Gln Leu Tyr Gln
                405                 410                 415

Gly Glu Arg Leu Leu Gly Ala Ala Val Tyr Phe Thr Glu Leu Ser Ser
            420                 425                 430

Pro Gly Ala Gln Arg Ser Gly Arg Ala Pro Gly Ala Leu Pro Ala Gly
        435                 440                 445

His Leu Leu Leu Phe Leu Thr Leu Gly Val Leu Ser Leu Leu Leu Leu
    450                 455                 460

Val Thr Gly Ala Phe Gly Phe His Leu Trp Arg Arg Gln Trp Arg Pro
465                 470                 475                 480

Arg Arg Phe Ser Ala Leu Glu Gln Gly Ile His Pro Pro Gln Ala Gln
                485                 490                 495

Ser Lys Ile Glu Glu Leu Glu Gln Glu Pro Glu Pro Glu Pro Glu Pro
            500                 505                 510

Glu Pro Glu Pro Glu Pro Glu Pro Glu Gln Leu
        515                 520                 525

<210> SEQ ID NO 40
<211> LENGTH: 21
<212> TYPE: PRT
<213> ORGANISM: Artificial sequence
<220> FEATURE:
<223> OTHER INFORMATION: Linker

<400> SEQUENCE: 40

Ser Gly Gly Ser Thr Ile Thr Ser Tyr Asn Val Tyr Tyr Thr Lys Leu
1               5                   10                  15

Ser Ser Ser Gly Thr
            20

<210> SEQ ID NO 41
<211> LENGTH: 1989
<212> TYPE: DNA
<213> ORGANISM: Homo sapiens

<400> SEQUENCE: 41
caggtccagc tggtgcagtc tggggggaggc gtggtccagc ctggagggtc cctgagactc      60
ccctgtgcag cctctggatt caccttcagt agctatggca tgcactgggt ccgccaggct     120
ccaggcaagg ggctggagtg ggtggcagct atatcatatg atggaagcaa taaatactac     180
```

-continued

```
gcagactccg tgaagggccg attcaccatc tccagagaca attccaagaa cacgctgtat      240
ctgcaaatga acagcctgag agctgaggac acggctgtgt attactgtgc gagagagggg      300
agctactatt tggagggtat tgactactgg ggccagggaa ccctggtcac cgtctcttca      360
gctagcacaa agggaccttc cgtgttccca ctggccccct gctccagaag cacatctgag      420
tccaccgccg ctctgggctg tctggtgaag gactacttcc ctgagccagt gaccgtgtcc      480
tggaacagcg gcgccctgac atccggagtg cacacctttc cgccgtgct ccagtccagc       540 ggactgtaca gcctgtcttc cgtggtgaca gtgcccagct cttccctggg caccaagaca      600
tatacctgca acgtggacca taagcctagc aataccaagg tggataagag ggtggagtct      660
aagtacggac accttgccc accatgtcca gctcctgagt ttctgggagg accatccgtg       720
ttcctgtttc ctccaaagcc taaggacacc ctgatgatct ctcggacacc tgaggtgacc      780
tgcgtggtgg tggacgtgtc ccaggaggac cccgaggtgc agttcaactg gtacgtggat      840
ggcgtggagg tgcacaatgc taagaccaag ccaagagagg agcagtttaa tagcacatac      900
cgcgtggtgt ctgtgctgac cgtgctgcat caggattggc tgaacggcaa ggagtataag      960
tgcaaggtga gcaataaggg cctgcccagc tctatcgaga gacaatctc taaggctaag       1020 ggacagcctc gcgagccaca ggtgtacacc ctgcccccct cccaggagga tgacaaag       1080 aaccaggtga gcctgacctg tctggtgaag ggcttctatc catctgacat cgctgtggag      1140
tgggagtcca acggccagcc cgagaacaat tacaagacca ccaccccgt gctggactct       1200 gatggctcct tctttctgta ttccaggctg acagtggata gagccggtg caggagggc        1260 aacgtgttta gctgctctgt gatgcacgag gctctgcaca atcattatac ccagaagtcc      1320
ctgagcctgt ctctgggcaa gcagtctgtg ctgacgcagc caccctcggt gtctgaagcc      1380
cccaggcaga gggtcaccat ctcctgttct ggaagcagtt ccaacatcgg agataatgct      1440
gtaaactggt accagcagct cccaggaaag gctcccacac tcctcatcta ttatgatgat      1500
ctgctgccct caggggtccc tgaccgattc tctggctcca gtctggcac tcagcctcc      1560 ctggccatca gcgggctcca gtctgaggat gaggctgaat attactgcgc agcatgggat      1620
gacagcctga aggttatgt cttcggaacg gggaccaagc tcaccgtcct aggtcagccc      1680
aaggccgccc cctccgtgac actgttccct cctcctccg aggagctgca ggccaacaag       1740
gccaccctgg tgtgcctgat ctccgacttc taccctggcg ccgtgaccgt ggcttggaag      1800
gctgactcct cccctgtgaa ggccggcgtg gagacaacca ccccctccaa gcagtccaac      1860
aacaagtacg ccgcctcctc ctacctgtcc ctgaccctg agcagtggaa gagccacagg       1920
tcctactcct gccaggtgac ccacgagggc tccaccgtgg agaagaccgt ggcccctacc      1980
gagtgctcc                                                              1989
```

<210> SEQ ID NO 42
<211> LENGTH: 663
<212> TYPE: PRT
<213> ORGANISM: Homo sapiens

<400> SEQUENCE: 42

```
Gln Val Gln Leu Val Gln Ser Gly Gly Gly Val Val Gln Pro Gly Arg
1               5                   10                  15

Ser Leu Arg Leu Pro Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45
```

-continued

```
Ala Ala Ile Ser Tyr Asp Gly Ser Asn Lys Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Gly Ser Tyr Tyr Leu Gly Ile Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
            275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys Gln
            435                 440                 445

Ser Val Leu Thr Gln Pro Pro Ser Val Ser Glu Ala Pro Arg Gln Arg
450                 455                 460
```

```
Val Thr Ile Ser Cys Ser Gly Ser Ser Ser Asn Ile Gly Asp Asn Ala
465                 470                 475                 480

Val Asn Trp Tyr Gln Gln Leu Pro Gly Lys Ala Pro Thr Leu Leu Ile
            485                 490                 495

Tyr Tyr Asp Asp Leu Leu Pro Ser Gly Val Pro Asp Arg Phe Ser Gly
        500                 505                 510

Ser Lys Ser Gly Thr Ser Ala Ser Leu Ala Ile Ser Gly Leu Gln Ser
    515                 520                 525

Glu Asp Glu Ala Glu Tyr Tyr Cys Ala Ala Trp Asp Asp Ser Leu Lys
530                 535                 540

Gly Tyr Val Phe Gly Thr Gly Thr Lys Leu Thr Val Leu Gly Gln Pro
545                 550                 555                 560

Lys Ala Ala Pro Ser Val Thr Leu Phe Pro Pro Ser Ser Glu Glu Leu
                565                 570                 575

Gln Ala Asn Lys Ala Thr Leu Val Cys Leu Ile Ser Asp Phe Tyr Pro
            580                 585                 590

Gly Ala Val Thr Val Ala Trp Lys Ala Asp Ser Ser Pro Val Lys Ala
        595                 600                 605

Gly Val Glu Thr Thr Thr Pro Ser Lys Gln Ser Asn Asn Lys Tyr Ala
    610                 615                 620

Ala Ser Ser Tyr Leu Ser Leu Thr Pro Glu Gln Trp Lys Ser His Arg
625                 630                 635                 640

Ser Tyr Ser Cys Gln Val Thr His Glu Gly Ser Thr Val Glu Lys Thr
                645                 650                 655

Val Ala Pro Thr Glu Cys Ser
            660

<210> SEQ ID NO 43
<211> LENGTH: 1953
<212> TYPE: DNA
<213> ORGANISM: Homo sapiens

<400> SEQUENCE: 43
caggtgcagc tgcaggagtc tgggggaggt gtggtacggc ctggggggtc cctgagactc      60
tcctgtgcag cctctggatt cacctttgat gattatggca tgagctgggt ccgccaagct     120
ccagggaagg gctgagtg gtctctggt attaattgga gcggtggtag cacatactac        180
gcagactccg tgaagggccg atccaccatc tccagagaca attccaagaa cacgctgtat     240
cttcaaatga acagcctgag agccgaggac acggccgtgt attactgtgc gacaggaggc     300
tactggggcc agggaacccct ggtcactgtc tcttcagcta gcacaaaggg accttccgtg    360
ttcccactgg cccctgctc cagaagcaca tctgagtcca ccgccgctct gggctgtctg     420
gtgaaggact acttccctga gccagtgacc gtgtcctgga cagcggcgc cctgacatcc     480 ggagtgcaca cctttcccgc cgtgctccag tccagcggac tgtacagcct gtcttccgtg    540
gtgacagtgc ccagctcttc cctgggcacc aagacatata cctgcaacgt ggaccataag   600
cctagcaata ccaaggtgga taagagggtg gagtctaagt acggaccacc ttgcccacca   660
tgtccagctc ctgagtttct gggaggacca tccgtgttcc tgtttcctcc aaagcctaag   720
gacaccctga tgatctctcg gacacctgag gtgacctgcg tggtggtgga cgtgtcccag   780
gaggaccccg aggtgcagtt caactggtac gtggatggcg tggaggtgca caatgctaag   840
accaagccaa gagaggagca gtttaatagc ataccgcg tggtgtctgt gctgaccgtg    900
ctgcatcagg attggctgaa cggcaaggag tataagtgca aggtgagcaa taagggcctg   960
```

-continued

```
cccagctcta tcgagaagac aatctctaag gctaagggac agcctcgcga gccacaggtg    1020
tacaccctgc ccccttccca ggaggagatg acaaagaacc aggtgagcct gacctgtctg    1080
gtgaagggct tctatccatc tgacatcgct gtggagtggg agtccaacgg ccagcccgag    1140
aacaattaca agaccacacc cccgtgctg gactctgatg gctccttctt tctgtattcc     1200
aggctgacag tggataagag ccggtggcag gagggcaacg tgtttagctg ctctgtgatg    1260
cacgaggctc tgcacaatca ttatacccag aagtccctga gcctgtctct gggcaagtcc    1320
tatgagctga ctcagccacc ctcagtgtcc gtgtccccag acagacagc cagcatcacc     1380
tgctctggag ataaattggg ggataaatat acttcctggt atcaacagaa gccaggccag    1440
tcccctctac tggtcatcta tcaatctacc aagcggccct caggaatccc tgagcgattc    1500
tctggctcca actctgggga cacagccact ctgaccatca gcgggaccca gcctatggat    1560
gaggctgact attactgtca ggcgtgggac agcagtactg cggtgttcgg cggagggacc    1620
aagctgaccg tcctaggtca gcccaaggcc gccccctccg tgacactgtt ccctccctcc    1680
tccgaggagc tgcaggccaa caaggccacc ctggtgtgcc tgatctccga cttctacccct   1740
ggcgccgtga ccgtggcttg aaggctgac tcctcccctg tgaaggccgg cgtggagaca     1800
accacccct ccaagcagtc caacaacaag tacgccgcct cctcctacct gtccctgacc     1860
cctgagcagt ggaagagcca caggtcctac tcctgccagg tgacccacga gggctccacc    1920
gtggagaaga ccgtggcccc taccgagtgc tcc                                  1953
```

<210> SEQ ID NO 44
<211> LENGTH: 651
<212> TYPE: PRT
<213> ORGANISM: Homo sapiens

<400> SEQUENCE: 44

```
Gln Val Gln Leu Gln Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Gly Ile Asn Trp Ser Gly Gly Ser Thr Tyr Tyr Ala Asp Ser Val
    50                  55                  60

Lys Gly Arg Ser Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Gly Gly Tyr Trp Gly Gln Gly Thr Leu Val Thr Val Ser Ser
            100                 105                 110

Ala Ser Thr Lys Gly Pro Ser Val Phe Pro Leu Ala Pro Cys Ser Arg
        115                 120                 125

Ser Thr Ser Glu Ser Thr Ala Ala Leu Gly Cys Leu Val Lys Asp Tyr
    130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Gly Leu Tyr Ser
                165                 170                 175

Leu Ser Ser Val Val Thr Val Pro Ser Ser Ser Leu Gly Thr Lys Thr
            180                 185                 190

Tyr Thr Cys Asn Val Asp His Lys Pro Ser Asn Thr Lys Val Asp Lys
```

-continued

```
            195                 200                 205
Arg Val Glu Ser Lys Tyr Gly Pro Pro Cys Pro Pro Cys Pro Ala Pro
210                 215                 220
Glu Phe Leu Gly Gly Pro Ser Val Phe Leu Phe Pro Pro Lys Pro Lys
225                 230                 235                 240
Asp Thr Leu Met Ile Ser Arg Thr Pro Glu Val Thr Cys Val Val Val
                    245                 250                 255
Asp Val Ser Gln Glu Asp Pro Glu Val Gln Phe Asn Trp Tyr Val Asp
                260                 265                 270
Gly Val Glu Val His Asn Ala Lys Thr Lys Pro Arg Glu Glu Gln Phe
            275                 280                 285
Asn Ser Thr Tyr Arg Val Val Ser Val Leu Thr Val Leu His Gln Asp
        290                 295                 300
Trp Leu Asn Gly Lys Glu Tyr Lys Cys Lys Val Ser Asn Lys Gly Leu
305                 310                 315                 320
Pro Ser Ser Ile Glu Lys Thr Ile Ser Lys Ala Lys Gly Gln Pro Arg
                    325                 330                 335
Glu Pro Gln Val Tyr Thr Leu Pro Pro Ser Gln Glu Glu Met Thr Lys
                340                 345                 350
Asn Gln Val Ser Leu Thr Cys Leu Val Lys Gly Phe Tyr Pro Ser Asp
            355                 360                 365
Ile Ala Val Glu Trp Glu Ser Asn Gly Gln Pro Glu Asn Asn Tyr Lys
        370                 375                 380
Thr Thr Pro Pro Val Leu Asp Ser Asp Gly Ser Phe Phe Leu Tyr Ser
385                 390                 395                 400
Arg Leu Thr Val Asp Lys Ser Arg Trp Gln Glu Gly Asn Val Phe Ser
                    405                 410                 415
Cys Ser Val Met His Glu Ala Leu His Asn His Tyr Thr Gln Lys Ser
                420                 425                 430
Leu Ser Leu Ser Leu Gly Lys Ser Tyr Glu Leu Thr Gln Pro Pro Ser
            435                 440                 445
Val Ser Val Ser Pro Gly Gln Thr Ala Ser Ile Thr Cys Ser Gly Asp
        450                 455                 460
Lys Leu Gly Asp Lys Tyr Thr Ser Trp Tyr Gln Gln Lys Pro Gly Gln
465                 470                 475                 480
Ser Pro Leu Leu Val Ile Tyr Gln Ser Thr Lys Arg Pro Ser Gly Ile
                    485                 490                 495
Pro Glu Arg Phe Ser Gly Ser Asn Ser Gly Asp Thr Ala Thr Leu Thr
                500                 505                 510
Ile Ser Gly Thr Gln Pro Met Asp Glu Ala Asp Tyr Tyr Cys Gln Ala
            515                 520                 525
Trp Asp Ser Ser Thr Ala Val Phe Gly Gly Gly Thr Lys Leu Thr Val
        530                 535                 540
Leu Gly Gln Pro Lys Ala Ala Pro Ser Val Thr Leu Phe Pro Pro Ser
545                 550                 555                 560
Ser Glu Glu Leu Gln Ala Asn Lys Ala Thr Leu Val Cys Leu Ile Ser
                    565                 570                 575
Asp Phe Tyr Pro Gly Ala Val Thr Val Ala Trp Lys Ala Asp Ser Ser
                580                 585                 590
Pro Val Lys Ala Gly Val Glu Thr Thr Thr Pro Ser Lys Gln Ser Asn
            595                 600                 605
Asn Lys Tyr Ala Ala Ser Ser Tyr Leu Ser Leu Thr Pro Glu Gln Trp
        610                 615                 620
```

Lys Ser His Arg Ser Tyr Ser Cys Gln Val Thr His Glu Gly Ser Thr
625                 630                 635                 640

Val Glu Lys Thr Val Ala Pro Thr Glu Cys Ser
            645                 650

<210> SEQ ID NO 45
<211> LENGTH: 1965
<212> TYPE: DNA
<213> ORGANISM: Homo sapiens

<400> SEQUENCE: 45

| | | | | |
|---|---|---|---|---|
| caggtgcagc | tgcaggagtc | tgggggaggt | gtggtacggc | ctgggggtc cctgagactc | 60 |
| tcctgtgcag | cctctggatt | caccttttgat | gattatggca | tgagctgggt ccgccaagct | 120 |
| ccagggaagg | ggctggagtg | gtctctggt | attaattgga | gcggtggtag cacatactac | 180 |
| gcagactccg | tgaagggccg | atccaccatc | tccagagaca | attccaagaa cacgctgtat | 240 |
| cttcaaatga | acagcctgag | agccgaggac | acggccgtgt | attactgtgc gacaggaggc | 300 |
| tactggggcc | agggaaccct | ggtcactgtc | tcttcagcta | gcacaaaggg accttccgtg | 360 |
| ttcccactgg | cccctgctc | cagaagcaca | tctgagtcca | ccgccgctct gggctgtctg | 420 |
| gtgaaggact | acttccctga | gccagtgacc | gtgtcctgga | acagcggcgc cctgacatcc | 480 |
| ggagtgcaca | cctttcccgc | cgtgctccag | tccagcggac | tgtacagcct gtcttccgtg | 540 |
| gtgacagtgc | ccagctcttc | cctgggcacc | aagacatata | cctgcaacgt ggaccataag | 600 |
| cctagcaata | ccaaggtgga | taagagggtg | gagtctaagt | acggaccacc ttgcccacca | 660 |
| tgtccagctc | ctgagtttct | gggaggacca | tccgtgttcc | tgtttcctcc aaagcctaag | 720 |
| gacaccctga | tgatctctcg | gacacctgag | gtgacctgcg | tggtggtgga cgtgtcccag | 780 |
| gaggaccccg | aggtgcagtt | caactggtac | gtggatggcg | tggaggtgca caatgctaag | 840 |
| accaagccaa | gagaggagca | gtttaatagc | acataccgcg | tggtgtctgt gctgaccgtg | 900 |
| ctgcatcagg | attggctgaa | cggcaaggag | tataagtgca | aggtgagcaa taagggcctg | 960 |
| cccagctcta | tcgagaagac | aatctctaag | gctaagggac | agcctcgcga gccacaggtg | 1020 |
| tacaccctgc | ccccttccca | ggaggagatg | acaaagaacc | aggtgagcct gacctgtctg | 1080 |
| gtgaagggct | tctatccatc | tgacatcgct | gtggagtggg | agtccaacgg ccagcccgag | 1140 |
| aacaattaca | agaccacacc | cccgtgctg | gactctgatg | gctccttctt tctgtattcc | 1200 |
| aggctgacag | tggataagag | ccggtggcag | gagggcaacg | tgtttagctg ctctgtgatg | 1260 |
| cacgaggctc | tgcacaatca | ttatacccag | aagtccctga | gcctgtctct gggcaagcag | 1320 |
| tctgtgctga | ctcagccgcc | ctcagtgtct | ggggcccag | ggcagagggt caccatctcc | 1380 |
| tgcactggga | gcagctccaa | catcggggca | ggttatgatg | tacactggta ccagcagctt | 1440 |
| ccaggaacag | cccccaaact | cctcatctat | ggtaacagca | atcggccctc agggtccct | 1500 |
| gaccgattct | ctggctccaa | gtctggcacc | tcagcctccc | tggccatcac tgggctccag | 1560 |
| gctgaggatg | aggctgatta | ttactgccag | tcctatgaca | gcagcctgag tgtggtattc | 1620 |
| ggcggaggga | ccaagctcac | cgtcctaggt | cagcccaagg | ccgcccctc cgtgacactg | 1680 |
| ttccctccct | cctccgagga | gctgcaggcc | aacaaggcca | cctgtgtg cctgatctcc | 1740 |
| gacttctacc | ctggcgccgt | gaccgtggct | tggaaggctg | actcctcccc tgtgaaggcc | 1800 |
| ggcgtggaga | caaccacccc | ctccaagcag | tccaacaaca | agtacgccgc ctcctcctac | 1860 |
| ctgtccctga | cccctgagca | gtggaagagc | cacaggtcct | actcctgcca ggtgacccac | 1920 | gagggctcca ccgtggagaa gaccgtggcc cctaccgagt gctcc            1965

<210> SEQ ID NO 46
<211> LENGTH: 655
<212> TYPE: PRT
<213> ORGANISM: Homo sapiens

<400> SEQUENCE: 46

```
Gln Val Gln Leu Gln Glu Ser Gly Gly Gly Val Val Arg Pro Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Gly Ile Asn Trp Ser Gly Gly Ser Thr Tyr Tyr Ala Asp Ser Val
    50                  55                  60

Lys Gly Arg Ser Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Gly Gly Tyr Trp Gly Gln Gly Thr Leu Val Thr Val Ser Ser
            100                 105                 110

Ala Ser Thr Lys Gly Pro Ser Val Phe Pro Leu Ala Pro Cys Ser Arg
        115                 120                 125

Ser Thr Ser Glu Ser Thr Ala Ala Leu Gly Cys Leu Val Lys Asp Tyr
    130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Lys Thr
            180                 185                 190

Tyr Thr Cys Asn Val Asp His Lys Pro Ser Asn Thr Lys Val Asp Lys
        195                 200                 205

Arg Val Glu Ser Lys Tyr Gly Pro Pro Cys Pro Cys Pro Ala Pro
    210                 215                 220

Glu Phe Leu Gly Gly Pro Ser Val Phe Leu Phe Pro Pro Lys Pro Lys
225                 230                 235                 240

Asp Thr Leu Met Ile Ser Arg Thr Pro Glu Val Thr Cys Val Val Val
                245                 250                 255

Asp Val Ser Gln Glu Asp Pro Glu Val Gln Phe Asn Trp Tyr Val Asp
            260                 265                 270

Gly Val Glu Val His Asn Ala Lys Thr Lys Pro Arg Glu Glu Gln Phe
        275                 280                 285

Asn Ser Thr Tyr Arg Val Val Ser Val Leu Thr Val Leu His Gln Asp
    290                 295                 300

Trp Leu Asn Gly Lys Glu Tyr Lys Cys Lys Val Ser Asn Lys Gly Leu
305                 310                 315                 320

Pro Ser Ser Ile Glu Lys Thr Ile Ser Lys Ala Lys Gly Gln Pro Arg
                325                 330                 335

Glu Pro Gln Val Tyr Thr Leu Pro Pro Ser Gln Glu Glu Met Thr Lys
            340                 345                 350

Asn Gln Val Ser Leu Thr Cys Leu Val Lys Gly Phe Tyr Pro Ser Asp
        355                 360                 365
```

| | | | | | | | | | | | | |
|---|---|---|---|---|---|---|---|---|---|---|---|---|
|Ile|Ala|Val|Glu|Trp|Glu|Ser|Asn|Gly|Gln|Pro|Glu|Asn Asn Tyr Lys|
| |370| | | |375| | | |380| | | |

Thr Thr Pro Pro Val Leu Asp Ser Asp Gly Ser Phe Phe Leu Tyr Ser
385 390 395 400

Arg Leu Thr Val Asp Lys Ser Arg Trp Gln Glu Gly Asn Val Phe Ser
405 410 415

Cys Ser Val Met His Glu Ala Leu His Asn His Tyr Thr Gln Lys Ser
420 425 430

Leu Ser Leu Ser Leu Gly Lys Gln Ser Val Leu Thr Gln Pro Pro Ser
435 440 445

Val Ser Gly Ala Pro Gly Gln Arg Val Thr Ile Ser Cys Thr Gly Ser
450 455 460

Ser Ser Asn Ile Gly Ala Gly Tyr Asp Val His Trp Tyr Gln Gln Leu
465 470 475 480

Pro Gly Thr Ala Pro Lys Leu Leu Ile Tyr Gly Asn Ser Asn Arg Pro
485 490 495

Ser Gly Val Pro Asp Arg Phe Ser Gly Ser Lys Ser Gly Thr Ser Ala
500 505 510

Ser Leu Ala Ile Thr Gly Leu Gln Ala Glu Asp Glu Ala Asp Tyr Tyr
515 520 525

Cys Gln Ser Tyr Asp Ser Ser Leu Ser Val Val Phe Gly Gly Gly Thr
530 535 540

Lys Leu Thr Val Leu Gly Gln Pro Lys Ala Ala Pro Ser Val Thr Leu
545 550 555 560

Phe Pro Pro Ser Ser Glu Glu Leu Gln Ala Asn Lys Ala Thr Leu Val
565 570 575

Cys Leu Ile Ser Asp Phe Tyr Pro Gly Ala Val Thr Val Ala Trp Lys
580 585 590

Ala Asp Ser Ser Pro Val Lys Ala Gly Val Glu Thr Thr Pro Ser
595 600 605

Lys Gln Ser Asn Asn Lys Tyr Ala Ala Ser Ser Tyr Leu Ser Leu Thr
610 615 620

Pro Glu Gln Trp Lys Ser His Arg Ser Tyr Ser Cys Gln Val Thr His
625 630 635 640

Glu Gly Ser Thr Val Glu Lys Thr Val Ala Pro Thr Glu Cys Ser
645 650 655

<210> SEQ ID NO 47
<211> LENGTH: 1992
<212> TYPE: DNA
<213> ORGANISM: Homo sapiens
<400> SEQUENCE: 47

```
gaggtgcagc tggtgcagtc tgggggaggc ttggtacagc cagggcggtc cctgagactc      60
tcctgtacag cttctggatt cacctttggt gattatgcca tgcactgggt ccggcaagct     120
ccagggaagg gcctggagtg gtctcaggt attagttgga atagtggtag cataggctat     180
gcggactctg tgaagggccg attcaccatc tccagagaca acgccaagaa ctcactgtat     240
ctgcaaatga acagcctgag agccgaggac acggccgtat attactgtgc gaaatttaga     300
agcagcagct ggtacgacta ctttgactcc tggggccagg gaaccctggt caccgtctct     360
tcagctagca caagggacc ttccgtgttc ccactggccc cctgctccag aagcacatct     420
gagtccaccg ccgtctctgg ctgtctggtg aaggactact ccctgagcc agtgaccgtg     480 tcctggaaca cggcgcccct gacatccgga gtgcacacct ttcccgccgt gctccagtcc     540
```

```
agcggactgt acagcctgtc ttccgtggtg acagtgccca gctcttccct gggcaccaag      600
acatatacct gcaacgtgga ccataagcct agcaatacca aggtggataa gagggtggag      660
tctaagtacg gaccaccttg cccaccatgt ccagctcctg agtttctggg aggaccatcc      720
gtgttcctgt ttcctccaaa gcctaaggac accctgatga tctctcggac acctgaggtg      780
acctgcgtgg tggtggacgt gtcccaggag gaccccgagg tgcagttcaa ctggtacgtg      840
gatggcgtgg aggtgcacaa tgctaagacc aagccaagag aggagcagtt taatagcaca      900
taccgcgtgg tgtctgtgct gaccgtgctg catcaggatt ggctgaacgg caaggagtat      960
aagtgcaagg tgagcaataa gggcctgccc agctctatcg agaagacaat ctctaaggct     1020
aagggacagc ctcgcgagcc acaggtgtac accctgcccc cttcccagga ggagatgaca     1080
aagaaccagg tgagcctgac ctgtctggtg aagggcttct atccatctga catcgctgtg     1140
gagtgggagt ccaacggcca gcccgagaac aattacaaga ccacaccacc cgtgctggac     1200
tctgatggct ccttctttct gtattccagg ctgacagtgg ataagagccg gtggcaggag     1260
ggcaacgtgt ttagctgctc tgtgatgcac gaggctctgc acaatcatta cccagaagag     1320
tccctgagcc tgtctctggg caagcagtct gtgttgacgc agccaccctc agcgtctggg     1380
acccccgggc agagggtcac catctcttgt tctggaagca gctccaacat cggaagtaat     1440
actgtaaact ggtaccagca gctcccagga acggcccca aactcctcat ctatagtaat     1500
aatcagcggc cctcaggggt ccctgaccga ttctctggct ccaagtctgg cacctcagcc     1560
tccctggcca tcagtgggct ccagtctgag gatgaggctg attattactg tgcagcatgg     1620
gatgacagcc tgaatggttg ggtgttcggc ggagggacca agctcaccgt cctaggtcag     1680
cccaaggccg ccccctccgt gacactgttc cctccctcct ccgaggagct gcaggccaac     1740
aaggccaccc tggtgtgcct gatctccgac ttctaccctg gcgccgtgac cgtggcttgg     1800
aaggctgact cctcccctgt gaaggccggc gtggagacaa ccaccccctc caagcagtcc     1860
aacaacaagt acgccgcctc ctcctacctg tccctgaccc ctgagcagtg gaagagccac     1920
aggtcctact cctgccaggt gacccacgag ggctccaccg tggagaagac cgtggcccct     1980
accgagtgct cc                                                         1992
```

<210> SEQ ID NO 48
<211> LENGTH: 664
<212> TYPE: PRT
<213> ORGANISM: Homo sapiens

<400> SEQUENCE: 48

```
Glu Val Gln Leu Val Gln Ser Gly Gly Gly Leu Val Gln Pro Gly Arg
1               5                   10                  15

Ser Leu Arg Leu Ser Cys Thr Ala Ser Gly Phe Thr Phe Gly Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Phe Arg Ser Ser Ser Trp Tyr Asp Tyr Phe Asp Ser Trp Gly
            100                 105                 110
```

```
Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Lys Thr Tyr Thr Cys Asn Val Asp His
                195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
                260                 265                 270

Glu Val Gln Phe Asn Trp Tyr Val Asp Gly Val Glu Val His Asn Ala
                275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
                420                 425                 430

Leu His Asn His Tyr Thr Gln Lys Ser Leu Ser Leu Ser Leu Gly Lys
                435                 440                 445

Gln Ser Val Leu Thr Gln Pro Pro Ser Ala Ser Gly Thr Pro Gly Gln
    450                 455                 460

Arg Val Thr Ile Ser Cys Ser Gly Ser Ser Asn Ile Gly Ser Asn
465                 470                 475                 480

Thr Val Asn Trp Tyr Gln Gln Leu Pro Gly Thr Ala Pro Lys Leu Leu
                485                 490                 495

Ile Tyr Ser Asn Asn Gln Arg Pro Ser Gly Val Pro Asp Arg Phe Ser
                500                 505                 510

Gly Ser Lys Ser Gly Thr Ser Ala Ser Leu Ala Ile Ser Gly Leu Gln
        515                 520                 525
```

```
Ser Glu Asp Glu Ala Asp Tyr Tyr Cys Ala Ala Trp Asp Asp Ser Leu
    530                 535                 540

Asn Gly Trp Val Phe Gly Gly Thr Lys Leu Thr Val Leu Gly Gln
545                 550                 555                 560

Pro Lys Ala Ala Pro Ser Val Thr Leu Phe Pro Pro Ser Ser Glu Glu
                565                 570                 575

Leu Gln Ala Asn Lys Ala Thr Leu Val Cys Leu Ile Ser Asp Phe Tyr
            580                 585                 590

Pro Gly Ala Val Thr Val Ala Trp Lys Ala Asp Ser Ser Pro Val Lys
        595                 600                 605

Ala Gly Val Glu Thr Thr Thr Pro Ser Lys Gln Ser Asn Asn Lys Tyr
    610                 615                 620

Ala Ala Ser Ser Tyr Leu Ser Leu Thr Pro Glu Gln Trp Lys Ser His
625                 630                 635                 640

Arg Ser Tyr Ser Cys Gln Val Thr His Glu Gly Ser Thr Val Glu Lys
                645                 650                 655

Thr Val Ala Pro Thr Glu Cys Ser
                660

<210> SEQ ID NO 49
<211> LENGTH: 525
<212> TYPE: PRT
<213> ORGANISM: Homo sapiens

<400> SEQUENCE: 49

Met Trp Glu Ala Gln Phe Leu Gly Leu Leu Phe Leu Gln Pro Leu Trp
1               5                   10                  15

Val Ala Pro Val Lys Pro Leu Gln Pro Gly Ala Glu Val Pro Val Val
            20                  25                  30

Trp Ala Gln Glu Gly Ala Pro Ala Gln Leu Pro Cys Ser Pro Thr Ile
        35                  40                  45

Pro Leu Gln Asp Leu Ser Leu Leu Arg Arg Ala Gly Val Thr Trp Gln
    50                  55                  60

His Gln Pro Asp Ser Gly Pro Pro Ala Ala Ala Pro Gly His Pro Leu
65                  70                  75                  80

Ala Pro Gly Pro His Pro Ala Ala Pro Ser Ser Trp Gly Pro Arg Pro
                85                  90                  95

Arg Arg Tyr Thr Val Leu Ser Val Gly Pro Gly Gly Leu Arg Ser Gly
            100                 105                 110

Arg Leu Pro Leu Gln Pro Arg Val Gln Leu Asp Glu Arg Gly Arg Gln
        115                 120                 125

Arg Gly Asp Phe Ser Leu Trp Leu Arg Pro Ala Arg Arg Ala Asp Ala
    130                 135                 140

Gly Glu Tyr Arg Ala Ala Val His Leu Arg Asp Arg Ala Leu Ser Cys
145                 150                 155                 160

Arg Leu Arg Leu Arg Leu Gly Gln Ala Ser Met Thr Ala Ser Pro Pro
                165                 170                 175

Gly Ser Leu Arg Ala Ser Asp Trp Val Ile Leu Asn Cys Ser Phe Ser
            180                 185                 190

Arg Pro Asp Arg Pro Ala Ser Val His Trp Phe Arg Asn Arg Gly Gln
        195                 200                 205

Gly Arg Val Pro Val Arg Glu Ser Pro His His His Leu Ala Glu Ser
    210                 215                 220

Phe Leu Phe Leu Pro Gln Val Ser Pro Met Asp Ser Gly Pro Trp Gly
225                 230                 235                 240
```

```
Cys Ile Leu Thr Tyr Arg Asp Gly Phe Asn Val Ser Ile Met Tyr Asn
                245                 250                 255

Leu Thr Val Leu Gly Leu Glu Pro Pro Thr Pro Leu Thr Val Tyr Ala
            260                 265                 270

Gly Ala Gly Ser Arg Val Gly Leu Pro Cys Arg Leu Pro Ala Gly Val
        275                 280                 285

Gly Thr Arg Ser Phe Leu Thr Ala Lys Trp Thr Pro Pro Gly Gly Gly
    290                 295                 300

Pro Asp Leu Leu Val Thr Gly Asp Asn Gly Asp Phe Thr Leu Arg Leu
305                 310                 315                 320

Glu Asp Val Ser Gln Ala Gln Ala Gly Thr Tyr Thr Cys His Ile His
                325                 330                 335

Leu Gln Glu Gln Gln Leu Asn Ala Thr Val Thr Leu Ala Ile Ile Thr
            340                 345                 350

Val Thr Pro Lys Ser Phe Gly Ser Pro Gly Ser Leu Gly Lys Leu Leu
        355                 360                 365

Cys Glu Val Thr Pro Val Ser Gly Gln Glu Arg Phe Val Trp Ser Ser
    370                 375                 380

Leu Asp Thr Pro Ser Gln Arg Ser Phe Ser Gly Pro Trp Leu Glu Ala
385                 390                 395                 400

Gln Glu Ala Gln Leu Leu Ser Gln Pro Trp Gln Cys Gln Leu Tyr Gln
                405                 410                 415

Gly Glu Arg Leu Leu Gly Ala Ala Val Tyr Phe Thr Glu Leu Ser Ser
            420                 425                 430

Pro Gly Ala Gln Arg Ser Gly Arg Ala Pro Gly Ala Leu Pro Ala Gly
        435                 440                 445

His Leu Leu Leu Phe Leu Ile Leu Gly Val Leu Ser Leu Leu Leu Leu
    450                 455                 460

Val Thr Gly Ala Phe Gly Phe His Leu Trp Arg Arg Gln Trp Arg Pro
465                 470                 475                 480

Arg Arg Phe Ser Ala Leu Glu Gln Gly Ile His Pro Pro Gln Ala Gln
                485                 490                 495

Ser Lys Ile Glu Glu Leu Glu Gln Glu Pro Glu Pro Glu Pro Glu Pro
            500                 505                 510

Glu Pro Glu Pro Glu Pro Glu Pro Glu Pro Glu Gln Leu
        515                 520                 525

<210> SEQ ID NO 50
<211> LENGTH: 450
<212> TYPE: PRT
<213> ORGANISM: Macaca mulatta

<400> SEQUENCE: 50

Met Trp Glu Ala Gln Phe Leu Gly Leu Leu Phe Leu Gln Pro Leu Trp
1               5                   10                  15

Val Ala Pro Val Lys Pro Pro Gln Pro Gly Ala Glu Ile Ser Val Val
            20                  25                  30

Trp Ala Gln Glu Gly Ala Pro Ala Gln Leu Pro Cys Ser Pro Thr Ile
        35                  40                  45

Pro Leu Gln Asp Leu Ser Leu Leu Arg Arg Ala Gly Val Thr Trp Gln
    50                  55                  60

His Gln Pro Asp Ser Gly Pro Pro Ala Pro Ala Pro Gly His Pro Pro
65                  70                  75                  80

Ala Pro Gly His Arg Pro Ala Ala Pro Tyr Ser Trp Gly Pro Arg Pro
```

```
                    85                  90                  95
Arg Arg Tyr Thr Val Leu Ser Val Gly Pro Gly Gly Leu Arg Ser Gly
                100                 105                 110

Arg Leu Pro Leu Gln Pro Arg Val Gln Leu Asp Glu Arg Gly Arg Gln
            115                 120                 125

Arg Gly Asp Phe Ser Leu Trp Leu Arg Pro Ala Arg Arg Ala Asp Ala
        130                 135                 140

Gly Glu Tyr Arg Ala Thr Val His Leu Arg Asp Arg Ala Leu Ser Cys
145                 150                 155                 160

Arg Leu Arg Leu Arg Val Gly Gln Ala Ser Met Thr Ala Ser Pro Pro
                165                 170                 175

Gly Ser Leu Arg Thr Ser Asp Trp Val Ile Leu Asn Cys Ser Phe Ser
            180                 185                 190

Arg Pro Asp Arg Pro Ala Ser Val His Trp Phe Arg Ser Arg Gly Gln
        195                 200                 205

Gly Arg Val Pro Val Gln Gly Ser Pro His His Leu Ala Glu Ser
210                 215                 220

Phe Leu Phe Leu Pro His Val Gly Pro Met Asp Ser Gly Leu Trp Gly
225                 230                 235                 240

Cys Ile Leu Thr Tyr Arg Asp Gly Phe Asn Val Ser Ile Met Tyr Asn
                245                 250                 255

Leu Thr Val Leu Gly Leu Glu Pro Ala Thr Pro Leu Thr Val Tyr Ala
            260                 265                 270

Gly Ala Gly Ser Arg Val Glu Leu Pro Cys Arg Leu Pro Pro Ala Val
        275                 280                 285

Gly Thr Gln Ser Phe Leu Thr Ala Lys Trp Ala Pro Pro Gly Gly Gly
            290                 295                 300

Pro Asp Leu Leu Val Ala Gly Asp Asn Gly Asp Phe Thr Leu Arg Leu
305                 310                 315                 320

Glu Asp Val Ser Gln Ala Gln Ala Gly Thr Tyr Ile Cys His Ile Arg
                325                 330                 335

Leu Gln Gly Gln Gln Leu Asn Ala Thr Val Thr Leu Ala Ile Ile Thr
            340                 345                 350

Val Thr Pro Lys Ser Phe Gly Ser Pro Gly Ser Leu Gly Lys Leu Leu
        355                 360                 365

Cys Glu Val Thr Pro Ala Ser Gly Gln Glu His Phe Val Trp Ser Pro
370                 375                 380

Leu Asn Thr Pro Ser Gln Arg Ser Phe Ser Gly Pro Trp Leu Glu Ala
385                 390                 395                 400

Gln Glu Ala Gln Leu Leu Ser Gln Pro Trp Gln Cys Gln Leu His Gln
                405                 410                 415

Gly Glu Thr Leu Leu Gly Ala Ala Val Tyr Phe Thr Glu Leu Ser Ser
            420                 425                 430

Pro Gly Ala Gln Arg Ser Gly Arg Ala Pro Gly Ala Leu Arg Ala Gly
        435                 440                 445

His Leu
450
```

ANTIBODIES BINDING LAG-3 AND USES THEREOF

RELATED APPLICATIONS AND INCORPORATION BY REFERENCE

This application claims the benefit of priority from U.S. Application 62/531,892 filed Jul. 13, 2017.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, or hereby incorporated herein by reference, and may be employed in the practice of the invention. More specifically, all referenced documents are incorporated by reference to the same extent as if each individual document was specifically and individually indicated to be incorporated by reference.

SEQUENCE STATEMENT

The instant application contains a Sequence Listing, which has been submitted electronically and is hereby incorporated by reference in its entirety. Said ASCII copy, is named SequenceListing.txt and is 70.29 kb in size.

BACKGROUND OF THE INVENTION

Therapeutic antibodies are one of the fastest growing segments of the pharmaceutical industry, especially monoclonal antibodies targeting certain disease-related cellular proteins.

One such target protein is lymphocyte-activation gene 3, also known as LAG3 (CD223), a protein encoded by the LAG3 gene in humans. LAG3 is a CD4-like protein, which like CD4, binds to MHC class II molecules, and functionally falls in the negative costimulatory group (inhibitory co-receptors) [Crawford A, et al., EJ. Curr Opin Immunol. 21:179-86(2009)], and is involved in the decline/suppression of T cell responses.

In-depth analysis showed that LAG-3 negatively regulates homeostasis, cellular proliferation and activation of T cells [Workman C J, et al., Eur J Immunol 33:970-9 (2003)]. Preclinical studies using antibody to block LAG-3 for cancer treatment show enhanced activation of antigen-specific T cells at the tumor site and disruption of tumor growth [Grosso J F, et al., J Clin Invest 117:3383-92 (2007)]. Furthermore, dual anti-LAG-3/anti-PD-1 antibody treatment cured most mice of established tumors that were largely resistant to single antibody treatment. [Woo S R, et al., Cancer Res; 72: 917-27 (2011)].

Although monoclonal antibodies binding to LAG-3 are known (e.g. US 2011/0150892 and US 2014/0093511), there is a need for additional monoclonal antibodies with enhanced binding affinity and other desirable pharmaceutical characteristics.

SUMMARY OF THE INVENTION

The present invention provides an isolated monoclonal antibody, for example, a human monoclonal antibody, that binds to LAG-3 (e.g., the human LAG-3, and monkey LAG-3) and has increased affinity compared to existing anti-LAG-3 antibodies (e.g., BMS-986016 developed by Bristol-Myers Squibb).

The antibody of the invention can be used for a variety of applications, including detection of the LAG-3 protein and stimulation of antigen-specific T cell responses in tumor-bearing or virus-bearing subjects.

Accordingly, in one aspect, the invention pertains to an isolated monoclonal antibody (e.g., a human antibody), or an antigen-binding portion thereof, having a heavy chain variable region that comprises a CDR1 region comprising an amino acid sequence of SEQ ID NO:2, a CDR2 region comprising an amino acid sequence of SEQ ID NO:4, and a CDR3 region comprising an amino acid sequence of SEQ ID NO:6. In one embodiment, the amino acid sequence of SEQ ID NO:2, 4 and 6 may be encoded by the nucleic acid sequence of SEQ ID NO:1, 3 and 5, respectively.

In one aspect, an isolated monoclonal antibody (e.g., a human antibody), or an antigen-binding portion thereof, of the present invention comprises a heavy chain variable region comprising the amino acid sequence of SEQ ID NO:32, which may be encoded by the nucleic acid sequence of SEQ ID NO: 31.

The monoclonal antibody or an antigen-binding portion thereof of the present invention in one embodiment comprises a light chain variable region that comprises a CDR1 region comprising an amino acid sequence of SEQ ID NO:8, a CDR2 region comprising an amino acid sequence of SEQ ID NO:10, and a CDR3 region comprising an amino acid sequence of SEQ ID NO:12. In one embodiment, the amino acid sequence of SEQ ID NO:8, 10 and 12 may be encoded by the nucleic acid sequence of SEQ ID NO:7, 9 and 11, respectively.

In one aspect, an isolated monoclonal antibody (e.g., a human antibody), or an antigen-binding portion thereof, of the present invention comprises a light chain variable region comprising the amino acid sequence of SEQ ID NO:34, which may be encoded by the nucleic acid sequence of SEQ ID NO: 33.

In one embodiment, the antibody, or the antigen-binding portion thereof, comprises the heavy chain variable region comprising the amino acid sequence of SEQ ID NO:32 and the light chain variable region comprising the amino acid sequence of SEQ ID NO:34.

In one embodiment, the antibody of the present invention comprises four framework regions in the heavy chain variable region having the amino acid sequences of SEQ ID NOs: 14, 16, 18 and 20, and four framework regions in the light chain variable region having the amino acid sequences of SEQ ID NOs:22, 24, 26 and 28. In one embodiment, the amino acid sequences of SEQ ID NOs: 14, 16, 18 and 20 may be encoded by the nucleic acid sequences of SEQ ID Nos:13, 15, 17 and 19, respectively. In one embodiment, the amino acid sequences of SEQ ID NOs:22, 24, 26 and 28 may be encoded by the nucleic acid sequences of SEQ ID Nos:21, 23, 25 and 27, respectively.

In one embodiment, the antibody of the present invention comprises a heavy chain having the amino acid sequence of SEQ ID NO:36, and a light chain having the amino acid sequence of SEQ ID NO: 38, which two may be encoded by the nucleic acid sequences of SEQ ID Nos:35 and 37, respectively. In one embodiment, the antibody of the present invention comprises two heavy chains each having the amino acid sequence of SEQ ID NO:36, and two light chains each having the amino acid sequence of SEQ ID NO: 38. Further, the antibody of the present invention comprises an amino acid sequence of SEQ ID NO:30, which may be encoded by the nucleic acid sequence of SEQ ID No.: 29.

In another embodiment, the antibody stimulates an antigen-specific T cell response, such as interferon gamma (IFNγ) and or interferon-2 (IL-2) production in an antigen-specific T cell response. In other embodiments, the antibody stimulates an immune response, such as an anti-tumor response (e.g., inhibition of tumor growth in an in vivo tumor graft model) or an autoimmune response (e.g., development of diabetes in NOD mice).

In another embodiment, the antibody binds to an epitope of human LAG-3, blocking the interaction of LAG-3 with MHC class II or LSECtin.

The antibody of the invention can be a full-length antibody, for example, of an IgG1, IgG2 or IgG4 isotype, optionally with a serine to proline mutation in the heavy chain constant region hinge region (at a position corresponding to position 241 as described in Angal et al. (1993) Mol. Immunol. 30:105-108), such that inter-heavy chain disulfide bridge heterogeneity is reduced or abolished. In one aspect, the constant region isotype is IgG4 with a mutation at amino acid residues 220, e.g., S220P. Alternatively, the antibody can be an antibody fragment, such as a Fab, Fab' or Fab'2 fragment, or a single chain antibody.

In another aspect of the invention, the antibody or an antigen-binding portion thereof is part of an immunoconjugate which comprises a therapeutic agent, e.g., a cytotoxin or a radioactive isotope, linked to the antibody. In another aspect, the antibody is part of a bispecific molecule which comprises a second functional moiety (e.g., a second antibody) having a different binding specificity from said antibody, or the antigen binding portion thereof. In another aspect, the antibody or an antigen binding portions thereof (e.g. a scFv, see below) can be made into part of a chimeric antigen receptor (CAR) or an engineered T cell receptor (TCR) as part of an adoptive T cell immunotherapy strategy.

A composition comprising an antibody, or an antigen-binding portion thereof, an immunoconjugate or a bispecific molecule of the invention, optionally formulated in a pharmaceutically acceptable carrier, is also provided.

A nucleic acid molecule encoding the antibody, or the antigen-binding portion (e.g., variable regions and/or CDRs) thereof, of the invention is also provided, as well as an expression vector comprising the nucleic acid and a host cell comprising the expression vector. A method for preparing an anti-LAG-3 antibody using the host cell comprising the expression vector is also provided, and comprises steps of (i) expressing the antibody in the host cell and (ii) isolating the antibody from the host cell.

In another aspect, the invention provides a method for stimulating an immune response in a subject using the anti-LAG-3 antibody of the invention. In one embodiment, the method involves stimulating an antigen-specific T cell response by contacting T cells with the antibody of the invention. In a preferred embodiment, Interferon gamma (IFNγ) and or interferon-2 (IL-2) production by the antigen-specific T cell is stimulated. In another embodiment, the subject is a tumor-bearing subject and an immune response against the tumor is stimulated. In another embodiment, the subject is a virus-bearing subject and an immune response against the virus is stimulated.

In yet another embodiment, the invention provides a method for inhibiting growth of tumor cells in a subject, comprising administering to the subject an antibody, or an antigen-binding portion thereof, of the invention. In still another embodiment, the invention provides a method for treating viral infection in a subject, comprising administering to the subject an antibody, or an antigen-binding portion thereof, of the invention. In another embodiment, the method comprises administering a composition, a bispecific, or an immunoconjugate of the invention.

In yet another embodiment, the invention provides a method for stimulating an immune response in a subject comprising administering to the subject an antibody, or an antigen-binding portion thereof, of the invention and at least one additional immunostimulatory antibody, such as an anti-PD-1 antibody, an anti-PD-L1 antibody and/or an anti-CTLA-4 antibody, such that an immune response is stimulated in the subject, for example to inhibit tumor growth or to stimulate an anti-viral response. In one embodiment, the additional immunostimulatory antibody is an anti-PD-1 antibody. In another embodiment, the additional immunostimulatory agent is an anti-PD-L1 antibody. In yet another embodiment, the additional immunostimulatory agent is an anti-CTLA-4 antibody. In yet another embodiment, an antibody, or an antigen-binding portion thereof, of the invention is administered with a cytokine (e.g., IL-2 and/or IL-21), or a costimulatory antibody (e.g., an anti-CD137 and/or anti-GITR antibody). The antibodies can be, for example, human, chimeric or humanized antibodies.

In another aspect, the invention provides an anti-LAG-3 antibody and a composition of the invention for use in the foregoing methods, or for the manufacture of a medicament for use in the foregoing methods (e.g., for treatment).

Other features and advantages of the instant disclosure will be apparent from the following detailed description and examples, which should not be construed as limiting. The contents of all references, Genbank entries, patents and published patent applications cited throughout this application are expressly incorporated herein by reference.

DETAILED DESCRIPTION OF THE INVENTION

Figure 1:
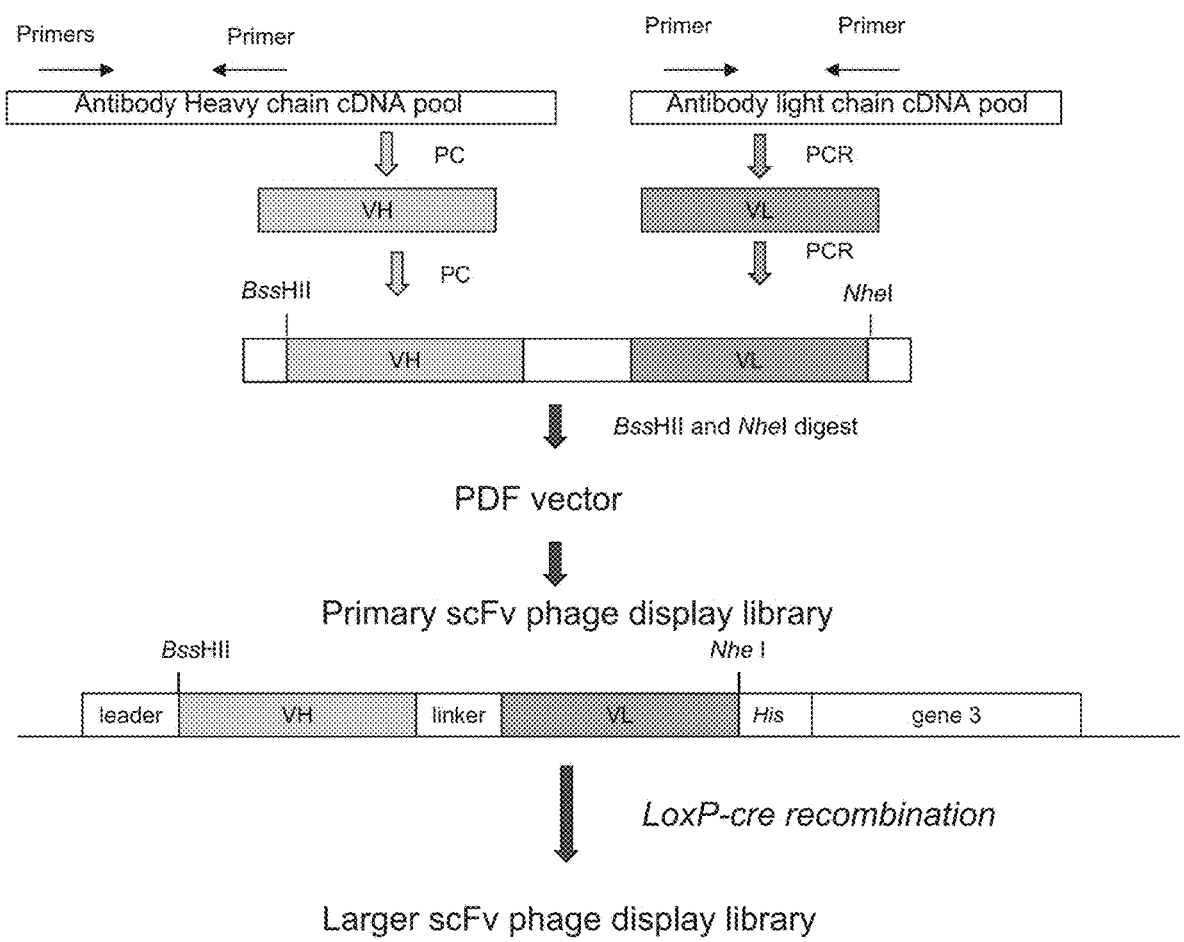
FIG. 1 is a flow chart showing PCR amplification and construction of single chain Fv (ScFv) phage display library.

In order that the present disclosure may be more readily understood, certain terms are first defined. Additional definitions are set forth throughout the detailed description.

The term "LAG-3" refers to Lymphocyte Activation Gene-3. The term "LAG-3" comprises variants, isoforms, homologs, orthologs and paralogs. For example, an antibody specific for a human LAG-3 protein may, in certain cases, cross-reacts with a LAG-3 protein from a species other than human. In other embodiments, an antibody specific for a human LAG-3 protein may be completely specific for the human LAG-3 protein and exhibit no cross-reactivity to other species or of other types, or may cross-react with LAG-3 from certain other species but not all other species (e.g., cross-react with monkey LAG-3 but not mouse LAG-3).

The term "human LAG-3" refers to human sequence of LAG-3, such as the complete amino acid sequence of human LAG-3 having Genbank Accession No. NP 002277 (SEQ ID NO: 39). The term "mouse LAG-3" refers to mouse sequence LAG-3, such as the complete amino acid sequence of mouse LAG-3 having Genbank Accession No. NP_032505. LAG-3 is also known in the art as, for example, CD223. The human LAG-3 sequence may differ from human LAG-3 of Genbank Accession No. NP 002277 by having, e.g., conserved mutations or mutations in non-conserved regions and the LAG-3 has substantially the same biological function as the human LAG-3 of Genbank Accession No. NP_002277. For example, a biological function of human LAG-3 is having an epitope in the extracellular domain of LAG-3 that is specifically bound by an antibody of the instant disclosure or a biological function of human LAG-3 is binding to MHC Class II molecules.

The term "immune response" refers to the action of, for example, lymphocytes, antigen presenting cells, phagocytic cells, granulocytes, and soluble macromolecules produced by the above cells or the liver (including antibodies, cytokines, and complement) that results in selective damage to, destruction of, or elimination from the human body of invading pathogens, cells or tissues infected with pathogens, cancerous cells, or, in cases of autoimmunity or pathological inflammation, normal human cells or tissues.

An "antigen-specific T cell response" refers to responses by a T cell that result from stimulation of the T cell with the antigen for which the T cell is specific. Non-limiting examples of responses by a T cell upon antigen-specific stimulation include proliferation and cytokine production (e.g., IL-2 production).

The term "antibody" as referred to herein includes whole antibodies and any antigen binding fragment (i.e., "antigen-binding portion") or single chains thereof. Whole antibodies are glycoproteins comprising at least two heavy (H) chains and two light (L) chains inter-connected by disulfide bonds. Each heavy chain is comprised of a heavy chain variable region (abbreviated herein as $V_H$) and a heavy chain constant region (abbreviated herein as $C_H$). The heavy chain constant region is comprised of three domains, $C_{H1}$, $C_{H2}$ and $C_{H3}$. Each light chain is comprised of a light chain variable region (abbreviated herein as $V_L$) and a light chain constant region (abbreviated herein as $C_L$). The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (C1q) of the classical complement system.

The term "antigen-binding portion" of an antibody (or simply "antibody portion"), as used herein, refers to one or more fragments of an antibody that retain the ability to specifically bind to an antigen (e.g., a LAG-3 protein). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm; (v) a bi-Fv fragment consisting of two Fc fragments, (vi) a dAb fragment (Ward et al., (1989) Nature 341:544-546), which consists of a $V_H$ domain; (vii) an isolated complementarity determining region (CDR); and (viii) a nanobody, a heavy chain variable region containing a single variable domain and two constant domains. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

An "isolated antibody", as used herein, is intended to refer to an antibody that is substantially free of other antibodies having different antigenic specificities (e.g., an isolated antibody that specifically binds a LAG-3 protein is substantially free of antibodies that specifically bind antigens other than LAG-3 proteins). An isolated antibody that specifically binds a human LAG-3 protein may, however, have cross-reactivity to other antigens, such as LAG-3 proteins from other species. Moreover, an isolated antibody can be substantially free of other cellular material and/or chemicals.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "human antibody", as used herein, is intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies of the invention can include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The term "human monoclonal antibody" refers to antibodies displaying a single binding specificity, which have variable regions in which both the framework and CDR regions are derived from human germline immunoglobulin sequences. In one embodiment, the human monoclonal antibodies are produced by a hybridoma which includes a B cell obtained from a transgenic nonhuman animal, e.g., a transgenic mouse, having a genome comprising a human heavy chain transgene and a light chain transgene fused to an immortalized cell.

The term "recombinant human antibody", as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further below), (b) antibodies isolated from a host cell transformed to express the human antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_L$ and $V_H$ regions of the recombinant antibodies are sequences that, while derived from and related to human germline $V_L$ and $V_H$ sequences, may not naturally exist within the human antibody germline repertoire in vivo.

The term "isotype" refers to the antibody class (e.g., IgM or IgG1) that is encoded by the heavy chain constant region genes.

The phrases "an antibody recognizing an antigen" and "an antibody specific for an antigen" are used interchangeably herein with the term "an antibody which binds specifically to an antigen.

The term "human antibody derivatives" refers to any modified form of the human antibody, e.g., a conjugate of the antibody and another agent or antibody.

The term "humanized antibody" is intended to refer to antibodies in which CDR sequences derived from the germline of another mammalian species, such as a mouse, have been grafted onto human framework sequences. Additional framework region modifications can be made within the human framework sequences.

The term "chimeric antibody" is intended to refer to antibodies in which the variable region sequences are derived from one species and the constant region sequences are derived from another species, such as an antibody in which the variable region sequences are derived from a mouse antibody and the constant region sequences are derived from a human antibody.

As used herein, an antibody that "specifically binds to human LAG-3" is intended to refer to an antibody that binds to human LAG-3 protein (and possibly a LAG-3 protein from one or more non-human species) but does not substantially bind to non-LAG-3 proteins. Preferably, the antibody binds to a human LAG-3 protein with "high affinity", namely with a $K_D$ of $1\times10^{-7}$ M or less, more preferably $1\times10^{-8}$ M or less, more preferably $5\times10^{-9}$ M or less, more preferably $1\times10^{-9}$ M or less.

The term "does not substantially bind" to a protein or cells, as used herein, means does not bind or does not bind with a high affinity to the protein or cells, i.e. binds to the protein or cells with a $K_D$ of $1\times10^{-6}$ M or more, more preferably $1\times10^{-5}$ M or more, more preferably $1\times10^{-4}$ M or more, more preferably $1\times10^{-3}$ M or more, even more preferably $1\times10^{-2}$ M or more.

The term "$K_{assoc}$" or "$K_a$", as used herein, is intended to refer to the association rate of a particular antibody-antigen interaction, whereas the term "$K_{dis}$" or "$K_d$," as used herein, is intended to refer to the dissociation rate of a particular antibody-antigen interaction. The term "$K_D$," as used herein, is intended to refer to the dissociation constant, which is obtained from the ratio of $K_d$ to $K_a$ (i.e., $K_d/K_a$) and is expressed as a molar concentration (M). $K_D$ values for antibodies can be determined using methods well established in the art. A preferred method for determining the $K_D$ of an antibody is by using surface plasmon resonance, preferably using a biosensor system such as a Biacore™ system.

The term "high affinity" for an IgG antibody refers to an antibody having a $K_D$ of $1\times10^{-6}$ M or less, more preferably $5\times10^{-8}$ M or less, even more preferably $1\times10^{-8}$ M or less, even more preferably $5\times10^{-9}$ M or less and even more preferably $1\times10^{-9}$ M or less for a target antigen. However, "high affinity" binding can vary for other antibody isotypes. For example, "high affinity" binding for an IgM isotype refers to an antibody having a $K_D$ of $10^{-6}$ M or less, more preferably $10^{-7}$ M or less, even more preferably $10^{-8}$ M or less.

The term "$EC_{50}$", also known as half maximal effective concentration, refers to the concentration of an antibody which induces a response halfway between the baseline and maximum after a specified exposure time.

The term "subject" includes any human or nonhuman animal. The term "nonhuman animal" includes all vertebrates, e.g., mammals and non-mammals, such as non-human primates, sheep, dogs, cats, cows, horses, chickens, amphibians, and reptiles, although mammals are preferred, such as non-human primates, sheep, dogs, cats, cows and horses.

Various aspects of the invention are described in further detail in the following subsections.

Anti-LAG-Antibodies Having Advantageous Functional Properties

Antibodies of the invention specifically bind to human LAG-3 with better binding capacity compared to previously described anti-LAG-3 antibodies, particularly compared to BMS-BMS986016.

Antibodies of the invention preferably bind to human LAG-3 protein with a $K_D$ of $1\times10^{-9}$ M or less, more preferably with a $K_D$ of $5\times10^{-10}$ M or less.

Antibodies of the invention preferably bind to human LAG-3 proteins with $EC_{50}$ of 0.2 nM or less.

Antibodies of the invention bind to the first two N-terminal domains of human LAG-3, i.e., the same domains MHC Class II binds to. The binding of LAG-3 to MHC Class II can be inhibited by antibodies of the invention. The antibodies of the invention can also block interaction of LAG-3 with LSECtin, a protein also know as CLEC4G (C-type lectin superfamily 4, member G) which was found to promote tumor progression when expressed on melanoma cells [F Xu, et al., Cancer Research. 74(13). April 2014].

Additional functional properties include cross-reactivity with LAG-3 from other species such as cynomolgus monkey and rhesus monkey. The antibodies of the invention do not substantially bind to mouse LAG-3. Preferably, an antibody of the invention binds to human LAG-3 with high affinity.

Other functional properties include the ability of the antibody to stimulate an immune response, such as an antigen-specific T cell response. This can be tested, for example, by assessing the ability of the antibody to stimulate interleukin-2 (IL-2) production in an antigen-specific T cell response. In certain embodiments, the antibody binds to human LAG-3 and stimulates an antigen-specific T cell response. In other embodiments, the antibody binds to human LAG-3 but does not stimulate an antigen-specific T cell response. Other means for evaluating the capacity of the antibody to stimulate an immune response include testing its ability to inhibit tumor growth, such as in an in vivo tumor graft model or the ability to stimulate an autoimmune response, such as the ability to promote the development of an autoimmune disease in an autoimmune model, e.g., the ability to promote the development of diabetes in the NOD mouse model. The antibodies of the invention can inhibit tumor growth, especially when administered with an anti-PD1 antibody.

Preferred antibodies of the invention are human monoclonal antibodies. Additionally or alternatively, the antibodies can be, for example, chimeric or humanized monoclonal antibodies.

Monoclonal Anti-LAG-3 Antibody

A preferred antibody of the invention is the human monoclonal antibody, anti-LAG-3 antibody 2#, structurally and chemically characterized as described below and in the following Examples. The $V_H$ amino acid sequence of anti-LAG-3 antibody 2#, is shown in SEQ ID NO: 32. The $V_L$ amino acid sequence of anti-LAG-3 antibody 2# is shown in SEQ ID NO: 34. Further, the heavy chain and light chain amino acid sequences of anti-LAG-3 antibody 2# are set forth in SEQ ID NO: 36 and SEQ ID NO: 38, respectively, and the full-length amino acid sequence of the anti-LAG-3 antibody 2# is set forth in SEQ ID NO: 30.

The $V_H$ and $V_L$ sequences (or CDR sequences) of other anti-LAG-3 antibodies which bind to human LAG-3 can be "mixed and matched" with the $V_H$ and $V_L$ sequences (or CDR sequences) of anti-LAG-3 antibody 2#. Preferably, when $V_H$ and $V_L$ chains (or the CDRs within such chains) are mixed and matched, a $V_H$ sequence from a particular $V_H/V_L$ pairing is replaced with a structurally similar $V_H$ sequence. Likewise, preferably a $V_L$ sequence from a particular $V_H/V_L$ pairing is replaced with a structurally similar $V_L$ sequence.

Accordingly, in one embodiment, an antibody of the invention, or an antigen binding portion thereof, comprises:

(a) a heavy chain variable region comprising amino acid sequence SEQ ID NO: 32 (i.e., the $V_H$ of anti-LAG-3 antibody 2#); and (b) a light chain variable region comprising amino acid sequence SEQ ID NO: 34 (i.e., the $V_L$ of anti-LAG-3 antibody 2#) or the $V_L$ of another anti-LAG3 antibody (i.e., which differs from anti-LAG-3 antibody 2#), wherein the antibody specifically binds human LAG-3.

In another embodiment, an antibody of the invention, or an antigen binding portion thereof, comprises:

(a) the CDR1, CDR2, and CDR3 regions of the heavy chain variable region comprising amino acid sequence SEQ ID NO: 32 (i.e., the CDR sequences of anti-LAG-3 antibody 2#, SEQ ID NOs:2, 4, and 6, respectively); and (b) the CDR1, CDR2, and CDR3 regions of the light chain variable region comprising amino acid sequence SEQ ID NO: 34 (i.e., the CDR sequences of anti-LAG-3 antibody 2#, SEQ ID NOs:8, 10, and 12, respectively) or the CDRs of another anti-LAG3 antibody (i.e., which differs from anti-LAG-3 antibody 2#), wherein the antibody specifically binds human LAG-3.

In yet another embodiment, the antibody, or antigen binding portion thereof, includes the heavy chain variable CDR2 region of anti-LAG-3 antibody 2# combined with CDRs of other antibodies which bind human LAG-3, e.g., CDR1 and/or CDR3 from the heavy chain variable region, and/or CDR1, CDR2, and/or CDR3 from the light chain variable region of a different anti-LAG-3 antibody.

In addition, it is well known in the art that the CDR3 domain, independently from the CDR1 and/or CDR2 domain(s), alone can determine the binding specificity of an antibody for a cognate antigen and that multiple antibodies can predictably be generated having the same binding specificity based on a common CDR3 sequence. See, e.g., Klimka et al., British J. of Cancer 83(2):252-260 (2000); Beiboer et al., J. Mol. Biol. 296:833-849 (2000); Rader et al., Proc. Natl. Acad. Sci. U.S.A. 95:8910-8915 (1998); Barbas et al., J. Am. Chem. Soc. 116:2161-2162 (1994); Barbas et al., Proc. Natl. Acad. Sci. U.S.A. 92:2529-2533 (1995); Ditzel et al., J. Immunol. 157:739-749 (1996); Berezov et al., BIA-journal 8:Scientific Review 8 (2001); Igarashi et al., J. Biochem (Tokyo) 117:452-7 (1995); Bourgeois et al., J. Virol 72:807-10 (1998); Levi et al., Proc. Natl. Acad. Sci. U.S.A. 90:4374-8 (1993); Polymenis and Stoller, J. Immunol. 152:5218-5329 (1994) and Xu and Davis, Immunity 13:37-45 (2000). See also, U.S. Pat. Nos. 6,951,646; 6,914,128; 6,090,382; 6,818,216; 6,156,313; 6,827,925; 5,833,943; 5,762,905 and 5,760,185. Each of these references is hereby incorporated by reference in its entirety.

Accordingly, in another embodiment, antibodies of the invention comprise the CDR2 of the heavy chain variable region of anti-LAG-3 antibody 2# (SEQ ID NO:4) and at least the CDR3 of the heavy and/or light chain variable region of anti-LAG-3 antibody 2# (SEQ ID NOs:6 and/or 12), or the CDR3 of the heavy and/or light chain variable region of another LAG-3 antibody, wherein the antibody is capable of specifically binding to human LAG-3. These antibodies preferably (a) compete for binding with LAG-3; (b) retain the functional characteristics; (c) bind to the same epitope; and/or (d) have a similar binding affinity as anti-LAG-3 antibody 2#. In yet another embodiment, the antibodies further may comprise the CDR2 of the light chain variable region of anti-LAG-3 antibody 2# (SEQ ID NO: 10), or the CDR2 of the light chain variable region of another LAG-3 antibody, wherein the antibody is capable of specifically binding to human LAG-3. In another embodiment, the antibodies of the invention further may include the CDR1 of the heavy and/or light chain variable region of anti-LAG-3 antibody 2# (SEQ ID NOs: 2 and/or 8), or the CDR1 of the heavy and/or light chain variable region of another LAG-3 antibody, wherein the antibody is capable of specifically binding to human LAG-3.

Conservative Modifications

In another embodiment, an antibody of the invention comprise a heavy and/or light chain variable region sequences of CDR1, CDR2 and CDR3 sequences which differ from those of anti-LAG-3 antibody 2# by one or more conservative modifications. It is understood in the art that certain conservative sequence modification can be made which do not remove antigen binding. See, e.g., Brummell et al. (1993) Biochem 32:1180-8; de Wildt et al. (1997) Prot. Eng. 10:835-41; Komissarov et al. (1997) J. Biol. Chem. 272:26864-26870; Hall et al. (1992) J. Immunol. 149:1605-12; Kelley and O'Connell (1993) Biochem. 32:6862-35; Adib-Conquy et al. (1998) Int. Immunol. 10:341-6 and Beers et al. (2000) Clin. Can. Res. 6:2835-43.

Accordingly, in one embodiment, the antibody comprises a heavy chain variable region comprising CDR1, CDR2, and CDR3 sequences and/or a light chain variable region comprising CDR1, CDR2, and CDR3 sequences, wherein:

(a) the heavy chain variable region CDR1 sequence comprises SEQ ID NO:2, and/or conservative modifications thereof; and/or (b) the heavy chain variable region CDR3 sequence comprises SEQ ID NO:6, and conservative modifications thereof; and/or (c) the light chain variable region CDR1, and/or CDR2, and/or CDR3 sequences comprise SEQ ID NO:8, and/or, SEQ ID NO:10, and/or SEQ ID NO:12, and/or conservative modifications thereof; and (d) the antibody specifically binds human LAG-3.

The antibody of the present invention possesses one or more of the following functional properties described above, such as high affinity binding to human and monkey LAG-3, lack of binding to mouse LAG-3, the ability to inhibit binding of LAG-3 to MHC Class II or LSECtin, the ability to stimulate antigen-specific T cell responses, and/or the ability to inhibit tumor growth.

In various embodiments, the antibody can be, for example, a human, humanized or chimeric antibody.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of the invention can be replaced with other amino acid residues from the same side chain family and the altered antibody can be tested for retained function (i.e., the functions set forth above) using the functional assays described herein.

Engineered and Modified Antibodies

Antibodies of the invention can be prepared using an antibody having one or more of the $V_H$/$V_L$ sequences of anti-LAG-3 antibody 2# as starting material to engineer a modified antibody. An antibody can be engineered by modifying one or more residues within one or both variable regions (i.e., $V_H$ and/or $V_L$), for example within one or more CDR regions and/or within one or more framework regions. Additionally or alternatively, an antibody can be engineered by modifying residues within the constant region(s), for example to alter the effector function(s) of the antibody.

In certain embodiments, CDR grafting can be used to engineer variable regions of antibodies. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann et al. (1998) Nature 332:323-327; Jones et al. (1986) Nature 321:522-525; Queen et al. (1989) Proc. Natl. Acad. See. U.S.A. 86:10029-10033; U.S. Pat. Nos. 5,225,539; 5,530,101; 5,585,089; 5,693,762 and 6,180,370).

Accordingly, another embodiment of the invention pertains to an isolated monoclonal antibody, or antigen binding portion thereof, comprising a heavy chain variable region comprising CDR1, CDR2, and CDR3 sequences comprising SEQ ID NOs: 2, 4, 6, respectively, and/or a light chain variable region comprising CDR1, CDR2, and CDR3 sequences comprising SEQ ID NOs: 8, 10, 12, respectively. While these antibodies contain the $V_H$ and $V_L$ CDR sequences of monoclonal antibody 2#, they can contain different framework sequences.

Such framework sequences can be obtained from public DNA databases or published references that include germline antibody gene sequences. For example, germline DNA sequences for human heavy and light chain variable region genes can be found in the "VBase" human germline sequence database (available on the Internet at www.mrc-cpe.cam.ac.uk/vbase), as well as in Kabat et al. (1991), cited supra; Tomlinson et al. (1992) "The Repertoire of Human Germline $V_H$ Sequences Reveals about Fifty Groups of $V_H$ Segments with Different Hypervariable Loops" J. Mol. Biol. 227:776-798; and Cox et al. (1994) "A Directory of Human Germ-line $V_H$ Segments Reveals a Strong Bias in their Usage" Eur. J. Immunol. 24:827-836; the contents of each of which are expressly incorporated herein by reference. As another example, the germline DNA sequences for human heavy and light chain variable region genes can be found in the Genbank database. For example, the following heavy chain germline sequences found in the HCo7 HuMAb mouse are available in the accompanying Genbank Accession Nos.: 1-69 (N_0010109, NT_024637 & BC070333), 3-33 (NG_0010109 & NT_024637) and 3-7 (NG_0010109 & NT_024637). As another example, the following heavy chain germline sequences found in the HCo12 HuMAb mouse are available in the accompanying Genbank Accession Nos.: 1-69 (NG_0010109, NT_024637 & BC070333), 5-51 (NG_0010109 & NT_024637), 4-34 (NG_0010109 & NT_024637), 3-30.3 (CAJ556644) & 3-23 (AJ406678).

Antibody protein sequences are compared against a compiled protein sequence database using one of the sequence similarity searching methods called the Gapped BLAST (Altschul et al. (1997), supra), which is well known to those skilled in the art.

Preferred framework sequences for use in the antibodies of the invention are those that are structurally similar to the framework sequences used by antibodies of the invention, e.g., the four framework regions in the heavy chain variable region having the amino acid sequences of SEQ ID NOs: 14, 16, 18 and 20, and the four framework regions in the light chain variable region having the amino acid sequences of SEQ ID NOs:22, 24, 26 and 28. The $V_H$ CDR1, CDR2, and CDR3 sequences can be grafted onto framework regions that have the identical sequence as that found in the germline immunoglobulin gene from which the framework sequence derive, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370).

Another type of variable region modification is to mutate amino acid residues within the $V_H$ and/or $V_L$ CDR1, CDR2 and/or CDR3 regions to thereby improve one or more binding properties (e.g., affinity) of the antibody of interest. Site-directed mutagenesis or PCR-mediated mutagenesis can be performed to introduce the mutation(s) and the effect on antibody binding, or other functional property of interest, can be evaluated in in vitro or in vivo assays as described herein and provided in the Examples. Preferably conservative modifications (as known in the art) are introduced. The mutations can be amino acid substitutions, additions or deletions, but are preferably substitutions. Moreover, typically no more than one, two, three, four or five residues within a CDR region are altered.

Accordingly, in another embodiment, the invention provides isolated anti-LAG-3 monoclonal antibodies, or antigen binding portions thereof, comprising a heavy chain variable region comprising: (a) a $V_H$ CDR1 region comprising SEQ ID NO: 2, or an amino acid sequence having one, two, three, four or five amino acid substitutions, deletions or additions as compared to SEQ ID NO: 2; (b) a $V_H$ CDR2 region comprising SEQ ID NO:4, or an amino acid sequence having one, two, three, four or five amino acid substitutions, deletions or additions as compared to SEQ ID NO:4; (c) a $V_H$ CDR3 region comprising SEQ ID NO:6, or an amino acid sequence having one, two, three, four or five amino acid substitutions, deletions or additions as compared to SEQ ID NO:6; (d) a $V_L$ CDR1 region comprising SEQ ID NO:8, or an amino acid sequence having one, two, three, four or five amino acid substitutions, deletions or additions as compared to SEQ ID NO:8; (e) a $V_L$ CDR2 region comprising SEQ ID NO:10, or an amino acid sequence having one, two, three, four or five amino acid substitutions, deletions or additions as compared to SEQ ID NO:10; and (f) a $V_L$ CDR3 region comprising SEQ ID NO:12, or an amino acid sequence having one, two, three, four or five amino acid substitutions, deletions or additions as compared to SEQ ID NO:12.

Engineered antibodies of the invention include those in which modifications have been made to framework residues within $V_H$ and/or $V_L$, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation can contain framework residues that differ from the germline sequence from which the antibody is derived. Such residues can be identified by comparing the antibody framework sequences to the germline sequences from which the antibody is derived.

Another type of framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. Patent Publication No. 20030153043.

In addition or as an alternative to modifications made within the framework or CDR regions, antibodies of the invention can be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the invention can be chemically modified (e.g., one or more chemical moieties can be attached to the antibody) or be modified to alter its glycosylation, again to alter one or more functional properties of the antibody. Each of these embodiments is described in further detail below. The numbering of residues in the Fc region is that of the EU index of Kabat.

In a preferred embodiment, the antibody is an IgG4 isotype antibody comprising a Serine to Proline mutation at a position corresponding to position 241 as described in Angal et al. (1993) Mol. Immunol. 30:105-108 in the hinge region of the heavy chain constant region. This mutation has been reported to abolish the heterogeneity of inter-heavy chain disulfide bridges in the hinge region (Angal et al. supra; position 241 is based on the Kabat numbering system).

In one embodiment, the hinge region of CH1 is modified such that the number of cysteine residues in the hinge region is altered, e.g., increased or decreased. This approach is described further in U.S. Pat. No. 5,677,425. The number of cysteine residues in the hinge region of CH1 is altered to, for example, facilitate assembly of the light and heavy chains or to increase or decrease the stability of the antibody.

In another embodiment, the Fc hinge region of an antibody is mutated to decrease the biological half-life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745. In still another embodiment, the glycosylation of an antibody is modified. For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. See, e.g., U.S. Pat. Nos. 5,714,350 and 6,350,861.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. For example, the cell lines Ms704, Ms705, and Ms709 lack the fucosyltransferase gene, FUT8 (α(1,6)-fucosyltransferase), such that antibodies expressed in the Ms704, Ms705, and Ms709 cell lines lack fucose on their carbohydrates. The Ms704, Ms705, and Ms709 FUT8$^{-/-}$ cell lines were created by the targeted disruption of the FUT8 gene in CHO/DG44 cells using two replacement vectors (see U.S. Patent Publication No. 20040110704 and Yamane-Ohnuki et al. (2004) Biotechnol Bioeng 87:614-22). As another example, EP 1,176,195 describes a cell line with a functionally disrupted FUT8 gene, which encodes a fucosyl transferase, such that antibodies expressed in such a cell line exhibit hypofucosylation by reducing or eliminating the α-1,6 bond-related enzyme. EP 1,176,195 also describes cell lines which have a low enzyme activity for adding fucose to the N-acetylglucosamine that binds to the Fc region of the antibody or does not have the enzyme activity, for example the rat myeloma cell line YB2/0 (ATCC CRL 1662). PCT Publication WO 03/035835 describes a variant CHO cell line, Lec13 cells, with reduced ability to attach fucose to Asn(297)-linked carbohydrates, also resulting in hypofucosylation of antibodies expressed in that host cell (see also Shields et al. (2002) J. Biol. Chem. 277:26733-26740). Antibodies with a modified glycosylation profile can also be produced in chicken eggs, as described in PCT Publication WO 06/089231. Alternatively, antibodies with a modified glycosylation profile can be produced in plant cells, such as Lemna. Methods for production of antibodies in a plant system are disclosed in the U.S. patent application corresponding to Alston & Bird LLP, filed on Aug. 11, 2006. PCT Publication WO 99/54342 describes cell lines engineered to express glycoprotein-modifying glycosyl transferases (e.g., β(1,4)-N-acetylglucosaminyltransferase III (GnTIII)) such that antibodies expressed in the engineered cell lines exhibit increased bisecting GlcNac structures which results in increased ADCC activity of the antibodies (see also Umana et al. (1999) Nat. Biotech. 17:176-180). Alternatively, the fucose residues of the antibody can be cleaved off using a fucosidase enzyme; e.g., the fucosidase α-L-fucosidase removes fucosyl residues from antibodies (Tarentino et al. (1975) Biochem. 14:5516-23).

Another modification of the antibodies herein that is contemplated by this disclosure is pegylation. An antibody can be pegylated to, for example, increase the biological (e.g., serum) half-life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of the invention. See, e.g., EPO 154 316 and EP 0 401 384.

Antibody Physical Properties

Antibodies of the invention can be characterized by their various physical properties, to detect and/or differentiate different classes thereof.

For example, antibodies can contain one or more glycosylation sites in either the light or heavy chain variable region. Such glycosylation sites may result in increased immunogenicity of the antibody or an alteration of the pK of the antibody due to altered antigen binding (Marshall et al (1972) Annu Rev Biochem 41:673-702; Gala and Morrison (2004) J Immunol 172:5489-94; Wallick et al (1988) J Exp Med 168:1099-109; Spiro (2002) Glycobiology 12:43R-56R; Parekh et al (1985) Nature 316:452-7; Mimura et al. (2000) Mol Immunol 37:697-706). Glycosylation has been known to occur at motifs containing an N-X-S/T sequence. In some instances, it is preferred to have an anti-LAG-3 antibody that does not contain variable region glycosylation. This can be achieved either by selecting antibodies that do not contain the glycosylation motif in the variable region or by mutating residues within the glycosylation region.

In a preferred embodiment, the antibodies do not contain asparagine isomerism sites. The deamidation of asparagine may occur on N-G or D-G sequences and result in the creation of an isoaspartic acid residue that introduces a kink into the polypeptide chain and decreases its stability (isoaspartic acid effect).

Each antibody will have a unique isoelectric point (pI), which generally falls in the pH range between 6 and 9.5. The pI for an IgG1 antibody typically falls within the pH range of 7-9.5 and the pI for an IgG4 antibody typically falls within the pH range of 6-8. There is speculation that antibodies with a pI outside the normal range may have some unfolding and instability under in vivo conditions. Thus, it is preferred to have an anti-LAG-3 antibody that contains a pI value that falls in the normal range. This can be achieved either by selecting antibodies with a pI in the normal range or by mutating charged surface residues.

Nucleic Acid Molecules Encoding Antibodies of the Invention

In another aspect, the invention provides nucleic acid molecules that encode heavy and/or light chain variable regions, or CDRs, of the antibodies of the invention. The nucleic acids can be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques. A nucleic acid of the invention can be, e.g., DNA or RNA and may or may not contain intronic sequences. In a preferred embodiment, the nucleic acid is a cDNA molecule.

Nucleic acids of the invention can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), a nucleic acid encoding such antibodies can be recovered from the gene library.

Preferred nucleic acids molecules of the invention include those encoding the $V_H$ and $V_L$ (SEQ ID NOs:31 and 33, respectively) or the CDRs (SEQ ID Nos: 1, 3, 5, 7, 9 and 11, respectivelt) sequences of LAG-3 monoclonal antibody. Once DNA fragments encoding $V_H$ and $V_L$ segments are obtained, these DNA fragments can be further manipulated by standard recombinant DNA techniques, for example to convert the variable region genes to full-length antibody chain genes, to Fab fragment genes or to a scFv gene. In these manipulations, a $V_L$- or $V_H$-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the $V_H$ region can be converted to a full-length heavy chain gene by operatively linking the $V_H$-encoding DNA to another DNA molecule encoding heavy chain constant regions ($C_{H1}$, $C_{H2}$ and $C_{H3}$). The sequences of human heavy chain constant region genes are known in the art (see e.g., Kabat et al. (1991), supra) and DNA fragments encompassing these regions can be obtained by standard PCR amplification. The heavy chain constant region can be an IgG, IgG2, IgG3, IgG4, IgA, IgE, IgM or IgD constant region, but most preferably is an IgG1 or IgG4 constant region. For a Fab fragment heavy chain gene, the $V_H$-encoding DNA can be operatively linked to another DNA molecule encoding only the heavy chain $C_{H1}$ constant region.

The isolated DNA encoding the $V_L$ region can be converted to a full-length light chain gene (as well as a Fab light chain gene) by operatively linking the $V_L$-encoding DNA to another DNA molecule encoding the light chain constant region, $C_L$. The sequences of human light chain constant region genes are known in the art (see e.g., Kabat et al., supra) and DNA fragments encompassing these regions can be obtained by standard PCR amplification. In preferred embodiments, the light chain constant region can be a kappa or lambda constant region.

To create a scFv gene, the $V_H$- and $V_L$-encoding DNA fragments are operatively linked to another fragment encoding a flexible linker, e.g., encoding the amino acid sequence $(Gly_4\text{-}Ser)_3$, such that the $V_H$ and $V_L$ sequences can be expressed as a contiguous single-chain protein, with the $V_L$ and $V_H$ regions joined by the flexible linker (see e.g., Bird et al. (1988) Science 242:423-426; Huston et al. (1988) Proc. Natl. Acad. Sci. USA 85:5879-5883; McCafferty et al., (1990) Nature 348:552-554).

Production of Monoclonal Antibodies of the Invention

Monoclonal antibodies (mAbs) of the present invention can be produced using the well-known somatic cell hybridization (hybridoma) technique of Kohler and Milstein (1975) Nature 256: 495. Other embodiments for producing monoclonal antibodies include viral or oncogenic transformation of B lymphocytes and phage display techniques. Chimeric or humanized antibodies are also well known in the art. See e.g., U.S. Pat. Nos. 4,816,567; 5,225,539; 5,530,101; 5,585,089; 5,693,762 and 6,180,370, the contents of which are specifically incorporated herein by reference in their entirety.

In a preferred embodiment, the antibodies of the invention are human monoclonal antibodies. Such human monoclonal antibodies directed against human LAG-3 can be generated using transgenic or transchromosomic mice carrying parts of the human immune system rather than the mouse system. These transgenic and transchromosomic mice include mice referred to herein as the HuMAb Mouse™ and KM Mouse™, respectively, and are collectively referred to herein as "human Ig mice."

The HuMAb Mouse™ (Medarex™, Inc.) contains human immunoglobulin gene miniloci that encode unrearranged human heavy (μ and γ) and κ light chain immunoglobulin sequences, together with targeted mutations that inactivate the endogenous μ and κ chain loci (see e.g., Lonberg et al. (1994) Nature 368(6474): 856-859). Accordingly, the mice exhibit reduced expression of mouse IgM or κ, and in response to immunization, the introduced human heavy and light chain transgenes undergo class switching and somatic mutation to generate high affinity human IgGκ monoclonal antibodies (Lonberg et al. (1994), supra; reviewed in Lonberg (1994) Handbook of Experimental Pharmacology 113: 49-101; Lonberg, N. and Huszar, D. (1995) Intern. Rev. Immunol. 13: 65-93, and Harding and Lonberg (1995) Ann. N.Y. Acad. Sci. 764:536-546). Preparation and use of the HuMAb Mouse™, and the genomic modifications carried by such mice, is further described in Taylor et al. (1992) Nucleic Acids Research 20:6287-6295; Chen et al. (1993) International Immunology 5: 647-656; Tuaillon et al. (1993) Proc. Natl. Acad. Sci. USA 90:3720-3724; Choi et al. (1993) Nature Genetics 4:117-123; Chen et al. (1993) EMBO J. 12: 821-830; Tuaillon et al. (1994) J. Immunol. 152:2912-2920; Taylor et al. (1994) International Immunology 6: 579-591; and Fishwild et al. (1996) Nature Biotechnology 14: 845-851, the contents of all of which are hereby specifically incorporated by reference in their entirety. See further, U.S. Pat. Nos. 5,545,806; 5,569,825; 5,625,126; 5,633,425; 5,789,650; 5,877,397; 5,661,016; 5,814,318; 5,874,299; 5,770,429; and 5,545,807; PCT Publication Nos. WO 92/03918; WO 93/12227; WO 94/25585; WO 97/13852; WO 98/24884; WO 99/45962 and WO 01/14424, the contents of which are incorporated herein by reference in their entirety.

In another embodiment, human antibodies of the invention can be raised using a mouse that carries human immunoglobulin sequences on transgenes and transchomosomes, such as a mouse that carries a human heavy chain transgene and a human light chain transchromosome. This mouse is referred to herein as a "KM Mouse™," and is described in detail in PCT Publication WO 02/43478. A modified form of this mouse, which further comprises a homozygous disruption of the endogenous FcγRIIB receptor gene, is also described in PCT Publication WO 02/43478 and referred to herein as a "KM/FCGR2D mouse." In addition, mice with either the HCo7 or HCo12 heavy chain transgenes or both can be used.

Additional transgenic animal embodiments include the Xenomouse (Abgenix, Inc., U.S. Pat. Nos. 5,939,598; 6,075,181; 6,114,598; 6,150,584 and 6,162,963). Further embodiments include "TC mice" (Tomizuka et al. (2000) Proc. Natl. Acad. Sci. USA 97:722-727) and cows carrying human heavy and light chain transchromosomes (Kuroiwa et al. (2002) Nature Biotechnology 20:889-894; PCT Publication WO 02/092812). The contents of these patents and publications are specifically incorporated herein by reference in their entirety.

In one embodiment, human monoclonal antibodies of the invention are prepared using phage display methods for screening libraries of human immunoglobulin genes. See, e.g. U.S. Pat. Nos. 5,223,409; 5,403,484; 5,571,698; 5,427,908; 5,580,717; 5,969,108; 6,172,197; 5,885,793; 6,521,404; 6,544,731; 6,555,313; 6,582,915; and 6,593,081, the contents of which are incorporated herein by reference in their entirety.

Human monoclonal antibodies of the invention can also be prepared using SCID mice into which human immune cells have been reconstituted such that a human antibody response can be generated upon immunization. See, e.g., U.S. Pat. Nos. 5,476,996 and 5,698,767, the contents of which are incorporated herein by reference in their entirety.

In another embodiment, human anti-LAG-3 antibodies are prepared using phage display where the phages comprise nucleic acids encoding antibodies generated in transgenic animals previously immunized with LAG-3. In a preferred embodiment, the transgenic animal is a HuMab, KM, or Kirin mouse. See, e.g. U.S. Pat. No. 6,794,132, the contents of which are incorporated herein by reference in its entirety.

Immunization of Human Ig Mice

In one embodiment of the invention, human Ig mice are immunized with a purified or enriched preparation of a LAG-3 antigen, recombinant LAG-3 protein, or cells expressing a LAG-3 protein. See, e.g., Lonberg et al. (1994), supra; Fishwild et al. (1996), supra; PCT Publications WO 98/24884 or WO 01/14424, the contents of which are incorporated herein by reference in their entirety. In a preferred embodiment, 6-16 week old mice are immunized with 5-50 µg of LAG-3 protein. Alternatively, a portion of LAG-3 fused to a non-LAG-3 polypeptide is used.

In one embodiment, the transgenic mice are immunized intraperitoneally (IP) or intravenously (IV) with LAG-3 antigen in complete Freund's adjuvant, followed by subsequent IP or IV immunizations with antigen in incomplete Freund's adjuvant. In other embodiments, adjuvants other than Freund's or whole cells in the absence of adjuvant are used. The plasma can be screened by ELISA and cells from mice with sufficient titers of anti-LAG-3 human immunoglobulin can be used for fusions.

Generation of Hybridomas Producing Human Monoclonal Antibodies of the Invention

To generate hybridomas producing human monoclonal antibodies of the invention, splenocytes and/or lymph node cells from immunized mice can be isolated and fused to an appropriate immortalized cell line, such as a mouse myeloma cell line. The resulting hybridomas can be screened for the production of antigen-specific antibodies. Generation of hybridomas is well-known in the art. See, e.g., Harlow and Lane (1988) Antibodies, A Laboratory Manual, Cold Spring Harbor Publications, New York.

Generation of Transfectomas Producing Monoclonal Antibodies of the Invention

Antibodies of the invention also can be produced in a host cell transfectoma using, for example, a combination of recombinant DNA techniques and gene transfection methods as is well known in the art (e.g., Morrison, S. (1985) Science 229:1202). In one embodiment, DNA encoding partial or full-length light and heavy chains obtained by standard molecular biology techniques is inserted into one or more expression vectors such that the genes are operatively linked to transcriptional and translational regulatory sequences. In this context, the term "operatively linked" is intended to mean that an antibody gene is ligated into a vector such that transcriptional and translational control sequences within the vector serve their intended function of regulating the transcription and translation of the antibody gene.

The term "regulatory sequence" is intended to include promoters, enhancers and other expression control elements (e.g., polyadenylation signals) that control the transcription or translation of the antibody chain genes. Such regulatory sequences are described, e.g., in Goeddel (Gene Expression Technology. Methods in Enzymology 185, Academic Press, San Diego, Calif. (1990)). Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP) and polyoma. Alternatively, nonviral regulatory sequences can be used, such as the ubiquitin promoter or β-globin promoter. Still further, regulatory elements composed of sequences from different sources, such as the SRα promoter system, which contains sequences from the SV40 early promoter and the long terminal repeat of human T cell leukemia virus type 1 (Takebe et al. (1988) Mol. Cell. Biol. 8:466-472). The expression vector and expression control sequences are chosen to be compatible with the expression host cell used.

The antibody light chain gene and the antibody heavy chain gene can be inserted into the same or separate expression vectors. In preferred embodiments, the variable regions are used to create full-length antibody genes of any antibody isotype by inserting them into expression vectors already encoding heavy chain constant and light chain constant regions of the desired isotype such that the $V_H$ segment is operatively linked to the $C_H$ segment(s) within the vector and the $V_L$ segment is operatively linked to the $C_L$ segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes and regulatory sequences, the recombinant expression vectors of the invention can carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216; 4,634,665 and 5,179,017). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the invention in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody.

Preferred mammalian host cells for expressing the recombinant antibodies of the invention include Chinese Hamster Ovary (CHO cells) (including dhfr⁻ CHO cells, described in Urlaub and Chasin, (1980) Proc. Natl. Acad. Sci. USA 77:4216-4220, used with a DHFR selectable marker, e.g., as described in R. J. Kaufman and P. A. Sharp (1982) J. Mol. Biol. 159:601-621), NSO myeloma cells, COS cells and SP2 cells. In particular, for use with NSO myeloma cells, another preferred expression system is the GS gene expression system disclosed in WO 87/04462, WO 89/01036 and EP 338,841. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Immunoconjugates

Antibodies of the invention can be conjugated to a therapeutic agent to form an immunoconjugate such as an antibody-drug conjugate (ADC). Suitable therapeutic agents include antimetabolites, alkylating agents, DNA minor groove binders, DNA intercalators, DNA crosslinkers, histone deacetylase inhibitors, nuclear export inhibitors, proteasome inhibitors, topoisomerase I or II inhibitors, heat shock protein inhibitors, tyrosine kinase inhibitors, antibiotics, and anti-mitotic agents. In the ADC, the antibody and therapeutic agent preferably are conjugated via a linker cleavable such as a peptidyl, disulfide, or hydrazone linker. More preferably, the linker is a peptidyl linker such as Val-Cit, Ala-Val, Val-Ala-Val, Lys-Lys, Pro-Val-Gly-Val-Val, Ala-Asn-Val, Val-Leu-Lys, Ala-Ala-Asn, Cit-Cit, Val-Lys, Lys, Cit, Ser, or Glu. The ADCs can be prepared as described in U.S. Pat. Nos. 7,087,600; 6,989,452; and 7,129,261; PCT Publications WO 02/096910; WO 07/038,658; WO 07/051,081; WO 07/059,404; WO 08/083,312; and WO 08/103,693; U.S. Patent Publications 20060024317; 20060004081; and 20060247295; the disclosures of which are incorporated herein by reference.

Bispecific Molecules

In another aspect, the present disclosure features bispecific molecules comprising one or more antibodies of the invention linked to at least one other functional molecule, e.g., another peptide or protein (e.g., another antibody or ligand for a receptor) to generate a bispecific molecule that binds to at least two different binding sites or target molecules, such as a bispecific molecule that binds to LAG-3 and TIM3, or alternatively LAG-3 and PD1, or LAG-3 and PD-L1. Thus, as used herein, "bispecific molecule" includes molecules that have three or more specificities.

In an embodiment, a bispecific molecule has, in addition to an anti-Fc binding specificity and an anti-LAG-3 binding specificity, a third specificity. The third specificity can be for an anti-enhancement factor (EF), e.g., a molecule that binds to a surface protein involved in cytotoxic activity and thereby increases the immune response against the target cell. For example, the anti-enhancement factor can bind a cytotoxic T-cell (e.g. via CD2, CD3, CD8, CD28, CD4, CD40, or ICAM-1) or other immune cell, resulting in an increased immune response against the target cell.

Bispecific molecules can come in many different formats and sizes. At one end of the size spectrum, a bispecific molecule retains the traditional antibody format, except that, instead of having two binding arms of identical specificity, it has two binding arms each having a different specificity. At the other extreme are bispecific molecules consisting of two single-chain antibody fragments (scFv's) linked by a peptide chain, a so-called Bs(scFv)$_2$ construct. Intermediate-sized bispecific molecules include two different F(ab) fragments linked by a peptidyl linker. Bispecific molecules of these and other formats can be prepared by genetic engineering, somatic hybridization, or chemical methods. See, e.g., Kufer et al, cited supra; Cao and Suresh, Bioconjugate Chemistry, 9 (6), 635-644 (1998); and van Spriel et al., Immunology Today, 21 (8), 391-397 (2000), and the references cited therein.

Pharmaceutical Compositions

In another aspect, the present disclosure provides a pharmaceutical composition comprising one or more antibodies of the present invention formulated together with a pharmaceutically acceptable carrier. The composition may optionally contain one or more additional pharmaceutically active ingredients, such as another antibody or a drug. The pharmaceutical compositions of the invention also can be administered in a combination therapy with, for example, another immunostimulatory agent, anti-cancer agent, an anti-viral agent, or a vaccine, such that the anti-LAG-3 antibody enhances the immune response against the vaccine.

The pharmaceutical composition can comprise any number of excipients. Excipients that can be used include carriers, surface active agents, thickening or emulsifying agents, solid binders, dispersion or suspension aids, solubilizers, colorants, flavoring agents, coatings, disintegrating agents, lubricants, sweeteners, preservatives, isotonic agents, and combinations thereof. The selection and use of suitable excipients is taught in Gennaro, ed., Remington: The Science and Practice of Pharmacy, 20th Ed. (Lippincott Williams & Wilkins 2003), the disclosure of which is incorporated herein by reference.

Preferably, the pharmaceutical composition is suitable for intravenous, intramuscular, subcutaneous, parenteral, spinal or epidermal administration (e.g., by injection or infusion). Depending on the route of administration, the active compound can be coated in a material to protect it from the action of acids and other natural conditions that may inactivate it. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, an antibody of the invention can be administered via a non-parenteral route, such as a topical, epidermal or mucosal route of administration, e.g., intranasally, orally, vaginally, rectally, sublingually or topically.

Pharmaceutical compositions can be in the form of sterile aqueous solutions or dispersions. They can also be formulated in a microemulsion, liposome, or other ordered structure suitable to high drug concentration.

The amount of active ingredient which can be combined with a carrier material to produce a single dosage form will vary depending upon the subject being treated and the particular mode of administration and will generally be that amount of the composition which produces a therapeutic effect. Generally, out of one hundred percent, this amount will range from about 0.01% to about ninety-nine percent of active ingredient, preferably from about 0.1% to about 70%, most preferably from about 1% to about 30% of active ingredient in combination with a pharmaceutically acceptable carrier.

Dosage regimens are adjusted to provide the optimum desired response (e.g., a therapeutic response). For example, a single bolus can be administered, several divided doses can be administered over time or the dose can be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. Alternatively, antibody can be administered as a sustained release formulation, in which case less frequent administration is required.

For administration of the antibody, the dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months. Preferred dosage regimens for an anti-LAG-3 antibody of the invention include 1 mg/kg body weight or 3 mg/kg body weight via intravenous administration, with the antibody being given using one of the following dosing schedules: (i) every four weeks for six dosages, then every three months; (ii) every three weeks; (iii) 3 mg/kg body weight once followed by 1 mg/kg body weight every three weeks. In some methods, dosage is adjusted to achieve a plasma antibody concentration of about 1-1000 µg/ml and in some methods about 25-300 µg/ml.

A "therapeutically effective dosage" of an anti-LAG-3 antibody of the invention preferably results in a decrease in severity of disease symptoms, an increase in frequency and duration of disease symptom-free periods, or a prevention of impairment or disability due to the disease affliction. For example, for the treatment of tumor-bearing subjects, a "therapeutically effective dosage" preferably inhibits tumor growth by at least about 20%, more preferably by at least about 40%, even more preferably by at least about 60%, and still more preferably by at least about 80% relative to untreated subjects. A therapeutically effective amount of a therapeutic compound can decrease tumor size, or otherwise ameliorate symptoms in a subject, which is typically a human or can be another mammal.

The pharmaceutical composition can be a controlled release formulation, including implants, transdermal patches, and microencapsulated delivery systems. Biodegradable, biocompatible polymers can be used, such as ethylene vinyl acetate, polyanhydrides, polyglycolic acid, colLAGen, polyorthoesters, and polylactic acid. See, e.g., Sustained and Controlled Release Drug Delivery Systems, J. R. Robinson, ed., Marcel Dekker, Inc., New York, 1978.

Therapeutic compositions can be administered via medical devices such as (1) needleless hypodermic injection devices (e.g., U.S. Pat. Nos. 5,399,163; 5,383,851; 5,312,335; 5,064,413; 4,941,880; 4,790,824; and 4,596,556); (2) micro-infusion pumps (U.S. Pat. No. 4,487,603); (3) transdermal devices (U.S. Pat. No. 4,486,194); (4) infusion apparati (U.S. Pat. Nos. 4,447,233 and 4,447,224); and (5) osmotic devices (U.S. Pat. Nos. 4,439,196 and 4,475,196); the disclosures of which are incorporated herein by reference.

In certain embodiments, the human monoclonal antibodies of the invention can be formulated to ensure proper distribution in vivo. For example, to ensure that the therapeutic antibodies of the invention cross the blood-brain barrier, they can be formulated in liposomes, which may additionally comprise targeting moieties to enhance selective transport to specific cells or organs. See, e.g. U.S. Pat. Nos. 4,522,811; 5,374,548; 5,416,016; and 5,399,331; V. V. Ranade (1989) J. Clin. Pharmacol. 29:685; Umezawa et al., (1988) Biochem. Biophys. Res. Commun. 153:1038; Bloeman et al. (1995) FEBS Lett. 357:140; M. Owais et al. (1995) Antimicrob. Agents Chemother. 39:180; Briscoe et al. (1995) Am. J. Physiol. 1233:134; Schreier et al. (1994) J. Biol. Chem. 269:9090; Keinanen and Laukkanen (1994) FEBS Lett. 346:123; and Killion and Fidler (1994) Immunomethods 4:273.

Uses and Methods of the Invention

Antibodies (compositions, bispecifics, and immunoconjugates) of the present invention have numerous in vitro and in vivo utilities involving, for example, detection of LAG-3 or enhancement of immune responses by blockade of LAG-3. In a preferred embodiment, the antibodies are human antibodies. Such antibodies can be administered to cells in culture, in vitro or ex vivo, or to human subjects, e.g., in vivo, to enhance immunity in a variety of situations. Accordingly, in one aspect, the invention provides a method of modifying an immune response in a subject comprising administering to the subject the antibody, or antigen-binding portion thereof, of the invention such that the immune response in the subject is modified. Preferably, the response is enhanced, stimulated or up-regulated.

Preferred subjects include human patients in need of enhancement of an immune response. The methods are particularly suitable for treating human patients having a disorder that can be treated by augmenting an immune response (e.g., the T-cell mediated immune response). In a particular embodiment, the methods are particularly suitable for treatment of cancer in vivo. To achieve antigen-specific enhancement of immunity, the anti-LAG-3 antibodies can be administered together with an antigen of interest or the antigen may already be present in the subject to be treated (e.g., a tumor-bearing or virus-bearing subject). When antibodies to LAG-3 are administered together with another agent, the two can be administered in either order or simultaneously.

The invention further provides methods for detecting the presence of human LAG-3 antigen in a sample, or measuring the amount of human LAG-3 antigen, comprising contacting the sample, and a control sample, with a human monoclonal antibody, or an antigen binding portion thereof, which specifically binds to human LAG-3, under conditions that allow for formation of a complex between the antibody or portion thereof and human LAG-3. The formation of a complex is then detected, wherein a difference complex formation between the sample compared to the control sample is indicative the presence of human LAG-3 antigen in the sample. Moreover, the anti-LAG-3 antibodies of the invention can be used to purify human LAG-3 via immunoaffinity purification.

Given the ability of anti-LAG-3 antibodies of the invention to inhibit the binding of LAG-3 to MHC Class II/LSECtin and to stimulate antigen-specific T cell responses, the invention also provides in vitro and in vivo methods of using the antibodies to stimulate, enhance or upregulate antigen-specific T cell responses. For example, the invention provides a method of stimulating an antigen-specific T cell response comprising contacting said T cell with an antibody of the invention, such that an antigen-specific T cell response is stimulated. Any suitable indicator of an antigen-specific T cell response can be used to measure the antigen-specific T cell response.

Non-limiting examples of such suitable indicators include increased T cell proliferation in the presence of the antibody and/or increase cytokine production in the presence of the antibody. In a preferred embodiment, interleukin-2 production by the antigen-specific T cell is stimulated.

The invention also provides method for stimulating an immune response (e.g., an antigen-specific T cell response) in a subject comprising administering an antibody of the invention to the subject such that an immune response (e.g., an antigen-specific T cell response) in the subject is stimulated. In a preferred embodiment, the subject is a tumor-bearing subject and an immune response against the tumor is stimulated. In another preferred embodiment, the subject is a virus-bearing subject and an immune response against the virus is stimulated.

In another embodiment, the invention provides methods for inhibiting growth of tumor cells in a subject comprising administering to the subject an antibody of the invention such that growth of the tumor is inhibited in the subject. In yet another embodiment, the invention provides methods for treating a viral infection in a subject comprising administering to the subject an antibody of the invention such that the viral infection is treated in the subject.

These and other methods of the invention are discussed in further detail below.

Cancer

Blockade of LAG-3 by antibodies can enhance the immune response to cancerous cells in the patient. In one aspect, the present invention relates to treatment of a subject in vivo using an anti-LAG-3 antibody such that growth of cancerous tumors is inhibited. An anti-LAG-3 antibody can be used alone to inhibit the growth of cancerous tumors. Alternatively, an anti-LAG-3 antibody can be used in conjunction with other immunogenic agents, standard cancer treatments, or other antibodies, as described below.

Accordingly, in one embodiment, the invention provides a method of inhibiting growth of tumor cells in a subject, comprising administering to the subject a therapeutically effective amount of an anti-LAG-3 antibody, or antigen-binding portion thereof. Preferably, the antibody is a human anti-LAG-3 antibody (such as any of the human anti-human LAG-3 antibodies described herein). Additionally or alternatively, the antibody can be a chimeric or humanized anti-LAG-3 antibody.

Preferred cancers whose growth may be inhibited using the antibodies of the invention include cancers typically responsive to immunotherapy. Non-limiting examples of preferred cancers for treatment include melanoma (e.g., metastatic malignant melanoma), renal cancer (e.g. clear cell carcinoma), prostate cancer (e.g. hormone refractory prostate adenocarcinoma), breast cancer, colon cancer and lung cancer (e.g. non-small cell lung cancer). Additionally, the invention includes refractory or recurrent malignancies whose growth may be inhibited using the antibodies of the invention.

Examples of other cancers that can be treated using the methods of the invention include bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers. The present invention is also useful for treatment of metastatic cancers, especially metastatic cancers that express PD-L1 (Iwai et al. (2005) Int. Immunol. 17:133-144).

Optionally, antibodies to LAG-3 can be combined with an immunogenic agent, such as cancerous cells, purified tumor antigens (including recombinant proteins, peptides, and carbohydrate molecules), cells, and cells transfected with genes encoding immune stimulating cytokines (He et al (2004) J. Immunol. 173:4919-28). Non-limiting examples of tumor vaccines that can be used include peptides of melanoma antigens, such as peptides of gp100, MAGE antigens, Trp-2, MART1 and/or tyrosinase, or tumor cells transfected to express the cytokine GM-CSF (discussed further below).

In humans, some tumors have been shown to be immunogenic such as melanomas. By raising the threshold of T cell activation by LAG-3 blockade, the tumor responses in the host can be activated.

LAG-3 blockade is likely to be more effective when combined with a vaccination protocol. Many experimental strategies for vaccination against tumors have been devised (see Rosenberg, S., 2000, Development of Cancer Vaccines, ASCO Educational Book Spring: 60-62; Logothetis, C., 2000, ASCO Educational Book Spring: 300-302; Khayat, D. 2000, ASCO Educational Book Spring: 414-428; Foon, K. 2000, ASCO Educational Book Spring: 730-738; see also Restifo, N. and Sznol, M., Cancer Vaccines, Ch. 61, pp. 3023-3043 in DeVita et al. (eds.), 1997, Cancer: Principles and Practice of Oncology, Fifth Edition). In one of these strategies, a vaccine is prepared using autologous or allogeneic tumor cells. These cellular vaccines have been shown to be most effective when the tumor cells are transduced to express GM-CSF. GM-CSF has been shown to be a potent activator of antigen presentation for tumor vaccination (Dranoff et al. (1993) Proc. Natl. Acad. Sci. U.S.A. 90: 3539-43).

The study of gene expression and large scale gene expression patterns in various tumors has led to the definition of so called tumor specific antigens (Rosenberg, S A (1999) Immunity 10: 281-7). In many cases, these tumor specific antigens are differentiation antigens expressed in the tumors and in the cell from which the tumor arose, for example melanocyte antigens gp100, MAGE antigens, and Trp-2. More importantly, many of these antigens can be shown to be the targets of tumor specific T cells found in the host. LAG-3 blockade can be used in conjunction with a collection of recombinant proteins and/or peptides expressed in a tumor in order to generate an immune response to these proteins. These proteins are normally viewed by the immune system as self antigens and are therefore tolerant to them. The tumor antigen can include the protein telomerase, which is required for the synthesis of telomeres of chromosomes and which is expressed in more than 85% of human cancers and in only a limited number of somatic tissues (Kim et al. (1994) Science 266: 2011-2013). These somatic tissues may be protected from immune attack by various means. Tumor antigen can also be "neo-antigens" expressed in cancer cells because of somatic mutations that alter protein sequence or create fusion proteins between two unrelated sequences (i.e., bcr-abl in the Philadelphia chromosome), or idiotype from B cell tumors.

Other tumor vaccines can include the proteins from viruses implicated in human cancers such a Human Papilloma Viruses (HPV), Hepatitis Viruses (HBV and HCV) and Kaposi's Herpes Sarcoma Virus (KHSV). Another form of tumor specific antigen which can be used in conjunction with LAG-3 blockade is purified heat shock proteins (HSP) isolated from the tumor tissue itself. These heat shock proteins contain fragments of proteins from the tumor cells and these HSPs are highly efficient at delivery to antigen presenting cells for eliciting tumor immunity (Suot & Srivastava (1995) Science 269:1585-1588; Tamura et al. (1997) Science 278:117-120).

Dendritic cells (DC) are potent antigen presenting cells that can be used to prime antigen-specific responses. DCs can be produced ex vivo and loaded with various protein and peptide antigens as well as tumor cell extracts (Nestle et al. (1998) Nature Medicine 4: 328-332). DCs can also be transduced by genetic means to express these tumor antigens as well. DCs have also been fused directly to tumor cells for the purposes of immunization (Kugler et al. (2000) Nature Medicine 6:332-336). As a method of vaccination, DC immunization can be effectively combined with LAG-3 blockade to activate more potent anti-tumor responses.

LAG-3 blockade can also be combined with standard cancer treatments. LAG-3 blockade can be effectively combined with chemotherapeutic regimes. In these instances, it may be possible to reduce the dose of chemotherapeutic reagent administered (Mokyr et al. (1998) Cancer Research 58: 5301-5304). An example of such a combination is an anti-LAG-3 antibody in combination with decarbazine for the treatment of melanoma. Another example of such a combination is an anti-LAG-3 antibody in combination with interleukin-2 (IL-2) for the treatment of melanoma. The scientific rationale behind the combined use of LAG-3 blockade and chemotherapy is that cell death, that is a consequence of the cytotoxic action of most chemotherapeutic compounds, should result in increased levels of tumor antigen in the antigen presentation pathway. Other combination therapies that may result in synergy with LAG-3 blockade through cell death are radiation, surgery, and hormone deprivation. Each of these protocols creates a source of tumor antigen in the host. Angiogenesis inhibitors can also be combined with LAG-3 blockade. Inhibition of angiogenesis leads to tumor cell death which may feed tumor antigen into host antigen presentation pathways.

LAG-3 blocking antibodies can also be used in combination with bispecific antibodies that target Fcα or Fcγ receptor-expressing effectors cells to tumor cells (see, e.g., U.S. Pat. Nos. 5,922,845 and 5,837,243). Bispecific antibodies can be used to target two separate antigens. For example, anti-Fc receptor/anti tumor antigen (e.g., Her-2/neu) bispecific antibodies have been used to target macrophages to sites of tumor. This targeting may more effectively activate tumor specific responses. The T cell arm of these responses would be augmented by the use of LAG-3 blockade. Alternatively, antigen may be delivered directly to DCs by the use of bispecific antibodies which bind to tumor antigen and a dendritic cell specific cell surface marker.

Tumors evade host immune surveillance by a large variety of mechanisms. Many of these mechanisms may be overcome by the inactivation of proteins which are expressed by the tumors and which are immunosuppressive. These include among others TGF-β (Kehrl et al. (1986) J. Exp. Med. 163: 1037-1050), IL-10 (Howard & O'Garra (1992) Immunology Today 13: 198-200), and Fas ligand (Hahne et al. (1996) Science 274: 1363-1365). Antibodies to each of these entities can be used in combination with anti-LAG-3 to counteract the effects of the immunosuppressive agent and favor tumor immune responses by the host.

Other antibodies which activate host immune responsiveness can be used in combination with anti-LAG-3. These include molecules on the surface of dendritic cells which activate DC function and antigen presentation. Anti-CD40 antibodies are able to substitute effectively for T cell helper activity (Ridge et al. (1998) Nature 393: 474-478) and can be used in conjunction with LAG-3 antibodies (Ito et al. (2000) Immunobiology 201 (5) 527-40). Activating antibodies to T cell costimulatory molecules such as CTLA-4 (e.g., U.S. Pat. No. 5,811,097), OX-40 (Weinberg et al. (2000) Immunol 164: 2160-2169), 4-1BB (Melero et al. (1997) Nature Medicine 3: 682-685 (1997), and ICOS (Hutloff et al. (1999) Nature 397: 262-266) may also provide for increased levels of T cell activation.

Bone marrow transplantation is currently being used to treat a variety of tumors of hematopoietic origin. While graft versus host disease is a consequence of this treatment, therapeutic benefit may be obtained from graft vs. tumor responses. LAG-3 blockade can be used to increase the effectiveness of the donor engrafted tumor specific T cells.

There are also several experimental treatment protocols that involve ex vivo activation and expansion of antigen specific T cells and adoptive transfer of these cells into recipients in order to stimulate antigen-specific T cells against tumor (Greenberg & Riddell (1999) Science 285: 546-51). These methods can also be used to activate T cell responses to infectious agents such as CMV. Ex vivo activation in the presence of anti-LAG-3 antibodies can increase the frequency and activity of the adoptively transferred T cells.

Infectious Diseases

Other methods of the invention are used to treat patients that have been exposed to particular toxins or pathogens. Accordingly, another aspect of the invention provides a method of treating an infectious disease in a subject comprising administering to the subject an anti-LAG-3 antibody, or antigen-binding portion thereof, such that the subject is treated for the infectious disease. Preferably, the antibody is a human anti-human LAG-3 antibody (such as any of the human anti-LAG-3 antibodies described herein). Additionally or alternatively, the antibody can be a chimeric or humanized antibody.

Similar to its application to tumors as discussed above, antibody mediated LAG-3 blockade can be used alone, or as an adjuvant, in combination with vaccines, to stimulate the immune response to pathogens, toxins, and self-antigens. Examples of pathogens for which this therapeutic approach can be particularly useful, include pathogens for which there is currently no effective vaccine, or pathogens for which conventional vaccines are less than completely effective. These include, but are not limited to HIV, Hepatitis (A, B, & C), Influenza, Herpes, Giardia, Malaria, *Leishmania, Staphylococcus aureus, Pseudomonas aeruginosa*. LAG-3 blockade is particularly useful against established infections by agents such as HIV that present altered antigens over the course of the infections. These novel epitopes are recognized as foreign at the time of anti-human LAG-3 administration, thus provoking a strong T cell response that is not dampened by negative signals through LAG-3.

Some examples of pathogenic viruses causing infections treatable by methods of the invention include HIV, hepatitis (A, B, or C), herpes virus (e.g., VZV, HSV-1, HAV-6, HSV-II, and CMV, Epstein Barr virus), adenovirus, influenza virus, flaviviruses, echovirus, rhinovirus, coxsackie virus, coronavirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

Some examples of pathogenic bacteria causing infections treatable by methods of the invention include chlamydia, rickettsial bacteria, mycobacteria, staphylococci, streptococci, pneumonococci, meningococci and gonococci, klebsiella, proteus, serratia, pseudomonas, legionella, diphtheria, salmonella, bacilli, cholera, tetanus, botulism, anthrax, pLAGue, leptospirosis, and Lymes disease bacteria.

Some examples of pathogenic fungi causing infections treatable by methods of the invention include *Candida* (*albicans, krusei, glabrata, tropicalis*, etc.), *Cryptococcus neoformans, Aspergillus* (*fumigatus, niger*, etc.), Genus *Mucorales* (*mucor, absidia, rhizopus*), *Sporothrix schenkii, Blastomyces dermatitidis, Paracoccidioides brasiliensis, Coccidioides immitis* and *Histoplasma capsulatum*.

Some examples of pathogenic parasites causing infections treatable by methods of the invention include *Entamoeba histolytica, Balantidium coli, Naegleria fowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondii, Nippostrongylus brasiliensis*.

In all of the above methods, LAG-3 blockade can be combined with other forms of immunotherapy such as cytokine treatment (e.g., interferons, GM-CSF, G-CSF, IL-2), or bispecific antibody therapy, which provides for enhanced presentation of tumor antigens (see, e.g., Holliger (1993) Proc. Natl. Acad. Sci. USA 90:6444-6448; Poljak (1994) Structure 2:1121-1123).

Autoimmune Reactions

Anti-LAG-3 antibodies may provoke and amplify autoimmune responses. Indeed, induction of anti-tumor responses using tumor cell and peptide vaccines reveals that many anti-tumor responses involve anti-self reactivities (van Elsas et al. (2001) J. Exp. Med. 194:481-489; Overwijk, et al. (1999) Proc. Natl. Acad. Sci. U.S.A. 96: 2982-2987; Hurwitz, (2000) supra; Rosenberg & White (1996) J. Immunother Emphasis Tumor Immunol 19 (1): 81-4). Therefore, it is possible to consider using anti-LAG-3 blockade in conjunction with various self proteins in order to devise vaccination protocols to efficiently generate immune responses against these self proteins for disease treatment. For example, Alzheimer's disease involves inappropriate accumulation of $A_\beta$ peptide in amyloid deposits in the brain; antibody responses against amyloid are able to clear these amyloid deposits (Schenk et al., (1999) Nature 400: 173-177).

Other self proteins can also be used as targets such as IgE for the treatment of allergy and asthma, and TNFα for rheumatoid arthritis. Finally, antibody responses to various hormones may be induced by the use of anti-LAG-3 antibody. Neutralizing antibody responses to reproductive hormones can be used for contraception. Neutralizing antibody response to hormones and other soluble factors that are required for the growth of particular tumors can also be considered as possible vaccination targets.

Analogous methods as described above for the use of anti-LAG-3 antibody can be used for induction of therapeutic autoimmune responses to treat patients having an inappropriate accumulation of other self-antigens, such as amyloid deposits, including AP in Alzheimer's disease, cytokines such as TNFα, and IgE.

Vaccines

Anti-LAG-3 antibodies can be used to stimulate antigen-specific immune responses by coadministration of an anti-LAG-3 antibody with an antigen of interest (e.g., a vaccine).

Accordingly, in another aspect the invention provides a method of enhancing an immune response to an antigen in a subject, comprising administering to the subject: (i) the antigen; and (ii) an anti-LAG-3 antibody, or antigen-binding portion thereof, such that an immune response to the antigen in the subject is enhanced. Preferably, the antibody is a human anti-human LAG-3 antibody (such as any of the human anti-LAG-3 antibodies described herein). Additionally or alternatively, the antibody can be a chimeric or humanized antibody. The antigen can be, for example, a tumor antigen, a viral antigen, a bacterial antigen or an antigen from a pathogen. Non-limiting examples of such antigens include those discussed in the sections above, such as the tumor antigens (or tumor vaccines) discussed above, or antigens from the viruses, bacteria or other pathogens described above.

Suitable routes of administering the antibody compositions (e.g., human monoclonal antibodies, multispecific and bispecific molecules and immunoconjugates) of the invention in vivo and in vitro are well known in the art and can be selected by those of ordinary skill. For example, the antibody compositions can be administered by injection (e.g., intravenous or subcutaneous). Suitable dosages of the molecules used will depend on the age and weight of the subject and the concentration and/or formulation of the antibody composition.

As previously described, human anti-LAG-3 antibodies of the invention can be co-administered with one or other more therapeutic agents, e.g., a cytotoxic agent, a radiotoxic agent or an immunosuppressive agent. The antibody can be linked to the agent (as an immuno-complex) or can be administered separate from the agent. In the latter case (separate administration), the antibody can be administered before, after or concurrently with the agent or can be co-administered with other known therapies, e.g., an anti-cancer therapy, e.g., radiation. Such therapeutic agents include, among others, anti-neoplastic agents such as doxorubicin (adriamycin), cisplatin bleomycin sulfate, carmustine, chlorambucil, dacarbazine and cyclophosphamide hydroxyurea which, by themselves, are only effective at levels which are toxic or subtoxic to a patient. Cisplatin is intravenously administered as a 100 mg/ml dose once every four weeks and adriamycin is intravenously administered as a 60-75 mg/ml dose once every 21 days. Co-administration of the human anti-LAG-3 antibodies, or antigen binding fragments thereof, of the present invention with chemotherapeutic agents provides two anti-cancer agents which operate via different mechanisms which yield a cytotoxic effect to human tumor cells. Such co-administration can solve problems due to development of resistance to drugs or a change in the antigenicity of the tumor cells which would render them unreactive with the antibody.

Also within the scope of the present invention are kits comprising the antibody compositions of the invention (e.g., human antibodies, bispecific or multispecific molecules, or immunoconjugates) and instructions for use. The kit can further contain at least one additional reagent, or one or more additional human antibodies of the invention (e.g., a human antibody having a complementary activity which binds to an epitope in LAG-3 antigen distinct from the first human antibody). Kits typically include a label indicating the intended use of the contents of the kit. The term label includes any writing, or recorded material supplied on or with the kit, or which otherwise accompanies the kit.

Combination Therapy

In another aspect, the invention provides methods of combination therapy in which an anti-LAG-3 antibody (or antigen-binding portion thereof) of the present invention is coadministered with one or more additional antibodies that are effective in stimulating immune responses to thereby further enhance, stimulate or upregulate immune responses in a subject. In one embodiment, the invention provides a method for stimulating an immune response in a subject comprising administering to the subject an anti-LAG-3 antibody and one or more additional immunostimulatory antibodies, such as an anti-PD-1 antibody, an anti-PD-L1 antibody and/or an anti-CTLA-4 antibody, such that an immune response is stimulated in the subject, for example to inhibit tumor growth or to stimulate an anti-viral response. In another embodiment, the subject is administered an anti-LAG-3 antibody and an anti-PD-1 antibody. In still another embodiment, the subject is administered an anti-LAG-3 antibody and an anti-PD-L1 antibody. In yet another embodiment, the subject is administered an anti-LAG-3 antibody and an anti-CTLA-4 antibody. In one embodiment, the anti-LAG-3 antibody is a human antibody, such as an antibody of the disclosure. Alternatively, the anti-LAG-3 antibody can be, for example, a chimeric or humanized antibody (e.g., prepared from a mouse anti-LAG-3 mAb). In another embodiment, the at least one additional immunostimulatory antibody (e.g., anti-PD-1, anti-PD-L1 and/or anti-CTLA-4 antibody) is a human antibody. Alternatively, the at least one additional immunostimulatory antibody can be, for example, a chimeric or humanized antibody (e.g., prepared from a mouse anti-PD-1, anti-PD-L1 and/or anti-CTLA-4 antibody).

In another embodiment, the invention provides a method for treating a hyperproliferative disease (e.g., cancer), comprising administering a LAG-3 antibody and a CTLA-4 antibody to a subject. In further embodiments, the anti-LAG-3 antibody is administered at a subtherapeutic dose, the anti-CTLA-4 antibody is administered at a subtherapeutic dose, or both are administered at a subtherapeutic dose. In another embodiment, the present invention provides a method for altering an adverse event associated with treatment of a hyperproliferative disease with an immunostimulatory agent, comprising administering an anti-LAG-3 antibody and a subtherapeutic dose of anti-CTLA-4 antibody to a subject. In certain embodiments, the subject is human. In other embodiments, the anti-CTLA-4 antibody is human sequence monoclonal antibody 10D1 (described in PCT Publication WO 01/14424) and the anti-LAG-3 antibody is human sequence monoclonal antibody, such as anti-LAG-3 antibody 2# described herein. Other anti-CTLA-4 antibodies encompassed by the methods of the present invention include, for example, those disclosed in: WO 98/42752; WO 00/37504; U.S. Pat. No. 6,207,156; Hurwitz et al. (1998) Proc. Natl. Acad. Sci. USA 95(17):10067-10071; Camacho et al. (2004) J. Clin. Oncology 22(145): Abstract No. 2505 (antibody CP-675206); and Mokyr et al. (1998) Cancer Res. 58:5301-5304. In certain embodiments, the anti-CTLA-4 antibody binds to human CTLA-4 with a $K_D$ of $5 \times 10^{-8}$ M or less, binds to human CTLA-4 with a $K_D$ of $1 \times 10^{-8}$ M or less, binds to human CTLA-4 with a $K_D$ of $5 \times 10^{-9}$ M or less, or binds to human CTLA-4 with a $K_D$ of between $1 \times 10^{-8}$ M and $1 \times 10^{-10}$ M or less.

In another embodiment, the present invention provides a method for treating a hyperproliferative disease (e.g., cancer), comprising administering a LAG-3 antibody and a PD-1 antibody to a subject. In further embodiments, the anti-LAG-3 antibody is administered at a subtherapeutic dose, the anti-PD-1 antibody is administered at a subtherapeutic dose, or both are administered at a subtherapeutic dose. In another embodiment, the present invention provides a method for altering an adverse event associated with treatment of a hyperproliferative disease with an immunostimulatory agent, comprising administering an anti-LAG-3 antibody and a subtherapeutic dose of anti-PD-1 antibody to a subject. In certain embodiments, the subject is human. In certain embodiments, the anti-PD-1 antibody is a human sequence monoclonal antibody and the anti-LAG-3 antibody is human sequence monoclonal antibody. Examples of human sequence anti-PD-1 antibodies include 17D8, 2D3, 4H1, 5C4 and 4A11, which are described in PCT Publication WO 06/121168. Other anti-PD-1 antibodies include, e.g., lambrolizumab (WO2008/156712), and AMP514 (WO2010/027423, WO2010/027827, WO2010/027828, WO2010/098788). In certain embodiments, the anti-PD-1 antibody binds to human PD-1 with a $K_D$ of $5 \times 10^{-8}$ M or less, binds to human PD-1 with a $K_D$ of $1 \times 10^{-8}$ M or less, binds to human PD-1 with a $K_D$ of $5 \times 10^{-8}$ M or less, or binds to human PD-1 with a $K_D$ of between $1 \times 10^{-8}$ M and $1 \times 10^{-10}$ M or less.

In another embodiment, the present invention provides a method for treating a hyperproliferative disease (e.g., cancer), comprising administering a LAG-3 antibody and a PD-L1 antibody to a subject. In further embodiments, the anti-LAG-3 antibody is administered at a subtherapeutic dose, the anti-PD-L1 antibody is administered at a subtherapeutic dose, or both are administered at a subtherapeutic dose. In another embodiment, the present invention provides a method for altering an adverse event associated with treatment of a hyperproliferative disease with an immunostimulatory agent, comprising administering an anti-LAG-3 antibody and a subtherapeutic dose of anti-PD-L1 antibody to a subject. In certain embodiments, the subject is human. In other embodiments, the anti-PD-L1 antibody is a human sequence monoclonal antibody and the anti-LAG-3 antibody is human sequence monoclonal antibody. Examples of human sequence anti-PD-L1 antibodies include 3G10, 12A4, 10A5, 5F8, 10H10, 1B12, 7H1, 11E6, 12B7 and 13G4, which are described in PCT Publication WO 07/005,874. Other anti-PD-L1 antibodies include, e.g., MPDL3280A (RG7446) (WO2010/077634), MED14736 (WO2011/066389), and MDX1105 (WO2007/005874). In certain embodiments, the anti-PD-L1 antibody binds to human PD-L1 with a $K_D$ of $5 \times 10^{-8}$ M or less, binds to human PD-L1 with a $K_D$ of $1 \times 10^{-8}$ M or less, binds to human PD-L1 with a $KD$ of $5 \times 10^{-9}$ M or less, or binds to human PD-L1 with a $K_D$ of between $1 \times 10^{-8}$ and $1 \times 10^{-10}$ M or less.

Blockade of LAG-3 and one or more second target antigens such as CTLA-4 and/or PD-1 and/or PD-L1 by antibodies can enhance the immune response to cancerous cells in the patient. Cancers whose growth may be inhibited using the antibodies of the instant disclosure include cancers typically responsive to immunotherapy. Representative examples of cancers for treatment with the combination therapy of the instant disclosure include those cancers specifically listed above in the discussion of monotherapy with anti-LAG-3 antibodies.

In certain embodiments, the combination of therapeutic antibodies discussed herein can be administered concurrently as a single composition in a pharmaceutically acceptable carrier, or concurrently as separate compositions with each antibody in a pharmaceutically acceptable carrier. In another embodiment, the combination of therapeutic antibodies can be administered sequentially. For example, an anti-CTLA-4 antibody and an anti-LAG-3 antibody can be administered sequentially, such as anti-CTLA-4 antibody being administered first and anti-LAG-3 antibody second, or anti-LAG-3 antibody being administered first and anti-CTLA-4 antibody second. Additionally or alternatively, an anti-PD-1 antibody and an anti-LAG-3 antibody can be administered sequentially, such as anti-PD-1 antibody being administered first and anti-LAG-3 antibody second, or anti-LAG-3 antibody being administered first and anti-PD-1 antibody second. Additionally or alternatively, an anti-PD-L1 antibody and an anti-LAG-3 antibody can be administered sequentially, such as anti-PD-L1 antibody being administered first and anti-LAG-3 antibody second, or anti-LAG-3 antibody being administered first and anti-PD-L1 antibody second.

Furthermore, if more than one dose of the combination therapy is administered sequentially, the order of the sequential administration can be reversed or kept in the same order at each time point of administration, sequential administrations can be combined with concurrent administrations, or any combination thereof. For example, the first administration of a combination anti-CTLA-4 antibody and anti-LAG-3 antibody can be concurrent, the second administration can be sequential with anti-CTLA-4 first and anti-LAG-3 second, and the third administration can be sequential with anti-LAG-3 first and anti-CTLA-4 second, etc. Additionally or alternatively, the first administration of a combination anti-PD-1 antibody and anti-LAG-3 antibody can be concurrent, the second administration can be sequential with anti-PD-1 first and anti-LAG-3 second, and the third administration can be sequential with anti-LAG-3 first and anti-PD-1 second, etc. Additionally or alternatively, the first administration of a combination anti-PD-L1 antibody and anti-LAG-3 antibody can be concurrent, the second administration can be sequential with anti-PD-L1 first and anti-LAG-3 second, and the third administration can be sequential with anti-LAG-3 first and anti-PD-L1 second, etc. Another representative dosing scheme can involve a first administration that is sequential with anti-LAG-3 first and anti-CTLA-4 (and/or anti-PD-1 and/or anti-PD-L1) second, and subsequent administrations may be concurrent.

Optionally, the combination of anti-LAG-3 and one or more additional antibodies (e.g., anti-CTLA-4 and/or anti-PD-1 and/or anti-PD-L1 antibodies) can be further combined with an immunogenic agent, such as cancerous cells, purified tumor antigens (including recombinant proteins, peptides, and carbohydrate molecules), cells, and cells transfected with genes encoding immune stimulating cytokines (He et al. (2004) J. Immunol. 173:4919-28). Non-limiting examples of tumor vaccines that can be used include peptides of melanoma antigens, such as peptides of gp100, MAGE antigens, Trp-2, MART1 and/or tyrosinase, or tumor cells transfected to express the cytokine GM-CSF (discussed further below). A combined LAG-3 and CTLA-4 and/or PD-1 and/or PD-L1 blockade can be further combined with a vaccination protocol, such as any of the vaccination protocols discussed in detail above with respect to monotherapy with anti-LAG-3 antibodies.

A combined LAG-3 and CTLA-4 and/or PD-1 and/or PD-L1 blockade can also be further combined with standard cancer treatments. For example, a combined LAG-3 and CTLA-4 and/or PD-1 and/or PD-L1 blockade can be effectively combined with chemotherapeutic regimes. In these instances, it is possible to reduce the dose of other chemotherapeutic reagent administered with the combination of the instant disclosure (Mokyr et al. (1998) Cancer Research 58: 5301-5304). An example of such a combination is a combination of anti-LAG-3 and anti-CTLA-4 antibodies and/or anti-PD-1 antibodies and/or anti-PD-L1 antibodies further in combination with decarbazine for the treatment of melanoma. Another example is a combination of anti-LAG-3 and anti-CTLA-4 antibodies and/or anti-PD-1 antibodies and/or anti-PD-L1 antibodies further in combination with interleukin-2 (IL-2) for the treatment of melanoma. The scientific rationale behind the combined use of LAG-3 and CTLA-4 and/or PD-1 and/or PD-L1 blockade with chemotherapy is that cell death, which is a consequence of the cytotoxic action of most chemotherapeutic compounds, should result in increased levels of tumor antigen in the antigen presentation pathway. Other combination therapies that may result in synergy with a combined LAG-3 and CTLA-4 and/or PD-1 and/or PD-L1 blockade through cell death include radiation, surgery, or hormone deprivation. Each of these protocols creates a source of tumor antigen in the host. Angiogenesis inhibitors can also be combined with a combined LAG-3 and CTLA-4 and/or PD-1 and/or PD-L blockade. Inhibition of angiogenesis leads to tumor cell death, which can be a source of tumor antigen fed into host antigen presentation pathways.

A combination of LAG-3 and CTLA-4 and/or PD-1 and/or PD-L1 blocking antibodies can also be used in combination with bispecific antibodies that target Fcα or Fcγ receptor-expressing effector cells to tumor cells (see, e.g., U.S. Pat. Nos. 5,922,845 and 5,837,243). Bispecific antibodies can be used to target two separate antigens. The T cell arm of these responses would be augmented by the use of a combined LAG-3 and CTLA-4 and/or PD-1 and/or PD-L1 blockade.

In another example, a combination of anti-LAG-3 and anti-CTLA-4 and/or anti-PD-1 antibodies and/or anti-PD-L1 antibodies can be used in conjunction with anti-neoplastic antibodies, such as Rituxan™ (rituximab), Herceptin™ (trastuzumab), Bexxar™ (tositumomab), Zevalin™ (ibritumomab), Campath™ (alemtuzumab), Lymphocide™ (eprtuzumab), Avastin™ (bevacizumab), and Tarceva™ (erlotinib), and the like. By way of example and not wishing to be bound by theory, treatment with an anti-cancer antibody or an anti-cancer antibody conjugated to a toxin can lead to cancer cell death (e.g., tumor cells) which would potentiate an immune response mediated by CTLA-4, PD-1, PD-L1 or LAG-3. In an exemplary embodiment, a treatment of a hyperproliferative disease (e.g., a cancer tumor) can include an anti-cancer antibody in combination with anti-LAG-3 and anti-CTLA-4 and/or anti-PD-1 and/or anti-PD-L1 antibodies, concurrently or sequentially or any combination thereof, which can potentiate an anti-tumor immune response by the host.

Tumors evade host immune surveillance by a large variety of mechanisms. Many of these mechanisms may be overcome by the inactivation of proteins, which are expressed by the tumors and which are immunosuppressive. These include, among others, TGF-β (Kehrl et al. (1986) J. Exp. Med. 163: 1037-1050), IL-10 (Howard & O'Garra (1992) Immunology Today 13: 198-200), and Fas ligand (Hahne et al. (1996) Science 274: 1363-1365). In another example, antibodies to each of these entities can be further combined with an anti-LAG-3 and anti-CTLA-4 and/or anti-PD-1 and/or anti-PD-L1 antibody combination to counteract the effects of immunosuppressive agents and favor anti-tumor immune responses by the host.

Other antibodies that can be used to activate host immune responsiveness can be further used in combination with an anti-LAG-3 and anti-CTLA-4 and/or anti-PD-1 and/or anti-PD-L1 antibody combination. These include molecules on the surface of dendritic cells that activate DC function and antigen presentation. Anti-CD40 antibodies (Ridge et al., supra) can be used in conjunction with an anti-LAG-3 and anti-CTLA-4 and/or anti-PD-1 and/or anti-PD-L1 combination (Ito et al., supra). Other activating antibodies to T cell costimulatory molecules (Weinberg et al., supra, Melero et al. supra, Hutloff et al., supra) may also provide for increased levels of T cell activation.

As discussed above, bone marrow transplantation is currently being used to treat a variety of tumors of hematopoietic origin. A combined LAG-3 and CTLA-4 and/or PD-1 and/or PD-L1 blockade can be used to increase the effectiveness of the donor engrafted tumor specific T cells.

Several experimental treatment protocols involve ex vivo activation and expansion of antigen specific T cells and adoptive transfer of these cells into recipients in order to antigen-specific T cells against tumor (Greenberg & Riddell, supra). These methods can also be used to activate T cell responses to infectious agents such as CMV. Ex vivo activation in the presence of anti-LAG-3 and anti-CTLA-4 and/or anti-PD-1 and/or anti-PD-L1 antibodies can be expected to increase the frequency and activity of the adoptively transferred T cells.

In certain embodiments, the present invention provides a method for altering an adverse event associated with treatment of a hyperproliferative disease (e.g., cancer) with an immunostimulatory agent, comprising administering an anti-LAG-3 antibody and a subtherapeutic dose of anti-CTLA-4 and/or anti-PD-1 and/or anti-PD-L1 antibody to a subject. For example, the methods of the present invention provide for a method of reducing the incidence of immunostimulatory therapeutic antibody-induced colitis or diarrhea by administering a non-absorbable steroid to the patient. Because any patient who will receive an immunostimulatory therapeutic antibody is at risk for developing colitis or diarrhea induced by such an antibody, this entire patient population is suitable for therapy according to the methods of the present invention. Although steroids have been administered to treat inflammatory bowel disease (IBD) and prevent exacerbations of IBD, they have not been used to prevent (decrease the incidence of) IBD in patients who have not been diagnosed with IBD. The significant side effects associated with steroids, even non-absorbable steroids, have discouraged prophylactic use.

In further embodiments, a combination LAG-3 and CTLA-4 and/or PD-1 and/or PD-L1 blockade (i.e., immunostimulatory therapeutic antibodies anti-LAG-3 and anti-CTLA-4 and/or anti-PD-1 antibodies and/or anti-PD-L1 antibodies) can be further combined with the use of any non-absorbable steroid. As used herein, a "non-absorbable steroid" is a glucocorticoid that exhibits extensive first pass metabolism such that, following metabolism in the liver, the bioavailability of the steroid is low, i.e., less than about 20%. In one embodiment of the invention, the non-absorbable steroid is budesonide. Budesonide is a locally-acting glucocorticosteroid, which is extensively metabolized, primarily by the liver, following oral administration. ENTOCORT EC™ (Astra-Zeneca) is a pH- and time-dependent oral formulation of budesonide developed to optimize drug delivery to the ileum and throughout the colon. ENTOCORT EC™ is approved in the U.S. for the treatment of mild to moderate Crohn's disease involving the ileum and/or ascending colon. The usual oral dosage of ENTOCORT EC™ for the treatment of Crohn's disease is 6 to 9 mg/day. ENTOCORT EC™ is released in the intestines before being absorbed and retained in the gut mucosa. Once it passes through the gut mucosa target tissue, ENTOCORT EC™ is extensively metabolized by the cytochrome P450 system in the liver to metabolites with negligible glucocorticoid activity. Therefore, the bioavailability is low (about 10%). The low bioavailability of budesonide results in an improved therapeutic ratio compared to other glucocorticoids with less extensive first-pass metabolism. Budesonide results in fewer adverse effects, including less hypothalamic-pituitary suppression, than systemically-acting corticosteroids. However, chronic administration of ENTOCORT EC™ can result in systemic glucocorticoid effects such as hypercorticism and adrenal suppression. See PDR 58$^{th}$ ed. 2004; 608-610.

In still further embodiments, a combination LAG-3 and CTLA-4 and/or PD-1 and/or PD-L1 blockade (i.e., immunostimulatory therapeutic antibodies anti-LAG-3 and anti-CTLA-4 and/or anti-PD-1 and/or anti-PD-L1 antibodies) in conjunction with a non-absorbable steroid can be further combined with a salicylate. Salicylates include 5-ASA agents such as, for example: sulfasalazine (AZULFIDINE™, Pharmacia & UpJohn); olsalazine (DIPENTUM™, Pharmacia & UpJohn); balsalazide (COLAZAL™, Salix Pharmaceuticals, Inc.); and mesalamine (ASACOL™, Procter & Gamble Pharmaceuticals; PENTASA™, Shire US; CANASA™, Axcan Scandipharm, Inc.; ROWASA™, Solvay).

In accordance with the methods of the present invention, a salicylate administered in combination with anti-LAG-3 and anti-CTLA-4 and/or anti-PD-1 and/or anti-PD-L1 antibodies and a non-absorbable steroid can includes any overlapping or sequential administration of the salicylate and the non-absorbable steroid for the purpose of decreasing the incidence of colitis induced by the immunostimulatory antibodies. Thus, for example, methods for reducing the incidence of colitis induced by the immunostimulatory antibodies according to the present invention encompass administering a salicylate and a non-absorbable concurrently or sequentially (e.g., a salicylate is administered 6 hours after a non-absorbable steroid), or any combination thereof. Further, according to the present invention, a salicylate and a non-absorbable steroid can be administered by the same route (e.g., both are administered orally) or by different routes (e.g., a salicylate is administered orally and a non-absorbable steroid is administered rectally), which may differ from the route(s) used to administer the anti-LAG-3 and anti-CTLA-4 and/or anti-PD- and/or anti-PD-L1 antibodies.

The present disclosure is further illustrated by the following examples, which should not be construed as further limiting. The contents of all figures and all references, Genbank sequences, patents and published patent applications cited throughout this application are expressly incorporated herein by reference. In particular, the disclosures of PCT publications WO 09/045,957, WO 09/073,533, WO 09/073,546, and WO 09/054,863 are expressly incorporated herein by reference.

EXAMPLES

Example 1 Phage Panning and Screening

An antibody single chain phage display library was created by cloning a repertoire of light chain variable regions (VL) and heavy chain variable regions (VH), as shown in FIG. 1. The heavy and light chain repertoires were created by PCR amplification from human lymphocytes mainly collected from peripheral and newborn umbilical cord blood. The VL repertoire and VH repertoire were mixed and underwent PCR with overlapping primers. The final format of the antibody was a single chain Fv (scFv) with VH and VL fragments joined by a flexible linker peptide (SGGSTITSYNVYYTKLSSSGT (SEQ ID NO: 40)). The primary library was further enlarged by the LoxP-cre system.

Selection of phage particles displaying specific scFv fragments was performed on Immuno 96 MicroWell™ Plates (Nunc, Denmark). First, 50 µg/ml of LAG3 recombinant protein (Cat # LA3-5222, Acrobiosystems) in phosphate-buffered saline (PBS) was coated on the plates overnight at 4° C. Following blocking with 2% (w/v) milk powder in PBS (2% MPBS), a library containing about 10¹¹ phage particles were added and the plate was incubated for 2 hours at room temperature (RT; 25-28° C.). Non-bound phages were eliminated by washing 10-20 times with PBS containing 0.1% Tween 20 (PBS-T), followed by 10-20 times washing with PBS. The bound phages were eluted by incubation with 50 μl of 1 μg/l trypsin for 10 min, followed by 50 μl of 50 mM glycine-HCl pH 2.0 (immediately neutralized with 50 μl of 200 mM Na₂HPO₄, pH7.5 after 10 min). Eluted phages were used to infect exponentially growing E. coli TG1 cells by incubating for 30 min at 37° C. Infected cells were spread on TYE plate containing ampicillin (100 μg/mL) and glucose (1% w/v), and then the plate was incubated overnight at 37° C. Individual phage-infected colonies were picked and grown for production of phagemid particles in 96-well plates. The culture was rescued using either MI3KO7 or KMI3 helper phage. Rescued phage particles were used to initiate subsequent rounds of selection using similar conditions. Three rounds of selection were performed for LAG3 protein.

To test LAG3 binding in enzyme-linked immunosorbent assay (ELISA), individual clones from last panning were picked and grown at 37° C. and rescued with M13K07 helper phage. The amplified phage preparation was blocked with 5% nonfat milk in PBS at 37° C. for 1 h and added to 96-well microplates (Nunc) coated with LAG3 (Cat # LA3-5222, Acrobiosystems) (0.5 μg/ml). After incubation at 37° C. for another hour, the plates were washed three times with PBST and incubated with a mouse horseradish peroxidase (HRP) conjugated anti-M13 phage antibody (Amersham). After careful washing, 3,30,5,50-tetramethylbenzydine (TMB, Sigma) was added as substrate. The color reaction was measured at 450 nm with a Thermo multiskan ELISA reader (MA, USA).

From the third round of screening, 300 phages were picked up and tested for human LAG-3 binding, and 29 clones were found to be able to bind to human LAG-3 (Cat # LA3-5222, Acrobiosystems) specifically.

Out of the 29 clones, 16 clones were confirmed to bind to human LAG-3 specifically in a further testing. These 16 clones were re-numbered as clone 1-16 and sequenced, from which 5 unique sequences were identified including clone 2#, 6#, 8#, 13#, and 14# (i.e., anti-LAG-3 antibody 2#, 6#, 8#, 13# and 14#).

The amino acid sequences of anti-LAG3 antibody 6#, 8#, 13# and 14# are set forth in SEQ ID NOs.: 42, 44, 46 and 48, respectively, which may be encoded by nucleic acid sequences of SEQ ID NOs.: 41, 43, 45 and 47, respectively.

```
Amino acid sequence of Clone 6
                                       (SEQ ID NO: 42)
QVQLVQSGGGVVQPGRSLRLPCAASGFTFSSYGMHWVRQAPGKGLEWVAA

ISYDGSNKYYADSVKGRFTISRDNSKNTLYLQMNSLRAEDTAVYYCAREG

SYYLEGIDYWGQGTLVTVSS (heavy chain variable region)

ASTKGPSVFPLAPCSRSTSESTAALGCLVKDYFPEPVTVSWNSGALTSGV

HTFPAVLQSSGLYSLSSVVTVPSSSLGTKTYTCNVDHKPSNTKVDKRVES

KYGPPCPPCPAPEFLGGPSVFLFPPKPKDTLMISRTPEVTCVVVDVSQED

PEVQFNWYVDGVEVHNAKTKPREEQFNSTYRVVSVLTVLHQDWLNGKEYK

CKVSNKGLPSSIEKTISKAKGQPREPQVYTLPPSQEEMTKNQVSLTCLVK
```

```
GFYPSDIAVEWESNGQPENNYKTTPPVLDSDGSFFLYSRLTVDKSRWQEG

NVFSCSVMHEALHNHYTQKSLSLSLGK (heavy chain constant
region)

QSVLTQPPSVSEAPRQRVTISCSGSSSNIGDNAVNWYQQLPGKAPTLLIY

YDDLLPSGVPDRFSGSKSGTSASLATSGLQSEDEAEYYCAAWDDSLKGYV

FGTGTKLTVLG (light chain variable region)

QPKAAPSVTLFPPSSEELQANKATLVCLISDFYPGAVTVAWKADSSPVKA

GVETTTPSKQSNNKYAASSYLSLTPEQWKSHRSYSCQVTHEGSTVEKTVA

PTECS (light chain constant region)

Amino acid sequence of Clone 8
                                       (SEQ ID NO: 44)
QVQLQESGGGVVRPGGSLRLSCAASGFTFDDYGMSWVRQAPGKGLEWVSG

INWSGGSTYYADSVKGRSTISRDNSKNTLYLQMNSLRAEDTAVYYCATGG

YWGQGTLVTVSS (heavy chain variable region)

ASTKGPSVFPLAPCSRSTSESTAALGCLVKDYFPEPVTVSWNSGALTSGV

HTFPAVLQSSGLYSLSSVVTVPSSSLGTKTYTCNVDHKPSNTKVDKRVES

KYGPPCPPCPAPEFLGGPSVFLFPPKPKDTLMISRTPEVTCVVVDVSQED

PEVQFNWYVDGVEVHNAKTKPREEQFNSTYRVVSVLTVLHQDWLNGKEYK

CKVSNKGLPSSIEKTISKAKGQPREPQVYTLPPSQEEMTKNQVSLTCLVK

GFYPSDIAVEWESNGQPENNYKTTPPVLDSDGSFFLYSRLTVDKSRWQEG

NVFSCSVMHEALHNHYTQKSLSLSLGK (heavy chain constant
region)

SYELTQPPSVSVSPGQTASITCSGDKLGDKYTSWYQQKPGQSPLLVIYQS

TKRPSGIPERFSGSNSGDTATLTISGTQPMDEADYYCQAWDSSTAVFGGG

TKLTVLG (light chain variable region)

QPKAAPSVTLFPPSSEELQANKATLVCLISDFYPGAVTVAWKADSSPVKA

GVETTTPSKQSNNKYAASSYLSLTPEQWKSHRSYSCQVTHEGSTVEKTVA

PTECS (light chain constant region)

Amino acid sequence of Clone 13
                                       (SEQ ID NO: 46)
QVQLQESGGGVVRPGGSLRLSCAASGFTFDDYGMSWVRQAPGKGLEWVSG

INWSGGSTYYADSVKGRSTISRDNSKNTLYLQMNSLRAEDTAVYYCATGG

YWGQGTLVTVSS (heavy chain variable region)

ASTKGPSVFPLAPCSRSTSESTAALGCLVKDYFPEPVTVSWNSGALTSGV

HTFPAVLQSSGLYSLSSVVTVPSSSLGTKTYTCNVDHKPSNTKVDKRVES

KYGPPCPPCPAPEFLGGPSVFLFPPKPKDTLMISRTPEVTCVVVDVSQED

PEVQFNWYVDGVEVHNAKTKPREEQFNSTYRVVSVLTVLHQDWLNGKEYK

CKVSNKGLPSSIEKTISKAKGQPREPQVYTLPPSQEEMTKNQVSLTCLVK

GFYPSDIAVEWESNGQPENNYKTTPPVLDSDGSFFLYSRLTVDKSRWQEG

NVFSCSVMHEALHNHYTQKSLSLSLGK (heavy chain constant
region)

QSVLTQPPSVSGAPGQRVTISCTGSSSNIGAGYDVHWYQQLPGTAPKLLI
```

-continued

YGNSNRPSGVPDRFSGSKSGTSASLAITGLQAEDEADYYCQSYDSSLSVV

FGGGTKLTVLG (light chain variable region)

QPKAAPSVTLFPPSSEELQANKATLVCLISDFYPGAVTVAWKADSSPVKA

GVETTTPSKQSNNKYAASSYLSLTPEQWKSHRSYSCQVTHEGSTVEKTVA

PTECS (light chain constant region)

Amino acid sequence of Clone 14
(SEQ ID NO: 48)
EVQLVQSGGGLVQPGRSLRLSCTASGFTFGDYAMHWVRQAPGKGLEWVSG

ISWNSGSIGYADSVKGRFTISRDNAKNSLYLQMNSLRAEDTAVYYCAKFR

SSSWYDYFDSWGQGTLVTVSS (heavy chain variable region)

ASTKGPSVFPLAPCSRSTSESTAALGCLVKDYFPEPVTVSWNSGALTSGV

HTFPAVLQSSGLYSLSSVVTVPSSSLGTKTYTCNVDEIKPSNTKVDKRVE

SKYGPPCPPCPAPEFLGGPSVFLFPPKPKDTLMISRTPEVTCVVVDVSQE

DPEVQFNWYVDGVEVHNAKTKPREEQFNSTYRVVSVLTVLHQDWLNGKEY

KCKVSNKGLPSSIEKTISKAKGQPREPQVYTLPPSQEEMTKNQVSLTCLV

KGFYPSDIAVEWESNGQPENNYKTTPPVLDSDOSFFLYSRLTVDKSRWQE

GNVFSCSVMHEALHNHYTQKSLSLSLGK (heavy chain constant region)

QSVLTQPPSASGTPGQRVTISCSGSSSNIGSNTVNWYQQLPGTAPKLLIY

SNNQRPSGVPDRFSGSKSGTSASLATSGLQSEDEADYYCAAWDDSLNGWV

FGGGTKLTVLG (light chain variable region)

QPKAAPSVTLFPPSSEELQANKATLVCLISDFYPGAVTVAWKADSSPVKA

GVETTTPSKQSNNKYAASSYLSLTPEQWKSHRSYSCQVTHEGSTVEKTVA

PTECS (light chain constant region)

Example 2 Expression and Purification of
Full-Length Antibodies

Method to produce full-length human IgG1 antibody from scFv was established. Genes encoding the VH and VL regions of anti-LAG3 antibodies were sequentially inserted into the expression vector pIgG containing the gene for hIgG1 Heavy chain constant region and kappa light constant region. For the expression of soluble antibodies in mammalian cells, recombinant pIgG was transiently transfected into human 293T cells with lipofactamine. Transfected cells were maintained in 293 SFM at 37° C. for 8 days. During this time, the medium was changed twice and culture supernatants were collected. Full-length antibodies secreted into the medium were purified with Protein A affinity chromatography (Pharmacia). Purified antibodies were concentrated to 1 mg/ml, sterile filtered, and characterized by SDS-PAGE, ELISA and isothermal titration calorimetry (ITC).

Example 3 Physical and Chemical Analysis

For the 5 clones, the integrity of heavy and light chains and also integrity of antibody were confirmed by reducing SDS-PAGE and non-reducing SDS-PAGE, respectively.

Clone #2 was further tested in Size Exclusion Chromatography. In particular, 20 μg of sample was injected on a TSK G3000SWXL column using 100 mM sodium phosphate+100 mM $Na_2SO_4$, pH 7.0, as running buffer. The run time was 30 min. All measurements were performed on Agilent 1220 HPLC. Data was analyzed using OpenLAB software. Main peak of the anti-LAG3 antibody 2# is above 95% in SEC, suggesting high purity and integrity of the purified antibody.

Example 4 Anti-LAG-3 Antibodies Bound to
Human LAG-3 Specifically

An ELISA assay was used for determination of the relative binding activity of antibodies to recombinant human LAG-3.

Human LAG-3 protein (Cat # LA3-5222, Acrobiosystems) was immobilized onto 96-well plates by incubation overnight at 4° C. The plates were then blocked by incubation with 1% BSA in PBS for one hour at 37° C. After blocking, the plates were washed three times with PBST (PBS containing 0.05% Tween20). Serially diluted anti-LAG-3 antibodies (Clone 2#, 8#, 13#, and LAG3.5 (BMS-986016, developed by Bristol-Myers Squibb)) were prepared in binding buffer (PBS containing 0.05% Tween20 and 0.5% BSA) and incubated with the immobilized proteins for one hour at 37° C. After binding, the plates were washed three times with PBST, incubated for one hour at 37° C. with peroxidase-labeled donkey anti-human IgG (Jackson Immuno Research) diluted 1/15,000 in binding buffer, washed again, developed with TMB and stopped with 1 M $H_2SO_4$.

Figure 2:
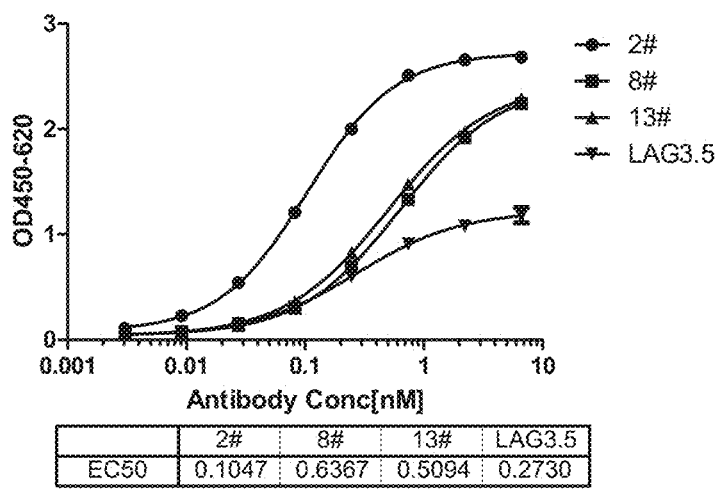
FIG. 2 is a graph showing the binding activity of anti-LAG-3 antibody 2#, 8#, 13# and LAG3.5 to human LAG-3 recombinant protein in an ELISA assay.

The $EC_{50}$ and representative binding curves for the clones binding to human LAG-3 were shown in FIG. 2.

The result indicated that all antibodies bound to human LAG-3 specifically, with clone 2# showing the highest binding capacity.

Example 5 Anti-LAG-3 Antibodies Bound to the
Domain 1-2 of Human LAG-3

An ELISA assay was used for determination of the relative binding activity of antibodies to domain 1-2 of human LAG-3.

Recombinant LAG-3 domain 1-2 (Amino acid 1-262, SEQ ID NO.:49) was fused to human IgG1 Fc domain and transiently expressed in ExpiCHO system (Thermofisher), the supernatants were harvested and purified by protein A (GE healthcare). Recombinant LAG-3 domain 1-2 was immobilized onto 96-well plates by incubation overnight at 4° C. The plates were then blocked by incubation with 1% BSA in PBS for one hour at 37° C. After blocking, the plates were washed three times with PBST (PBS containing 0.05% Tween20). Serially diluted anti-LAG-3 antibodies (Clone 2#, 8#, 13#, and 14#) were prepared in binding buffer (PBS containing 0.05% Tween20 and 0.5% BSA) and incubated in plates with the immobilized protein for one hour at 37° C. After incubation, the plates were washed three times with PBST, incubated for one hour at 37° C. with peroxidase-labeled Goat anti-human F(ab')$_2$ (JacksonImmunoResearch) diluted 1/10,000 in binding buffer, washed again, developed with TMB and stopped with 1M $H_2SO_4$.

Figure 3:
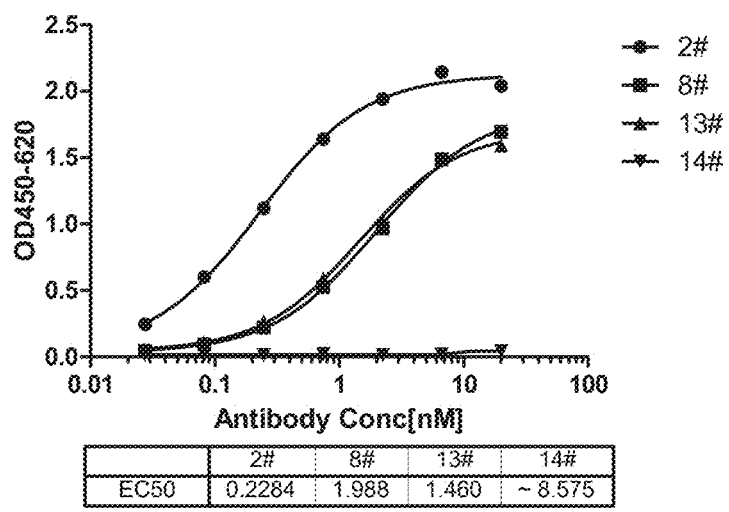
FIG. 3 is a graph showing the binding activity of anti-LAG-3 antibody 2#, 8#, 13# and 14# to domain 1-2 of human LAG-3 recombinant protein in an ELISA assay.

The $EC_{50}$ and representative binding curves for these clones binding to domain 1-2 of human LAG3 were shown in FIG. 3.

The result suggested that clone 2#, 8#, and 13# can bind to domain 1-2 of LAG-3 while clone 14# cannot bind to domain 1-2.

Example 6 Affinity of Anti-LAG-3 Antibodies to Human LAG-3

The kinetic binding activity of anti-LAG-3 clones to human LAG-3 (Cat # LA3-5222, Acrobiosystems) was measured by surface plasmon resonance using a Biacore T200 system (Biacore, GE Healthcare).

Approximately 6800 RU of Anti-Human IgG (Fc) antibody (GE Catalog # BR-1008-39) was immobilized via amine coupling chemistry onto a CM5 sensor chip. Antibodies (Clone 2#, 6#, 8#, 13#, and 14#) were injected over the surface of the immobilized goat anti-human IgG antibody. HBS-EP+ buffer was used as the running buffer. Varying concentrations of human LAG-3 protein, ranging from 6.25 nM to 200 nM, were injected over the antibody surfaces. Following each injection cycle, the CM5 chip surface was regenerated using injection of 3M magnesium chloride solution. Background subtraction binding sensorgrams were used for analyzing the rate of association Ka and dissociation Kd, and the equilibrium dissociation constant $K_D$. The resulting data sets were fitted with a 1:1 Langmuir Binding Model using the Biacore T200 evaluation software.

Table 1 below summarized the affinities of the anti-LAG3 antibodies to recombinant human LAG-3.

TABLE 1

Affinities of anti-LAG-3 antibodies to recombinant human LAG-3

| Clone# | $K_a$ (M$^{-1}$S$^{-1}$) | $K_d$ (S$^{-1}$) | $K_D$(M) |
|---|---|---|---|
| Clone 2# | 1.782E+6 | 6.200E−4 | 3.480E−10 |
| Clone 6# | 2.456E+4 | 9.427E−4 | 3.839E−8 |
| Clone 8# | 1.429E+5 | 2.976E−4 | 2.082E−9 |
| Clone 13# | 9.218E+4 | 0.04484 | 4.864E−7 |
| Clone 14# | 3.194E+4 | 8.918E−4 | 2.792E−8 |

The results showed that Clone 2# had the highest affinity to recombinant human LAG-3.

Example 7 Internalization of Anti-LAG-3 Antibodies on Jurkat-LAG-3 Cells

Anti-LAG-3 antibodies were tested for the ability to be internalized on Jurkat-LAG-3 cells.

Jurkat-LAG3 cells transfected with human LAG3 gene and thus stably expressing human LAG-3 were incubated with anti-LAG-3 antibodies (LAG3 2# and LAG3.5(BMS)) in duplicates for 1 hour at 4° C. The cells were washed once, divided into 2 groups, one of which incubated at 37° C. and the other incubated at 4° C. After 2 hours, the binding was detected using a FITC conjugated AffinityPure Donkey Anti-human (H+L) IgG (Jackson Immuno Research) secondary reagent incubated at 4° C. for 30 min followed by washing once. After that, cells were resuspended in PBS buffer. Analysis of human LAG-3 binding was carried out with the BD Accuri C5 flow cytometer (BD Bioscience).

Figure 4:
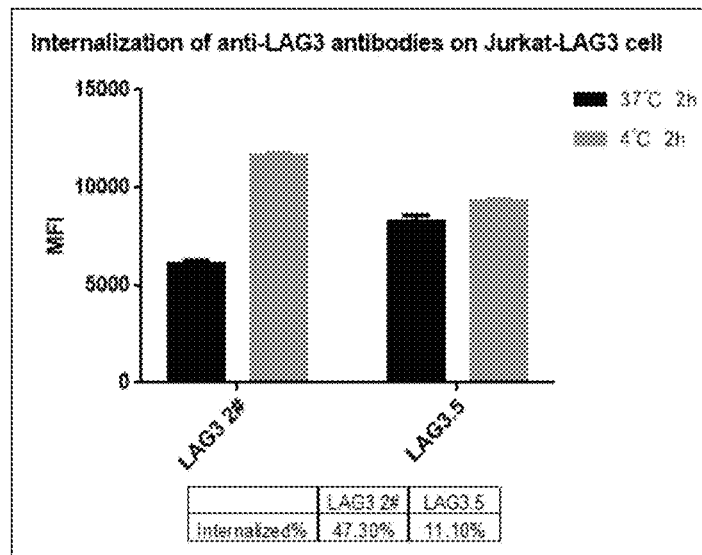
FIG. 4 is a graph showing internalization of anti-LAG-3 antibody 2# and LAG3.5 on Jurkat-LAG3 cells.

As shown in FIG. 4, the anti-LAG-3 antibody 2# was internalized on Jurkat-LAG-3 cells.

Example 8 Binding Affinity of Anti-LAG3 Antibodies to Human, Cynomolgus Monkey and Rhesus Monkey LAG-3 Protein The kinetic binding activity of anti-LAG-3 antibody 2# to human LAG-3 protein (Cat # LA3-5222, Acrobiosystems), cynomolgus monkey LAG-3 protein (Cat # LA3-C52A0, Acrobiosystems) and recombinant rhesus monkey LAG-3 protein was measured by ForteBio Octet RED 96 (Fortebio), respectively. The recombinant rhesus monkey LAG-3 proteins were prepared by fusing Amino acids 1-450 of XM_001108923.3 (SEQ ID NO.: 50) to human IgG1 Fc domain, transiently expressing the proteins in ExpiCHO system (Thermofisher), collecting the supernatants and purifying the proteins by protein A(GE healthcare).

The biotin labeled anti-LAG-3 antibody 2# and LAG3.5 were binding to pre-equilibrated streptavidin (SA) biosensors. Varying concentrations of human LAG-3, cynomolgus monkey LAG-3 and rhesus monkey LAG-3 protein, ranging from 3.125 nM to 100 nM were binding to the antibody. The data sets were fitted with a 1:1 Binding Model using Octet software.

Table 2 summarized the affinities for the anti-human LAG3 antibody 2# and LAG3.5 to human, cynomolgus monkey and rhesus monkey LAG-3 protein.

TABLE 2

Affinities of anti-LAG-3 antibodies to recombinant human LAG-3

| Antibody | Antigen | $K_a$(M$^{-1}$S$^{-1}$) | $K_d$(S$^{-1}$) | $K_D$(M) |
|---|---|---|---|---|
| Anti-LAG-3 antibody 2# | Cynomolgus monkey LAG-3 | 4.57E+5 | 5.80E−4 | 1.27E−9 |
| | Rhesus monkey LAG-3 | 5.54E+5 | 6.76E−4 | 1.22E−9 |
| | Human LAG-3 | 2.80E+05 | 3.65E−05 | 1.30E−10 |
| LAG3.5 | Cynomolgus monkey LAG-3 | 5.10E+05 | 1.13E−03 | 2.22E−09 |
| | Rhesus monkey LAG-3 | 2.02E+05 | 1.02E−03 | 5.07E−09 |
| | Human LAG-3 | 2.90E+05 | 5.35E−04 | 1.85E−09 |

The anti-LAG-3 antibody 2# had lower $K_D$ value than LAG3.5 in binding to human LAG-3.

Example 9 Anti-LAG-3 Antibodies Did not Cross React with Mouse LAG-3

An ELISA assay was used for determination of the relative binding activity of antibodies to mouse LAG-3.

Mouse LAG-3 (Acrobiosystems) was immobilized onto 96-well plates by incubation overnight at 4° C. Nonspecific binding sites were blocked by incubation with 1% BSA in PBS for one hour at 37° C. After blocking, the plates were washed three times with PBST (PBS containing 0.05% Tween20). Serially diluted anti-LAG-3 antibodies (Clone 2#, 6#, 8#, 13#, and 14#) were prepared in binding buffer (PBS containing 0.05% Tween20 and 0.5% BSA) and incubated with the immobilized proteins for one hour at 37° C. After binding, the plates were washed three times with PBST, incubated for one hour at 37° C. with peroxidase-labeled donkey anti-human IgG (JacksonImmunoResearch) diluted 1/15,000 in binding buffer, washed again, developed with TMB and stopped with 1M $H_2SO_4$.

Figure 5:
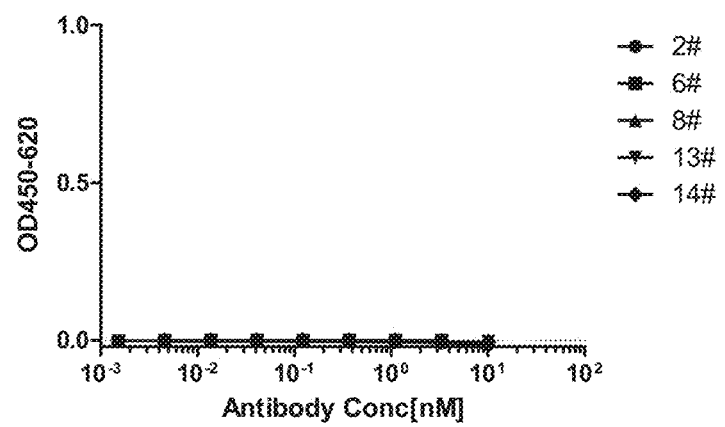
FIG. 5 is a graph showing the binding activity of anti-LAG-3 antibody 2#, 6#, 8#, 13# and 14# to mouse LAG-3 recombinant protein in an ELISA assay.

Representative binding curves for these clones binding mouse LAG-3 were shown in FIG. 5.

The result suggested that that no clone cross-reacted with mouse LAG-3.

Example 10 Anti-LAG-3 Antibodies do not Cross React with Human CD4

Since CD4 bound to MHC class II molecule, an ELISA assay was used for determination of the relative binding activity of anti-LAG-3 antibodies to human CD4.

CD4 (Sino Biological) was immobilized onto 96-well plates by incubation overnight at 4° C. Nonspecific binding sites were blocked by incubation with 1% BSA in PBS for one hour at 37° C. After blocking, the plates were washed three times with PBST (PBS containing 0.05% Tween20). Serially diluted anti-LAG-3 antibodies (Clone 2#, 6#, 8#, 13#, and 14#) were prepared in binding buffer (PBS containing 0.05% Tween20 and 0.5% BSA) and incubated with the immobilized protein for one hour at 37° C. After binding, the plates were washed three times with PBST, incubated for one hour at 37° C. with peroxidase-labeled donkey anti-human IgG (JacksonImmunoResearch) diluted 1/15,000 in binding buffer, washed again, and developed with TMB and stopped with 1M $H_2SO_4$.

Figure 6:
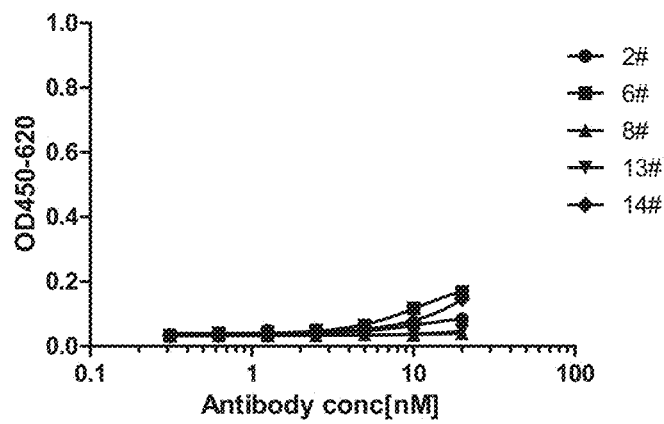
FIG. 6 is a graph showing the binding activity of anti-LAG-3 antibody 2#, 6#, 8#, 13# and 14# to human CD4 recombinant protein in an ELISA assay.

Representative binding curves for clones binding human CD4 were shown in FIG. 6.

The result suggested that these clones did not bind to human CD4.

Example 11 Anti-LAG-3 Antibodies Blocked Interaction of MHC Class II with LAG-3

To assess the ability of the anti-LAG-3 antibodies to inhibit human LAG-3 binding to MHC Class II molecules, an in vitro binding assay was performed in which a LAG-3 fusion protein, comprising human LAG-3 extracellular domain fused to mouse Fc (SinoBiological, hLAG-3-mFc), was reacted with Daudi cells, which expressed human MHC Class II molecules.

To test antibody inhibition in this assay, anti-LAG3 antibodies (Clone 2#, and 8#) were serially diluted in PBS buffer with 0.5% BSA and to these serial dilutions was added with hLAG-3-mFc fusion protein respectively. This mixture was incubated for 20 minutes at room temperature and then applied to $2 \times 10^5$ Daudi cells. The resultant mixture was incubated at 4° C. for 30 min. The cells were pelleted (3 minutes, 400×g), washed once using PBS buffer with 0.5% BSA and re-pelleted. The binding of hLAG-3-mFc to the Daudi cells was detected using an R-PE-conjugated AffiniPure Goat Anti-Human IgG, Fcγ Fragment Specific (Jackson ImmunoResearch) secondary reagent. After that, cells were washed twice as described above, and resuspended in PBS buffer. Analysis of LAG-3-mFc binding was carried out with the BD Accuri C5 flow cytometer (BD Bioscience).

Figure 7:
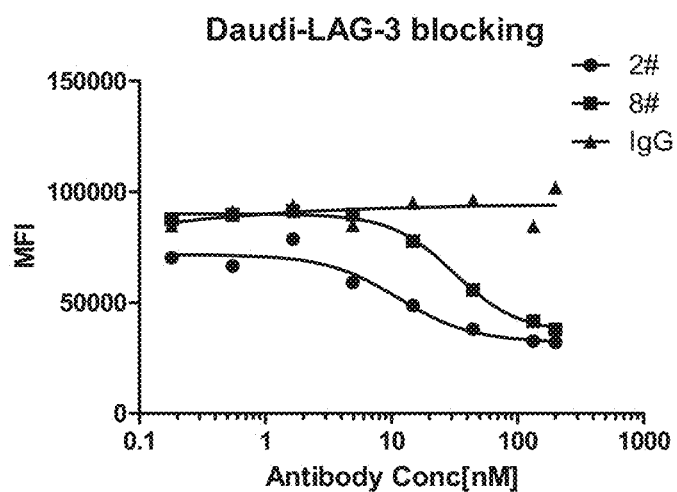
FIG. 7 is a graph showing blocking effect of anti-LAG-3 antibody 2#, 8#, and IgG on interaction of MHC class II molecule with LAG-3.

The $IC_{50}$ values and representative curves for blocking the MHC class II and LAG-3 interaction were shown in FIG. 7.

It can be seen that these clones blocked interaction between MHC class II molecule and LAG-3, with clone 2# showing better effect.

Example 12 Anti-LAG-3 Antibodies Blocked Interaction of LAG-3 with LSECtin

To assess the ability of the anti-LAG-3 antibodies to inhibit human LAG-3 binding to human LSECtin, an ELISA blocking assay was performed.

Human LAG-3 (Acrobiosystems) was immobilized onto 96-well plates by incubation overnight at 4° C. Nonspecific binding sites were blocked by incubation with 1% BSA in PBS for one hour at 37° C. After blocking, the plates were washed three times with PBST (PBS containing 0.05% Tween20). Serially diluted anti-LAG-3 antibodies and human IgG control were prepared in binding buffer (PBS containing 0.05% Tween20 and 0.5% BSA) and mixed with biotin labeled LSECtin (Acrobiosystems), added into plates for one hour at 37° C. After binding, the plates were washed three times with PBST, incubated for 30 min at RT with streptavidin-HRP (R&D Systems). After that, the plates were washed again, developed with TMB and stopped with 1M $H_2SO_4$.

Figure 8:
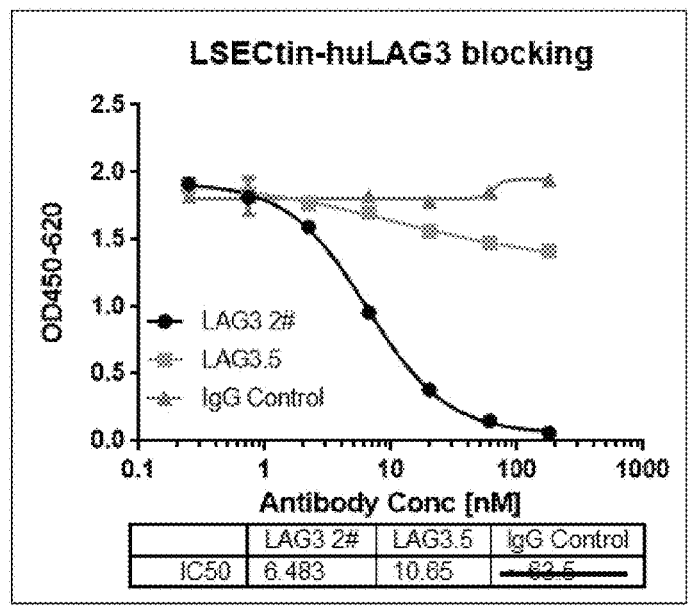
FIG. 8 is a graph showing the blocking effect of anti-LAG-3 antibody 2#, 6#, and IgG on interaction of LSECtin with LAG-3.

The absorbance at 450 nm-620 nm was determined. Representative binding curves for these antibodies were shown in FIG. 8.

The result indicated anti-LAG-3 antibody 2# blocked interaction between human LAG-3 and LSECtin.

Example 13 Anti LAG-3 Antibodies Bound to Cell Surface LAG-3 Expressed by Human T Cells Anti-LAG3 antibodies (Clone 2#, 8#, 13#) were tested for the ability of binding to human LAG-3 expressed on activated human T cells.

Primary T cells were isolated from peripheral blood mononuclear cells with magnetic beads and cultured in tissue culture plates coated with anti-CD3 antibody (OKT3, Biolegend). Anti-LAG-3 antibodies (Clone 2#, 8#, 13#) and negative control IgG4 were added to cells and the mixture was incubated at 4° C. for 30 minutes. The cells were washed twice. The binding activity of the anti-LAG-3 antibodies to LAG-3 expressed on T cells was detected using an R-PE-conjugated AffiniPure Goat Anti-Human IgG, Fcγ Fragment Specific (Jackson ImmunoResearch) secondary reagent, with the mixture incubated at 4° C. for 30 minutes followed by washing twice. Then, cells were resuspended in PBS buffer. Analysis of LAG-3 binding was carried out with the BD Accuri C5 flow cytometer (BD Bioscience).

Figure 9:
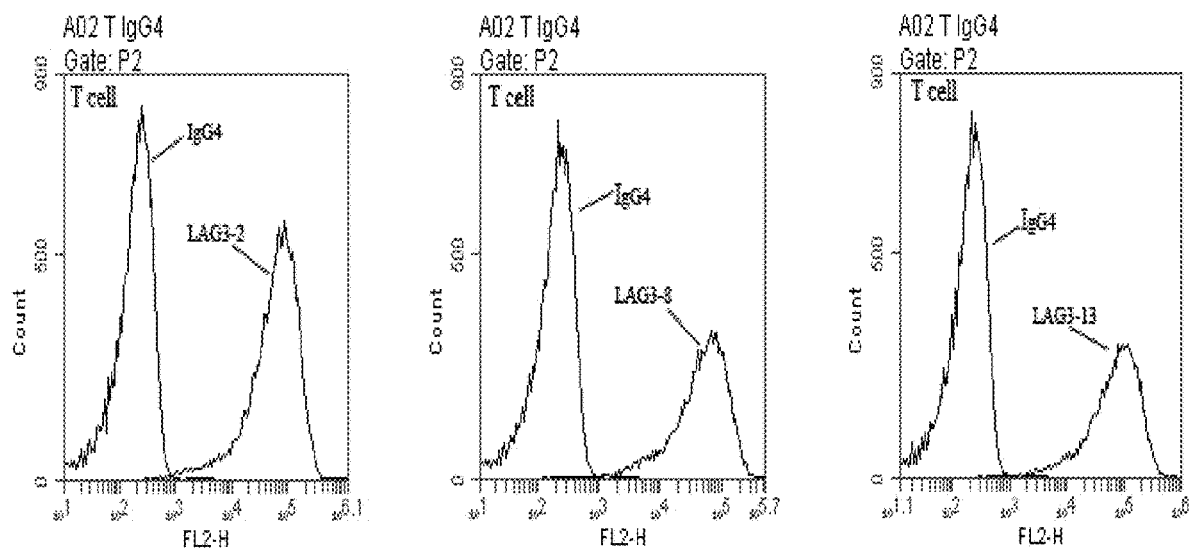
FIG. 9 are graphs showing the binding activity of anti-LAG-3 antibody 2#, 8# and 13# to LAG-3 expressed on surface of activated human T cells.

Representative curves for these clones binding to LAG-3 expressed by human T cells were shown in FIG. 9.

Example 14 Anti-LAG-3 Antibodies Induced Human T Cell to Release IL-2

The functional activity of the anti-LAG3 antibody (Clone 2#) on primary T cells was assessed compared to an anti-PD1 antibody (nivolumab, BMS) and IgG4 (Biolegend), using human PBMC cultures stimulated by the superantigen SEB.

Human PBMCs from healthy donors were stimulated with SEB for 24 hours. Anti-LAG3 antibody 2#, Anti-PD1 antibody and IgG4 were added into medium, respectively. The IL2 level in supernatant was detected by ELISA after 3 days.

Figure 10:
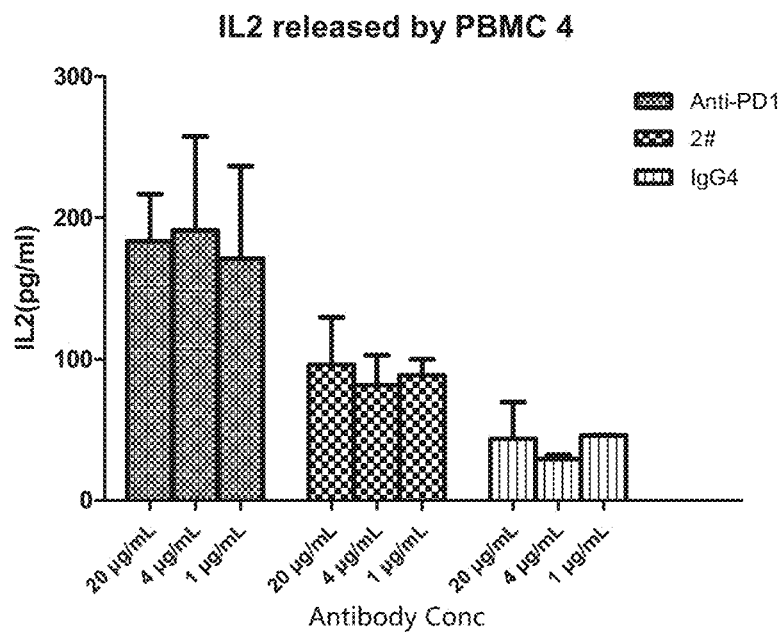
FIG. 10 is a graph showing the IL-2 levels released by human T cells cultured with anti-PD1 antibody, anti-LAG-3 antibody 2# or IgG4.

The IL2 levels were shown in FIG. 10.

Example 15 Anti LAG-3 Antibody Induced Human T Cell to Release IFNg in a Dose Dependent Manner The functional activity of the Anti-LAG3 antibody 2# on primary T cells was assessed using human PBMCs. Human PBMCs from healthy donors were cultured in tissue culture plate coated with anti-CD3 antibody (OKT3, Biolegend) for 24 hours. Anti-LAG3 antibody 2# was serially diluted and added into medium. The IFNg in supernatants was detected by ELISA after 3 days.

Figure 11:
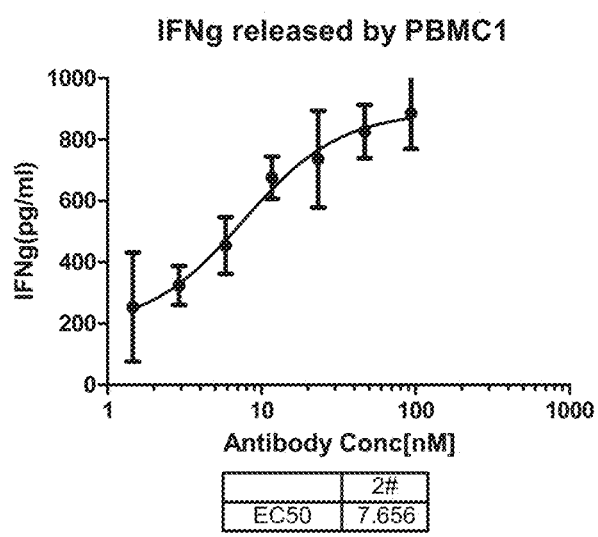
FIG. 11 is a graph showing the IFNg released by human T cells cultured with anti-LAG-3 antibody 2#.

The IFNg level released by PBMC was shown in FIG. 11.

Example 16 Pharmacokinetic of Anti-LAG-3 Antibodies in Cynomolgous Monkeys

Pharmacokinetic profile of Anti-LAG3 antibody 2# in cynomolgous monkeys was evaluated. Procedures involving the care and use of animals in the study were reviewed and approved. Four naive cynomolgus monkeys of Chinese origin were used. In the study, Anti-LAG3 antibody 2# was injected intravenously into animals at a dose of 3 mg/kg or 10 mg/kg. Blood samples were obtained at various timepoints between 0 and 672 hours (0-28 days). All samples were processed to plasma, stored frozen at −70~−86° C. until analyzed. The concentration of Anti-LAG3 antibody 2# present in the serum was determined.

Table 3 showed the pharmacokinetic properties as determined above.

TABLE 3

Summary of pharmacokinetic properties of Anti-LAG3 antibody 2#

| Dose | | $T_{1/2}$ (h) | $AUC_{last}$ (h * μg/mL) | $AUC_{INF\_obs}$ (h * μg/mL) | $V_{Z\_obs}$ (mL/kg) | $Cl_{\_obs}$ (mL/h/kg) |
|---|---|---|---|---|---|---|
| 3 mg/kg | N | 2 | 2 | 2 | 2 | 2 |
| | Mean | 275.31 | 9013.81 | 11364.48 | 109.27 | 0.27 |
| | STD | 13.87 | 2327.64 | 2970.21 | 33.84 | 0.07 |
| 10 mg/kg | N | 2 | 2 | 2 | 2 | 2 |
| | Mean | 335.31 | 26601.72 | 34144.90 | 148.28 | 0.31 |
| | STD | 36.90 | 9867.22 | 12139.57 | 37.13 | 0.11 |

$AUC_{last}$(Area under the plasma level time curve from t = 0 to last measurable plasma drug concentration at time t),
$AUC_{INF\_obs}$ (Area under concentration-time curve 0-∞),
$V_{z\_obs}$ (The volume of distribution),
$Cl_{\_obs}$(Clearance).

Example 17 In Vivo Efficacy of Anti-LAG3 Antibodies Against MC38-OVA Tumors

The in vivo efficacy of the anti-LAG3 antibodies alone or in combination with anti-mouse PD-1 antibodies was studied in a MC38-OVA tumor model.

For the experiments herein, humanized mice B6.129-Lag3$^{tm1(hLAG3)Smoc}$ expressing the extracellular portion of human LAG3 were purchased from Shanghai Model Organism.

Fifty B6.129-Lag3$^{tm1(hLAG3)Smoc}$ mice were subcutaneously implanted with 5×10$^5$ MC38-OVA cells on day 0 and randomized into five treatment groups, N=8 in the PBS group, and N=10 each in IgG4 isotype control, LAG3 2#, anti-mPD1(rat IgG2a anti-mouse PD-1 antibody, clone RPMI-14, BioXCell, Catalog # BE0089), and LAG3 2#+anti-mPD1 combination treatment groups. On days 3, 7, 10, 14 and 17, mice were administered with LAG3 2# (10 mg/kg), anti-mPD1 (10 mg/kg), isotype control antibody (20 mg/kg) or LAG3 2# (10 mg/kg)+anti-mPD1 (10 mg/kg) by intraperitoneal injection. Tumor volumes were monitored by caliper measurement twice per week during the experiment (20 days).

Figure 12:
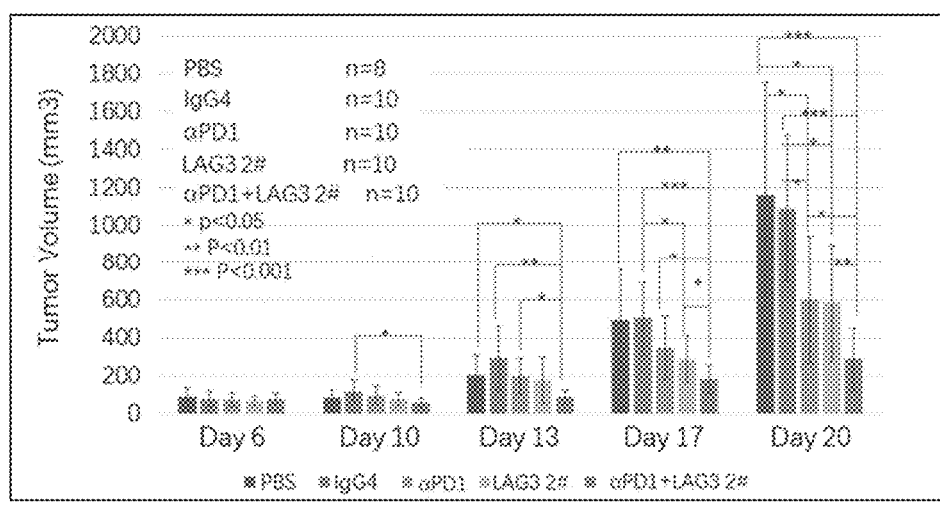
FIG. 12 is a graph showing anti-tumor effect of anti-LAG-3 antibody 2# and/or an anti-PD1 antibody.

Anti-LAG3 antibody 2# and anti-mPD1 monotherapy resulted in tumor growth inhibition compared to PBS or IgG4 isotype control group, and the combination of Anti-LAG3 antibody 2# and Anti-mPD1 resulted in improved efficacy including reduced tumor growth, as shown in FIG. 12.

We claim:

1. An isolated monoclonal antibody, or an antigen-binding portion thereof, that binds LAG-3, comprising a heavy chain variable region and a light chain variable region, wherein the heavy chain variable region comprises a CDR1 region comprising the amino acid sequence of SEQ ID NO:2, a CDR2 region comprising the amino acid sequence of SEQ ID NO:4, and a CDR3 region comprising the amino acid sequence of SEQ ID NO:6, wherein the light chain variable region comprises a CDR1 region comprising the amino acid sequence of SEQ ID NO:8, a CDR2 region comprising the amino acid sequence of SEQ ID NO: 10, and a CDR3 region comprising the amino acid sequence of SEQ ID NO: 12.

2. The isolated monoclonal antibody, or an antigen-binding portion thereof, of claim 1, wherein the heavy chain variable region comprises the amino acid sequence of SEQ ID NO: 32.

3. The isolated monoclonal antibody, or the antigen-binding portion thereof, of claim 1, wherein the light chain variable region comprises the amino acid sequence of SEQ ID NO:34.

4. The isolated monoclonal antibody, or an antigen-binding portion thereof, of claim 1, comprising a heavy chain comprising the amino acid sequence of SEQ ID NO:36, and a light chain comprising the amino acid sequence of SEQ ID NO:38.

5. The isolated monoclonal antibody, or an antigen-binding portion thereof, of claim 1, comprising the amino acid sequence of SEQ ID NO:30.

6. The isolated monoclonal antibody, or the antigen-binding portion thereof, of claim 1, which exhibits one or a combination of the following properties: (a) binding to human LAG-3; (b) binding to monkey LAG-3; (c) lack of binding to mouse LAG-3; (d) binding to LAG-3 at a domain histocompatibility (MHC) class II bind to; (e) inhibits binding of LAG-3 to major histocompatibility (MHC) class II molecules; (f) inhibits binding of LAG-3 to LSECtin; (g) stimulates an immune response; and (h) stimulates an antigen-specific T cell response.

7. The isolated monoclonal antibody, or the antigen-binding portion thereof, of claim 1, which is an IgG1, IgG2 or IgG4 isotype.

8. The isolated monoclonal antibody, or the antigen-binding portion thereof, of claim 1, which is a human, humanized, or chimeric antibody.

9. A composition comprising the isolated monoclonal antibody, or the antigen-binding portion thereof, of claim 1, and a pharmaceutically acceptable carrier.

10. The composition of claim 9, further comprising an anti-cancer agent or an anti-viral agent.

11. A method of treating tumor or viral infection in a subject comprising administering to the subject the isolated monoclonal antibody, or antigen-binding portion thereof, of claim 1.

12. The method of claim 11, wherein at least one additional immunostimulatory antibody is further administered to the subject.

13. The method of claim 12, wherein the immunostimulatory antibody is an anti-PD-1 antibody, an anti-PD-L1 antibody or an anti-CTLA-4 antibody.

14. The method of claim 11, wherein, a cytokine is further administered to the subject.

15. The method of claim 14, wherein, the cytokine is IL-2 or IL-21.

16. The method of claim 11, wherein, a costimulatory antibody is further administered to the subject.

17. The method of claim 16, wherein, the costimulatory antibody is an anti-CD137 or an anti-GITR antibody.

18. The isolated monoclonal antibody, or an antigen-binding portion thereof, of claim 1, wherein the heavy chain variable region comprises the amino acid sequence of SEQ ID NO:32, and the light chain variable region comprises the amino acid sequence of SEQ ID NO: 34.

19. The method of claim 11, wherein the subject is human.

* * * * *